(12) United States Patent
Lee et al.

(10) Patent No.: US 10,544,196 B2
(45) Date of Patent: Jan. 28, 2020

(54) COMPOSITION CONTAINING SMAD PROTEIN FOR TREATMENT OF AUTOIMMUNE DISEASES, A FUSION PROTEIN COMPRISING SMAD PROTEIN, AN EXPRESSION VECTOR AND A METHOD FOR PREPARING THE SAME

(71) Applicant: Sang-Kyou Lee, Seoul (KR)

(72) Inventors: Sang-Kyou Lee, Seoul (KR); Sung-Dong Park, Seoul (KR); Sang Won Lee, Seoul (KR); Chin Hee Mun, Seoul (KR)

(73) Assignee: Good T Cells, Inc., Seoul (KR)

( * ) Notice: Subject to any disclaimer, the term of this patent is extended or adjusted under 35 U.S.C. 154(b) by 92 days.

(21) Appl. No.: 15/342,302

(22) Filed: Nov. 3, 2016

(65) Prior Publication Data
US 2017/0210783 A1    Jul. 27, 2017

(30) Foreign Application Priority Data
Jan. 25, 2016  (KR) .................. 10-2016-0008782

(51) Int. Cl.
*C07K 14/47* (2006.01)
*A61K 38/00* (2006.01)

(52) U.S. Cl.
CPC .............. *C07K 14/47* (2013.01); *A61K 38/00* (2013.01); *C07K 2319/00* (2013.01)

(58) Field of Classification Search
CPC ........ A61K 38/00; A61K 48/00; C07K 14/47; C07K 2319/00
See application file for complete search history.

(56) References Cited

U.S. PATENT DOCUMENTS

2013/0267456 A1* 10/2013 Wang ................. A61K 38/1709
514/1.1

OTHER PUBLICATIONS

Huang et al., Acta Biochim Biophys Sin, 2011, 43: 110-117. (Year: 2011).*
Park, "Therapeutic effect of transducible Smad3 and p65 transcription modulation domain in inflammatory diseases", A Dissertation submitted to the Division of Life Science & Biotechnology and the Graduate School of Yonsei University (Aug. 1, 2015).

* cited by examiner

*Primary Examiner* — Kaipeen E Yang
(74) *Attorney, Agent, or Firm* — McDonnell Boehnen Hulbert & Berghoff LLP

(57) ABSTRACT

The present invention relates to a composition and a fusion protein for prevention or treatment of autoimmune diseases, which contain a Smad protein, and provides a method for prevention or treatment of autoimmune diseases, including lupus nephritis and rheumatoid arthritis.

9 Claims, 38 Drawing Sheets

Specification includes a Sequence Listing.

M: Marker
Lane 1: Smad3
Lane 2: tSmad3
Lane 3: Smad3(MH1)
Lane 4: tSmad3(MH1)
Lane 5: tSmad3(MH1) (mut)

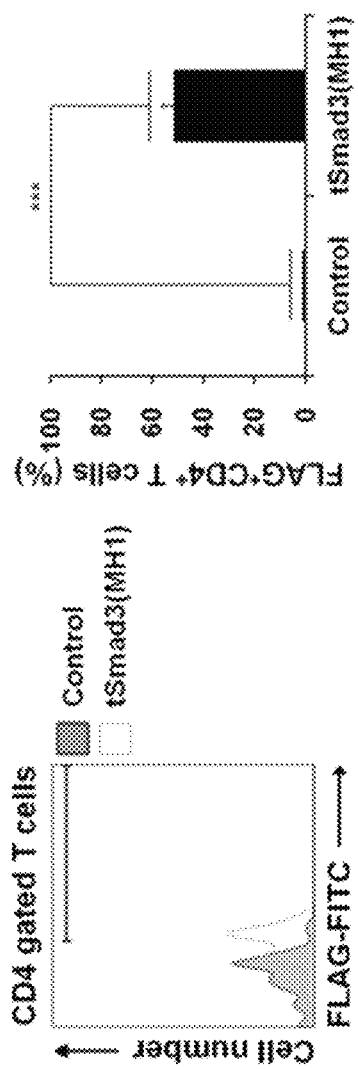
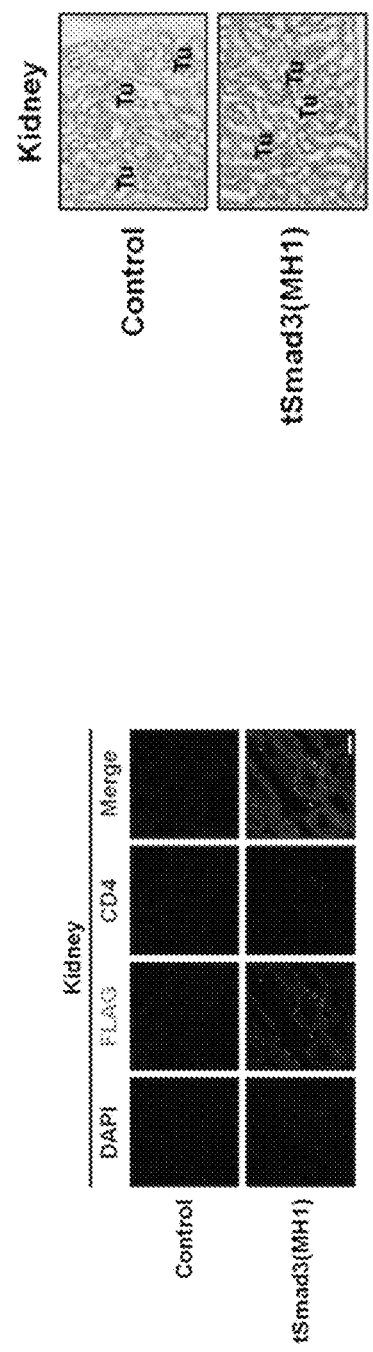
FIG. 8A
FIG. 8B
FIG. 8C

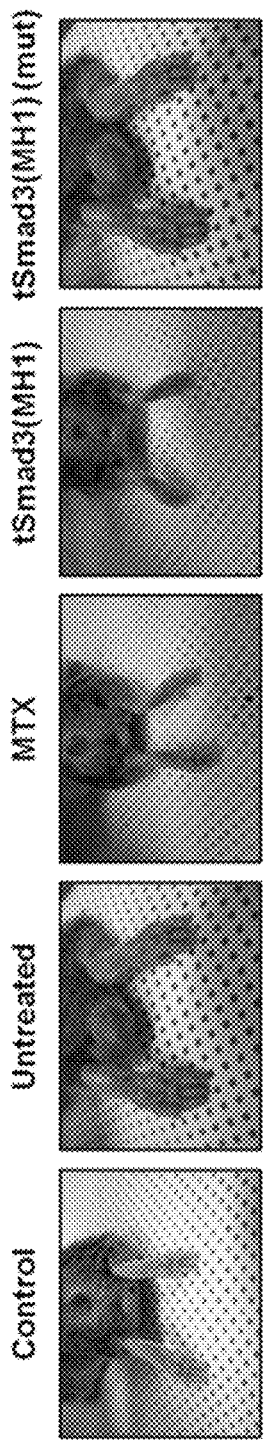
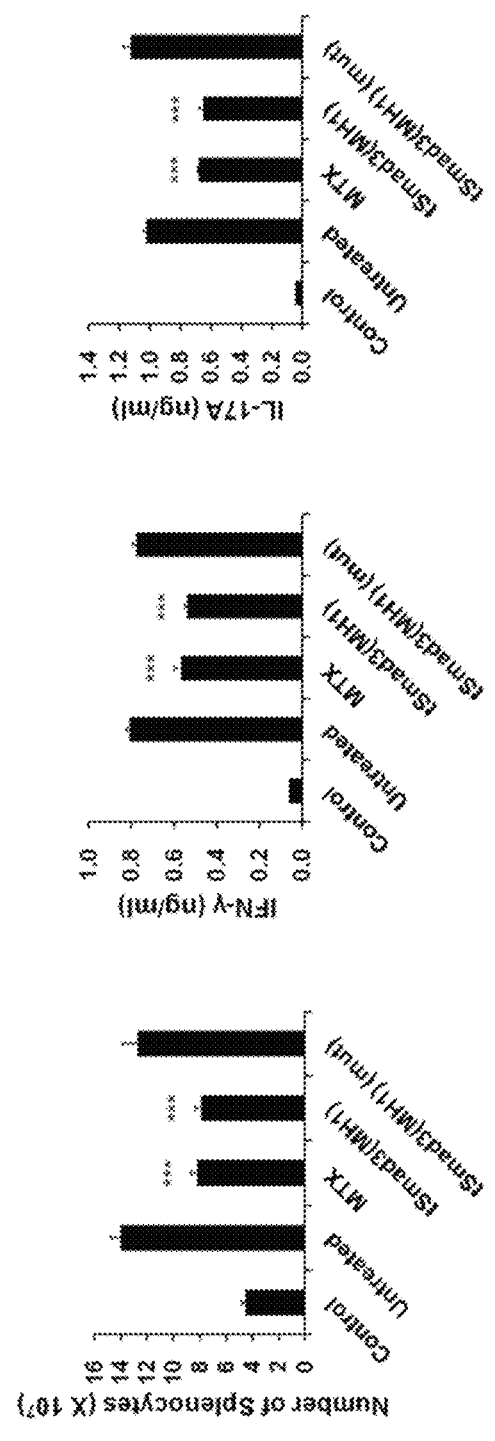
FIG. 11B
FIG. 11C
FIG. 11D
FIG. 11E

SEQUENCE LISTING

```
<160> NUMBER OF SEQ ID NOS: 10

<210> SEQ ID NO 1
<211> LENGTH: 425
<212> TYPE: PRT
<213> ORGANISM: Artificial Sequence
<220> FEATURE:
<223> OTHER INFORMATION: Amino acid sequence of Smad3

<400> SEQUENCE: 1

Met Ser Ser Ile Leu Pro Phe Thr Pro Pro Ile Val Lys Arg Leu Leu
1               5                   10                  15

Gly Trp Lys Lys Gly Glu Gln Asn Gly Gln Glu Glu Lys Trp Cys Glu
            20                  25                  30

Lys Ala Val Lys Ser Leu Val Lys Lys Leu Lys Lys Thr Gly Gln Leu
        35                  40                  45
```

```
Asp Glu Leu Glu Lys Ala Ile Thr Thr Gln Asn Val Asn Thr Lys Cys
 50                  55                  60

Ile Thr Ile Pro Arg Ser Leu Asp Gly Arg Leu Gln Val Ser His Arg
 65                  70                  75                  80

Lys Gly Leu Pro His Val Ile Tyr Cys Arg Leu Trp Arg Trp Pro Asp
                 85                  90                  95

Leu His Ser His His Glu Leu Arg Ala Met Glu Leu Cys Glu Phe Ala
            100                 105                 110

Phe Asn Met Lys Lys Asp Glu Val Cys Val Asn Pro Tyr His Tyr Gln
        115                 120                 125

Arg Val Glu Thr Pro Val Leu Pro Pro Val Leu Val Pro Arg His Thr
130                 135                 140

Glu Ile Pro Ala Glu Phe Pro Pro Leu Asp Asp Tyr Ser His Ser Ile
145                 150                 155                 160

Pro Glu Asn Thr Asn Phe Pro Ala Gly Ile Glu Pro Gln Ser Asn Ile
                165                 170                 175

Pro Glu Thr Pro Pro Pro Gly Tyr Leu Ser Glu Asp Gly Glu Thr Ser
            180                 185                 190

Asp His Gln Met Asn His Ser Met Asp Ala Gly Ser Pro Asn Leu Ser
        195                 200                 205

Pro Asn Pro Met Ser Pro Ala His Asn Asn Leu Asp Leu Gln Pro Val
210                 215                 220

Thr Tyr Cys Glu Pro Ala Phe Trp Cys Ser Ile Ser Tyr Tyr Glu Leu
225                 230                 235                 240

Asn Gln Arg Val Gly Glu Thr Phe His Ala Ser Gln Pro Ser Met Thr
                245                 250                 255

Val Asp Gly Phe Thr Asp Pro Ser Asn Ser Glu Arg Phe Cys Leu Gly
            260                 265                 270

Leu Leu Ser Asn Val Asn Arg Asn Ala Ala Val Glu Leu Thr Arg Arg
        275                 280                 285

His Ile Gly Arg Gly Val Arg Leu Tyr Tyr Ile Gly Gly Glu Val Phe
290                 295                 300

Ala Glu Cys Leu Ser Asp Ser Ala Ile Phe Val Gln Ser Pro Asn Cys
305                 310                 315                 320

Asn Gln Arg Tyr Gly Trp His Pro Ala Thr Val Cys Lys Ile Pro Pro
                325                 330                 335

Gly Cys Asn Leu Lys Ile Phe Asn Asn Gln Glu Phe Ala Ala Leu Leu
            340                 345                 350

Ala Gln Ser Val Asn Gln Gly Phe Glu Ala Val Tyr Gln Leu Thr Arg
        355                 360                 365

Met Cys Thr Ile Arg Met Ser Phe Val Lys Gly Trp Gly Ala Glu Tyr
370                 375                 380

Arg Arg Gln Thr Val Thr Ser Thr Pro Cys Trp Ile Glu Leu His Leu
385                 390                 395                 400

Asn Gly Pro Leu Gln Trp Leu Asp Lys Val Leu Thr Gln Met Gly Ser
                405                 410                 415

Pro Ser Ile Arg Cys Ser Ser Val Ser
            420                 425

<210> SEQ ID NO 2
<211> LENGTH: 1278
<212> TYPE: DNA
<213> ORGANISM: Artificial Sequence
<220> FEATURE:
<223> OTHER INFORMATION: Nucleotide sequence of Smad3
```

-continued

<400> SEQUENCE: 2

```
atgtcgtcca tcctgccttt cactcccccg atcgtgaagc gcctgctggg ctggaagaag    60
ggcgagcaga acgggcagga ggagaaatgg tgcgagaagg cggtcaagag cctggtcaag   120
aaactcaaga agacggggca gctggacgag ctggagaagg ccatcaccac gcagaacgtc   180
aacaccaagt gcatcaccat ccccaggtcc ctggatggcc ggttgcaggt gtcccatcgg   240
aagggggctcc ctcatgtcat ctactgccgc tgtggcgat ggccagacct gcacagccac   300
cacgagctac gggccatgga gctgtgtgag ttcgccttca atatgaagaa ggacgaggtc   360
tgcgtgaatc cctaccacta ccagagagta gagacaccag ttctacctcc tgtgttggtg   420
ccacgccaca cagagatccc ggccgagttc ccccactgg acgactacag ccattccatc   480
cccgaaaaca ctaacttccc cgcaggcatc gagccccaga gcaatattcc agagacccca   540
cccctggct acctgagtga agatggagaa accagtgacc accagatgaa ccacagcatg   600
gacgcaggtt ctccaaacct atccccgaat ccgatgtccc cagcacataa taacttggac   660
ctgcagccag ttacctactg cgagccggcc ttctggtgct ccatctccta ctacgagctg   720
aaccagcgcg tcgggggagac attccacgcc tcgcagccat ccatgactgt ggatggcttc   780
accgaccct ccaattcgga gcgcttctgc ctagggctgc tctccaatgt caacaggaat   840
gcagcagtgg agctgacacg gagacacatc ggaagaggcg tgcggctcta ctacatcgga   900
ggggaggtct tcgcagagtg cctcagtgac agcgctattt tgtccagtc tcccaactgt   960
aaccagcgct atggctggca cccggccacc gtctgcaaga tcccaccagg atgcaacctg  1020
aagatcttca caaccagga gttcgctgcc ctcctggccc agtcggtcaa ccagggcttt  1080
gaggctgtct accagttgac ccgaatgtgc accatccgca tgagcttcgt caaaggctgg  1140
ggagcggagt acaggagaca gactgtgacc agtacccct gctggattga gctgcacctg  1200
aatgggcctt tgcagtggct tgacaaggtc ctcacccaga tgggctcccc aagcatccgc  1260
tgttccagtg tgtcttag                                                1278
```

<210> SEQ ID NO 3
<211> LENGTH: 142
<212> TYPE: PRT
<213> ORGANISM: Artificial Sequence
<220> FEATURE:
<223> OTHER INFORMATION: Amino acid sequence of Smad3(MH1) domain

<400> SEQUENCE: 3

```
Met Ser Ser Ile Leu Pro Phe Thr Pro Pro Ile Val Lys Arg Leu Leu
1               5                   10                  15

Gly Trp Lys Lys Gly Glu Gln Asn Gly Gln Glu Glu Lys Trp Cys Glu
                20                  25                  30

Lys Ala Val Lys Ser Leu Val Lys Lys Leu Lys Lys Thr Gly Gln Leu
            35                  40                  45

Asp Glu Leu Glu Lys Ala Ile Thr Thr Gln Asn Val Asn Thr Lys Cys
        50                  55                  60

Ile Thr Ile Pro Arg Ser Leu Asp Gly Arg Leu Gln Val Ser His Arg
65                  70                  75                  80

Lys Gly Leu Pro His Val Ile Tyr Cys Arg Leu Trp Arg Trp Pro Asp
                85                  90                  95

Leu His Ser His His Glu Leu Arg Ala Met Glu Leu Cys Glu Phe Ala
                100                 105                 110

Phe Asn Met Lys Lys Asp Glu Val Cys Val Asn Pro Tyr His Tyr Gln
```

```
                    115                 120                 125
Arg Val Glu Thr Pro Val Leu Pro Pro Val Leu Val Pro Arg
    130                 135                 140

<210> SEQ ID NO 4
<211> LENGTH: 426
<212> TYPE: DNA
<213> ORGANISM: Artificial Sequence
<220> FEATURE:
<223> OTHER INFORMATION: Nucleotide sequence of Smad3(MH1) domain

<400> SEQUENCE: 4
atgtcgtcca tcctgccttt cactccccg  atcgtgaagc gcctgctggg ctggaagaag    60
ggcgagcaga acgggcagga ggagaaatgg tgcgagaagg cggtcaagag cctggtcaag   120
aaactcaaga agacggggca gctggacgag ctggagaagg ccatcaccac gcagaacgtc   180
aacaccaagt gcatcaccat ccccaggtcc ctggatggcc ggttgcaggt gtcccatcgg   240 aagggggctcc ctcatgtcat ctactgccgc tgtggcgat ggccagacct gcacagccac   300
cacgagctac gggccatgga gctgtgtgag ttcgccttca atatgaagaa ggacgaggtc   360
tgcgtgaatc cctaccacta ccagagagta gagacaccag ttctacctcc tgtgttggtg   420
ccacgc                                                              426

<210> SEQ ID NO 5
<211> LENGTH: 11
<212> TYPE: PRT
<213> ORGANISM: Artificial Sequence
<220> FEATURE:
<223> OTHER INFORMATION: Amino acid sequence of Hph-1

<400> SEQUENCE: 5

Tyr Ala Arg Val Arg Arg Arg Gly Pro Arg Arg
1               5                   10

<210> SEQ ID NO 6
<211> LENGTH: 33
<212> TYPE: DNA
<213> ORGANISM: Artificial Sequence
<220> FEATURE:
<223> OTHER INFORMATION: Nucleotide sequence of Hph-1

<400> SEQUENCE: 6
tatgcacgtg ttcggaggcg tggaccccgc cgc                                 33

<210> SEQ ID NO 7
<211> LENGTH: 471
<212> TYPE: PRT
<213> ORGANISM: Artificial Sequence
<220> FEATURE:
<223> OTHER INFORMATION: Amino acid sequence of tSmad3

<400> SEQUENCE: 7

Met Gly Ser Ser His His His His His Ser Ser Gly Leu Val Pro
1               5                   10                  15

Arg Gly Ser His Met Ala Ser Gly Tyr Ala Arg Val Arg Arg Gly
                20                  25                  30

Pro Arg Arg Gly Gly Ser Asp Tyr Lys Asp Asp Asp Lys Met Ser
            35                  40                  45

Ser Ile Leu Pro Phe Thr Pro Pro Ile Val Lys Arg Leu Leu Gly Trp
        50                  55                  60

Lys Lys Gly Glu Gln Asn Gly Gln Glu Glu Lys Trp Cys Glu Lys Ala
```

65                  70                  75                  80
Val Lys Ser Leu Val Lys Lys Leu Lys Lys Thr Gly Gln Leu Asp Glu
                    85                  90                  95
Leu Glu Lys Ala Ile Thr Thr Gln Asn Val Asn Thr Lys Cys Ile Thr
                100                 105                 110
Ile Pro Arg Ser Leu Asp Gly Arg Leu Gln Val Ser His Arg Lys Gly
                115                 120                 125
Leu Pro His Val Ile Tyr Cys Arg Leu Trp Arg Trp Pro Asp Leu His
            130                 135                 140
Ser His His Glu Leu Arg Ala Met Glu Leu Cys Glu Phe Ala Phe Asn
145                 150                 155                 160
Met Lys Lys Asp Glu Val Cys Val Asn Pro Tyr His Tyr Gln Arg Val
                165                 170                 175
Glu Thr Pro Val Leu Pro Pro Val Leu Val Pro Arg His Thr Glu Ile
                180                 185                 190
Pro Ala Glu Phe Pro Pro Leu Asp Asp Tyr Ser His Ser Ile Pro Glu
                195                 200                 205
Asn Thr Asn Phe Pro Ala Gly Ile Glu Pro Gln Ser Asn Ile Pro Glu
            210                 215                 220
Thr Pro Pro Pro Gly Tyr Leu Ser Glu Asp Gly Glu Thr Ser Asp His
225                 230                 235                 240
Gln Met Asn His Ser Met Asp Ala Gly Ser Pro Asn Leu Ser Pro Asn
                245                 250                 255
Pro Met Ser Pro Ala His Asn Asn Leu Asp Leu Gln Pro Val Thr Tyr
                260                 265                 270
Cys Glu Pro Ala Phe Trp Cys Ser Ile Ser Tyr Tyr Glu Leu Asn Gln
                275                 280                 285
Arg Val Gly Glu Thr Phe His Ala Ser Gln Pro Ser Met Thr Val Asp
            290                 295                 300
Gly Phe Thr Asp Pro Ser Asn Ser Glu Arg Phe Cys Leu Gly Leu Leu
305                 310                 315                 320
Ser Asn Val Asn Arg Asn Ala Ala Val Glu Leu Thr Arg Arg His Ile
                325                 330                 335
Gly Arg Gly Val Arg Leu Tyr Tyr Ile Gly Gly Glu Val Phe Ala Glu
                340                 345                 350
Cys Leu Ser Asp Ser Ala Ile Phe Val Gln Ser Pro Asn Cys Asn Gln
                355                 360                 365
Arg Tyr Gly Trp His Pro Ala Thr Val Cys Lys Ile Pro Pro Gly Cys
            370                 375                 380
Asn Leu Lys Ile Phe Asn Asn Gln Glu Phe Ala Ala Leu Leu Ala Gln
385                 390                 395                 400
Ser Val Asn Gln Gly Phe Glu Ala Val Tyr Gln Leu Thr Arg Met Cys
                405                 410                 415
Thr Ile Arg Met Ser Phe Val Lys Gly Trp Gly Ala Glu Tyr Arg Arg
                420                 425                 430
Gln Thr Val Thr Ser Thr Pro Cys Trp Ile Glu Leu His Leu Asn Gly
            435                 440                 445
Pro Leu Gln Trp Leu Asp Lys Val Leu Thr Gln Met Gly Ser Pro Ser
            450                 455                 460
Ile Arg Cys Ser Ser Val Ser
465                 470

<210> SEQ ID NO 8

<211> LENGTH: 1416
<212> TYPE: DNA
<213> ORGANISM: Artificial Sequence
<220> FEATURE:
<223> OTHER INFORMATION: Nucleotide sequence of tSmad3

<400> SEQUENCE: 8

```
atgggcagca gccatcatca tcatcatcac agcagcggcc tggtgccgcg cggcagccat      60
atggctagcg gctatgcacg tgttcggagg cgtggacccc gccgcggcgg atccgactac     120
aaggacgacg atgacaagat gtcgtccatc ctgcctttca ctcccccgat cgtgaagcgc     180
ctgctgggct ggaagaaggg cgagcagaac gggcaggagg agaaatggtg cgagaaggcg     240
gtcaagagcc tggtcaagaa actcaagaag acggggcagc tggacgagct ggagaaggcc     300
atcaccacgc agaacgtcaa caccaagtgc atcaccatcc caggtccct ggatggccgg      360
ttgcaggtgt cccatcggaa ggggctccct catgtcatct actgccgcct gtggcgatgg     420
ccagacctgc acagccacca cgagctgcgg gccatggagc tgtgtgagtt cgccttcaat     480
atgaagaagg acgaggtctg cgtgaatccc taccactacc agagagtaga caccagtt      540
ctacctcctg tgttggtgcc acgccacaca gagatcccgg ccgagttccc cccactggac     600
gactacagcc attccatccc cgaaaacact aacttccccg caggcatcga gcccagagc     660
aatattccag accccacc ccctggctac ctgagtgaag atggagaaac cagtgaccac      720
cagatgaacc acagcatgga cgcaggttct ccaaacctat ccccgaatcc gatgtcccca     780
gcacataata acttggacct gcagccagtt acctactgcg agccggcctt ctggtgctcc     840
atctcctact acgagctgaa ccagcgcgtc ggggagacat ccacgcctc gcagccatcc      900
atgactgtgg atggcttcac cgacccctcc aattcggagc gcttctgcct agggctgctc     960
tccaatgtca caggaatgc agcagtggag ctgacacgga gacacatcgg aagaggcgtg     1020
cggctctact acatcggagg ggaggtcttc gcagagtgcc tcagtgacag cgctattttt     1080
gtccagtctc ccaactgtaa ccagcgctat ggctggcacc cggccaccgt ctgcaagatc     1140
ccaccaggat gcaacctgaa gatcttcaac aaccaggagt cgctgccct cctggcccag     1200
tcggtcaacc agggctttga ggctgtctac cagttgaccc caatgtgcac catccgcatg     1260
agcttcgtca aaggctgggg agcggagtac aggagacaga ctgtgaccag tacccctgc     1320
tggattgagc tgcacctgaa tgggcctttg cagtggcttg acaaggtcct cacccagatg     1380
ggctccccaa gcatccgctg ttccagtgtg tcttag                              1416
```

<210> SEQ ID NO 9
<211> LENGTH: 190
<212> TYPE: PRT
<213> ORGANISM: Artificial Sequence
<220> FEATURE:
<223> OTHER INFORMATION: Amino acid sequence of tSmad3(MH1)

<400> SEQUENCE: 9

```
Met Gly Ser Ser His His His His His His Ser Gly Leu Val Pro
1               5                   10                  15

Arg Gly Ser His Met Ala Ser Gly Tyr Ala Arg Val Arg Arg Arg Gly
                20                  25                  30

Pro Arg Arg Gly Gly Ser Asp Tyr Lys Asp Asp Asp Lys Glu Phe
            35                  40                  45

Met Ser Ser Ile Leu Pro Phe Thr Pro Pro Ile Val Lys Arg Leu Leu
        50                  55                  60

Gly Trp Lys Lys Gly Glu Gln Asn Gly Gln Glu Glu Lys Trp Cys Glu
```

```
                65                  70                  75                  80
            Lys Ala Val Lys Ser Leu Val Lys Lys Leu Lys Lys Thr Gly Gln Leu
                            85                  90                  95

Asp Glu Leu Glu Lys Ala Ile Thr Thr Gln Asn Val Asn Thr Lys Cys
                           100                 105                 110

Ile Thr Ile Pro Arg Ser Leu Asp Gly Arg Leu Gln Val Ser His Arg
                           115                 120                 125

Lys Gly Leu Pro His Val Ile Tyr Cys Arg Leu Trp Arg Trp Pro Asp
                           130                 135                 140

Leu His Ser His His Glu Leu Arg Ala Met Glu Leu Cys Glu Phe Ala
            145                 150                 155                 160

Phe Asn Met Lys Lys Asp Glu Val Cys Val Asn Pro Tyr His Tyr Gln
                           165                 170                 175

Arg Val Glu Thr Pro Val Leu Pro Pro Val Leu Val Pro Arg
                           180                 185                 190

<210> SEQ ID NO 10
<211> LENGTH: 573
<212> TYPE: DNA
<213> ORGANISM: Artificial Sequence
<220> FEATURE:
<223> OTHER INFORMATION: Nucleotide sequence of tSmad3(MH1)

<400> SEQUENCE: 10
atgggcagca gccatcatca tcatcatcac agcagcggcc tggtgccgcg cggcagccat      60
atggctagcg gctatgcacg tgttcggagg cgtggacccc gccgcggcgg atccgactac     120
aaggacgacg atgacaagga attcatgtcg tccatcctgc ctttcactcc cccgatcgtg     180
aagcgcctgc tgggctggaa gaagggcgag cagaacgggc aggaggagaa atggtgcgag     240
aaggcggtca agagcctggt caagaaactc aagaagacgg ggcagctgga cgagctggag     300
aaggccatca ccacgcagaa cgtcaacacc aagtgcatca ccatcccag gtccctggat      360 ggccggttgc aggtgtccca tcggaagggg ctccctcatg tcatctactg ccgcctgtgg     420
cgatggccag acctgcacag ccaccacgag ctgcgggcca tggagctgtg tgagttcgcc     480
ttcaatatga agaaggacga ggtctgcgtg aatccctacc actaccagag agtagagaca     540
ccagttctac ctcctgtgtt ggtgccacgc tag                                  573
```

COMPOSITION CONTAINING SMAD PROTEIN FOR TREATMENT OF AUTOIMMUNE DISEASES, A FUSION PROTEIN COMPRISING SMAD PROTEIN, AN EXPRESSION VECTOR AND A METHOD FOR PREPARING THE SAME

CROSS-REFERENCE TO RELATED APPLICATION

This application claims priority to Korean Patent Application No. 10-2016-0008782, filed on Jan. 25, 2016, the disclosure of which is incorporated herein by reference in its entirety.

BACKGROUND OF THE INVENTION

Field of the Invention

The present invention relates to a composition and a fusion protein for prevention or treatment of autoimmune diseases, which contain a Smad protein, and provides a method for prevention or treatment of autoimmune diseases, including lupus nephritis and rheumatoid arthritis.

Description of the Related Art

The human immune system functions to protect the body from foreign antigens, but does not attack self-tissue due to self-tolerance. However, when the self-tolerance of the immune system is broken, immune cells may recognize, as foreign objects, proteins that are normally expressed by their genes, to produce antibodies or cause T-cell responses, thereby destroying normal tissue. This process is referred to as "autoimmune", and specific symptoms caused by this process are referred to as "autoimmune diseases".

In the mid-1980s, Mosmann et al. reported that helper T lymphocytes (Th) could be classified into two subsets (Th1 and Th2), based on their pattern of cytokine secretion (Mosmann T R, et al., J Immunol., 136:2348-2357, 1986). Since then, it has been known that Th1 cells secrete IFN-γ and activate macrophages and the like to induce cellular immune responses, and Th2 cells secrete IL-4, IL-5 and the like and are involved in humoral immune responses.

In addition, it is known that excessive differentiation into Th1 cells due to an imbalance between Th1 cells and Th2 cells induces inflammatory autoimmune diseases. However, as it was reported that mice lacking IFN-γ or IFN receptors suffer from autoimmune diseases such as rheumatoid arthritis and multiple sclerosis, doubt on the Th1/Th2 paradigm was cast (Infante-Duarte C, et al., J Immunol., 165: 6107-6115, 2000). Furthermore, studies on IL-12 and IL-23 revealed that Th17 cells induced by IL-23 are more important in causing autoimmune diseases than Th1 cells (Murphy K M, et al., Nat Rev Immunol 2(12):933-44, 2002; Cua D J, et al., 421(6924):744-8, 2003; Langrish C L, et al., J Exp Med 201(2):233-40, 2005).

Th17 cells were named because the T cells induced by IL-23 secrete IL-17 cytokine. It was found that these Th17 cells are distinct from Th1 or Th2 cells. As the Th17 cell transcription factor RORγt was recently identified, signal transduction pathways or transcription processes in Th17 cells were established.

In addition, it is known that, unlike Th1, Th2 and Treg (regulatory T) cells, Th17 cells are involved in the forefront of inflammatory responses appearing in autoimmune diseases and maximize inflammatory response signals to accelerate the progression of the disease. Thus, the development of autoimmune disease therapeutic agents that target the inhibition of Th17 cell activity is attracting a great deal of attention.

Systemic lupus erythematosus (SLE) is a chronic autoimmune disease that causes inflammation of various organs, including the skin, joints, kidneys, lungs and nervous system, due to abnormalities in the immune system that protects the human body from foreign invaders. A serious complication of systemic lupus erythematosus, which attacks kidneys to reduce renal function, is lupus nephritis (LN).

Although many different immunologic and nonimmunologic factors contribute to disease expression in lupus nephritis, the production of pathogenic autoantibodies against nuclear and endogenous antigens, the formation of glomerular immune deposits and the activation of complement cascades are typically initial events.

Rheumatoid arthritis (RA) is a chronic inflammatory autoimmune disease characterized by polyarthritis. In rheumatoid arthritis, inflammation occurs in the intra-articular synovium while erythrocytes in blood are localized to joints. As a result, joint fluid increases, joints swell to cause pain, and inflammatory synovial tissue gradually grows to penetrate bone and cartilage to deform joints, thus hindering joint movement.

The autoimmune disease rheumatoid arthritis characterized by systemic complications, including progressive damage to joints and cardiovascular diseases, results in the loss of immune tolerance due to citrullination caused by environmental or genetic factors. Responses to citrulline are observed in T cells and B cells and appear secondarily in lymphatic tissue or marrow. In addition, intra-articular synovitis in rheumatoid arthritis forms a positive feedback loop by various inflammatory cells and inflammatory substances, and thus can cause continuous inflammation and systemic complications.

Methods for treatment of lupus nephritis and rheumatoid arthritis have dramatically changed, and thus new therapeutic drugs have been continuously developed, and various therapeutic methods, including single methods and combined methods, have been studied. Despite such continuous studies, curative treatment of lupus nephritis and rheumatoid arthritis is still difficult.

Accordingly, the present inventors have attempted to develop a method for treatment of autoimmune diseases, which has high target specificity and also has minimized side effects due to non-cytotoxicity, by use of a specific protein group which is involved in immune system signaling.

SUMMARY OF THE INVENTION

The present invention has been made in order to solve the above-described problems occurring in the present invention, and it is an object of the present invention to provide a method for curative treatment of autoimmune diseases, including lupus nephritis or rheumatoid arthritis.

In accordance with one aspect of the present invention, there is a provided a composition for prevention or treatment of an autoimmune disease, containing a Smad protein or a Smad transcription modulation domain protein as an active ingredient.

In one embodiment, the Smad protein may be one or more selected from the group consisting of Smad1, Smad2, Smad3, Smad4, Smad5, Smad6, Smad7 and Smad8.

In one embodiment, the composition may contain a Smad3 protein or a Smad3 transcription modulation domain protein as an active ingredient.

In one embodiment, the Smad3 protein may comprise an amino acid sequence of SEQ ID NO: 1, and the Smad3 transcription modulation domain protein may comprise an amino acid sequence of SEQ ID NO: 3.

In one embodiment, the Smad3 protein may be encoded by a nucleic acid sequence of SEQ ID NO: 2, and the Smad3 transcription modulation domain protein may be encoded by a nucleic acid sequence of SEQ ID NO: 4.

In one embodiment, the autoimmune disease may be one or more selected from the group consisting of systemic lupus erythematosus, rheumatoid arthritis, septic shock, allergic asthma, allergic nasitis, atopic dermatitis, ulcerative colitis, dacryoadenitis, Alzheimer's disease, stroke, arteriosclerosis, vascular restenosis, type I diabetes, type II diabetes, urticaria, conjunctivitis, psoriasis, systemic inflammatory response syndrome, polymyositis, dermatomyositis, polyarthritis nodosa, mixed connective tissue disease, Sjogren's syndrome, gout, Parkinson's disease, amyotrophic lateral sclerosis, diabetic retinopathy, multiple sclerosis, Crohn's disease, chronic thyroiditis, Celiac disease, myasthenia gravis, pemphigus vulgaris, viral diseases, bacterial diseases, radiation-induced disorders, arteriosclerosis, hemangioma, angiofibroma, reperfusion injury, and cardiac hypertrophy.

In accordance with another aspect of the present invention, there is provided a fusion protein for prevention or treatment of an autoimmune disease, comprising: a Smad protein or a Smad transcription modulation domain protein; and a protein transduction domain.

In one embodiment, the Smad protein may be one or more selected from the group consisting of Smad1, Smad2, Smad3, Smad4, Smad5, Smad6, Smad7 and Smad8.

In one embodiment, the fusion protein may comprise: a Smad3 protein or a Smad3 transcription modulation domain protein; and a protein transduction domain.

In one embodiment, the Smad3 protein may comprise an amino acid sequence of SEQ ID NO: 1, and the Smad3 transcription modulation domain protein may comprise an amino acid sequence of SEQ ID NO: 3.

In one embodiment, the Smad3 protein may be encoded by a nucleic acid sequence of SEQ ID NO: 2, and the Smad3 transcription modulation domain protein may be encoded by a nucleic acid sequence of SEQ ID NO: 4.

In one embodiment, the protein transduction domain may be one or more selected from the group consisting of Hph-1, Sim-2, Tat, VP22, Antp (antennapedia), Pep-1 (peptide-1), PTD-5 (protein transduction domain-5), 7R, 9R, 11R, and CTP (cytoplasmic transduction peptide).

In one embodiment, the protein transduction domain may comprise an amino acid sequence of SEQ ID NO: 5.

In one embodiment, the protein transduction domain may be encoded by a nucleic acid sequence of SEQ ID NO: 6.

In one embodiment, the fusion protein may comprise an amino acid sequence of SEQ ID NO: 7 or 9.

In one embodiment, the fusion protein may be encoded by a nucleic acid sequence of SEQ ID NO: 8 or 10.

In one embodiment, the autoimmune disease may be one or more selected from the group consisting of systemic lupus erythematosus, rheumatoid arthritis, septic shock, allergic asthma, allergic nasitis, atopic dermatitis, ulcerative colitis, dacryoadenitis, Alzheimer's disease, stroke, arteriosclerosis, vascular restenosis, type I diabetes, type II diabetes, urticaria, conjunctivitis, psoriasis, systemic inflammatory response syndrome, polymyositis, dermatomyositis, polyarthritis nodosa, mixed connective tissue disease, Sjogren's syndrome, gout, Parkinson's disease, amyotrophic lateral sclerosis, diabetic retinopathy, multiple sclerosis, Crohn's disease, chronic thyroiditis, Celiac disease, myasthenia gravis, pemphigus vulgaris, viral diseases, bacterial diseases, radiation-induced disorders, arteriosclerosis, hemangioma, angiofibroma, reperfusion injury, and cardiac hypertrophy.

In accordance with still another aspect of the present invention, there is provided a composition for prevention or treatment of an autoimmune disease, the composition containing the fusion protein as an active ingredient.

In accordance with still another aspect of the present invention, there is provided a pharmaceutical composition for prevention or treatment of an autoimmune disease, containing, as an active ingredient, a pharmaceutically effective amount of a Smad3-PTD conjugate, a Smad3(MH1)-PTD conjugate, or a pharmaceutically acceptable salt thereof.

In accordance with still another aspect of the present invention, there is provided an expression vector comprising a nucleic acid sequence that encodes the fusion protein.

In accordance with still another aspect of the present invention, there is provided a recombinant host cell overexpressing an exogenous nucleic acid sequence that encodes the fusion protein.

In accordance with still another aspect of the present invention, there is provided a recombinant host cell transformed with the expression vector.

In one embodiment, the host cell may be a microbial cell, an animal cell, a plant cell, a cultured cell of animal origin, or a cultured cell of plant origin.

In accordance with still another aspect of the present invention, there is provided a method for producing a fusion protein, comprising the steps of: transforming a host cell with the expression vector; and culturing the host cell to express the fusion protein.

BRIEF DESCRIPTION OF THE DRAWINGS

FIG. 2A shows the structure of Smad2, and fusion proteins derived from Smad2; FIG. 2B shows the results of purification of the fusion proteins; and FIG. 2C shows the results obtained by treating Smad3 knocked-down SNU-484 cells with a SBE4 luciferase reporter plasmid and each of tSmad2, tSmad2(MH1), tSmad3, tSmad3(MH1) and mutant tSmad3(MH1) fusion proteins and measuring luciferase activity in the cells.

FIG. 3A shows the structure of Smad3, and fusion proteins derived from Smad3, and FIG. 3B shows the results of purification of the fusion proteins. FIGS. 3C and 3D show the results of analyzing the transduction of the fusion proteins into Jurkat T cells as a function of fusion protein concentration and time. FIG. 3E shows the results of analyzing the transduction of the fusion proteins into the nucleus of Hela cells. FIG. 3F shows the results of analyzing the inhibitory effects of the fusion proteins on the expression of IL-2 which is expressed by T-cell activation stimulated with anti-CD3/CD28. FIGS. 3G and 3H show experimental results indicating that the fusion proteins do not influence T-cell activation stimulated with anti-CD3/CD28 and the resulting signaling pathways. FIGS. 3I and 3J show experimental results indicating that the fusion proteins can inhibit the transcription of NFAT and NF-KB caused by T-cell activation stimulated with anti-CD3/CD28.

FIG. 4A shows the results obtained by measuring cytotoxicity at 1 hour after treating mouse splenocytes with varying concentrations of tSmad3 or tSmad3(MH1), and FIG. 4B shows the results obtained by measuring cytotoxicity at 48 hours after treating mouse splenocytes with varying concentrations of tSmad3 or tSmad3(MH1).

FIGS. 6A-6D show the results obtained by transfecting IFN-y, IL-4, IL-17A and IL-10 reporter plasmids, which have luciferase in the downstream region, and wild-type T-bet, GATA3, RORyt and Foxp3 genes, into the nucleus of HEK293T cells, and then treating the cells with the tSmad3 or tSmad3 (MH1) fusion protein, and analyzing luciferase activity in the cells. FIGS. 6E-6H show the results of analyzing the expressions of IFN-y, IL-4, IL-17A and IL-10 to determine whether or not the fusion protein tSmad3 or tSmad3(MH1) can regulate differentiation of immature T cells into each type of Th cells.

FIGS. 7A-C and FIGS. 8A-8C show the results of observing whether or not the fusion protein tSmad3(MH1) according to one embodiment of the present invention is delivered to CD4+ T cells in spleen, lymph node, thymus and kidney tissues. Specifically, FIGS. 7A and 8A show the results obtained by injecting tSmad3(MH1) intraperitoneally into C57BL/6 mice at a concentration of 200 1-Jg/mouse, isolating CD4+ T cells from each tissue at 48 hours after the injection, and analyzing tSmad3(MH1) in the isolated CD4+ T cells by flow cytometry. FIGS. 7B and 8B show the results of observation by a fluorescence microscope. FIGS. 7C and 8C show the results of hematoxylin & eosin staining of each tissue.

FIGS. 9A and 9B show the results obtained by injecting Solu-Medrol (7 mg/kg), tSmad3(MH1)-High (200 1-Jg/mouse) or tSmad3 (MH1)-Low (50 1-Jg/mouse) intraperitoneally into genetically engineered lupus nephritis mouse models three times a week during a period ranging from 13 weeks to 30 weeks after birth, and measuring the proteinuria level and survival rate of the mice. FIG. 9C shows the results of analyzing the effect of tSmad3(MH1) treatment against glomerulonephritis in 30-week-old mice. FIG. 9D shows the results of analyzing the effect of tSmad3(MH1) treatment against the formation of glomerular immune deposits by use of a confocal microscope. FIG. 9E shows the results of measuring the expressions of the inflammatory cytokines IFN-y, IL-6, IL-10 and IL-17 in serum. FIG. 9F shows the results of measuring the size of the spleens of the mice of each group. FIG. 9G shows the results of analyzing the expression levels of CD4+1FN-y+, CD4+1L-4+, CD4+1L-17A+ and CD4+Foxp3+ cells in splenocytes, isolated from the spleens of the mice of each group, by flow cytometry. FIG. 9H shows the results of analyzing the levels of anti-DNA, IgG1, IgG2a, IgG2b and IgG3 in serum.

FIGS. 10A and 10B show the results obtained by injecting Solu-Medrol (7 mg/kg), tSmad3(MH1)-High (200 1-Jg/mouse) or tSmad3(MH1)-Low (50 1-Jg/mouse) intraperitoneally into genetically engineered lupus nephritis mouse models three times a week during a period ranging from 23 weeks to 30 weeks after birth, and measuring the proteinuria level and survival rate of the mice. FIG. 10C shows the results of analyzing the effect of tSmad3(MH1) treatment against glomerulonephritis in 30-week-old mice. FIG. 10D shows the results of analyzing the effect of tSmad3(MH1) treatment against the formation of glomerular immune deposits by use of a confocal microscope. FIG. 10E shows the results of measuring the expression levels of the inflammatory cytokines IFN-y, IL-6, IL-10 and IL-17 in serum. FIG. 10F shows the results of measuring the size of the spleens of the mice of each group. FIG. 10G shows the results of analyzing the expression levels of CD4+1FN-y+, CD4+1L-4+, CD4+1L-17A+ and CD4+Foxp3+ cells in splenocytes, isolated from the spleens of the mice of each group, by flow cytometry. FIG. 10H shows the results of analyzing the levels of anti-DNA, IgG1, IgG2a, IgG2b and IgG3 in serum.

FIGS. 11A-11C show the results of analyzing the disease preventive effects of the fusion protein tSmad3(MH1) according to one embodiment of the present invention in rheumatoid arthritis animal models. Specifically, FIG. 11A shows the results obtained by injecting MTX (35 mg/kg), tSmad3(MH1) (200 1-Jg/mouse) or mutant tSmad3(MH1) (200 1-Jg/mouse) intraperitoneally into mice three times a week for 0-7 weeks after the induction of arthritis by collagen injection, and evaluating whether or not the fusion protein would exhibit a therapeutic effect by reducing arthritis score. FIG. 11B shows the results of analyzing the effect of tSmad3(MH1) treatment against foot swelling of 8-week-old mice of each group. FIGS. 11C-11E show the results of analyzing the number of splenocytes, isolated from the spleens of the mice of each group, and the expression levels of the inflammatory cytokines IFN-y and IL-17A.

FIG. 12A shows the results obtained by injecting MTX (35 mg/kg), tSmad3 (MH1) (200 1-Jg/mouse) or mutant tSmad3(MH1) (200 1-Jg/mouse) intraperitoneally into mice three times a week for 4-8 weeks after the induction of arthritis by collagen injection, and evaluating whether or not the fusion protein would exhibit a therapeutic effect by reducing arthritis score. FIG. 12B shows the results of analyzing the effects of tSmad3(MH1) treatment against inflammation cell infiltration, synovial cell proliferation and bone erosion in the knee joints of 8-week-old mice by a histopathological method. FIG. 12C shows the results of analyzing the expression levels of the inflammatory cytokines TNF-α, IL-1β and IL-6 in the knee joints of the mice by an immunohistological method. FIG. 12D shows the results of measuring the expression levels of the inflammatory cytokines IFN-y, IL-6, IL-10 and IL-17 in serum. FIG. 12E shows the results of measuring the size of the spleens of the mice of each group. FIG. 12F shows the results of analyzing the expression levels of CD4+IFN-y+, CD4+IL-4+, CD4+IL-17A+ and CD4+Foxp3+ in splenocytes, isolated from the spleens of the mice of each group, by flow cytometry.

DESCRIPTION OF SPECIFIC EMBODIMENTS

Figure 1:
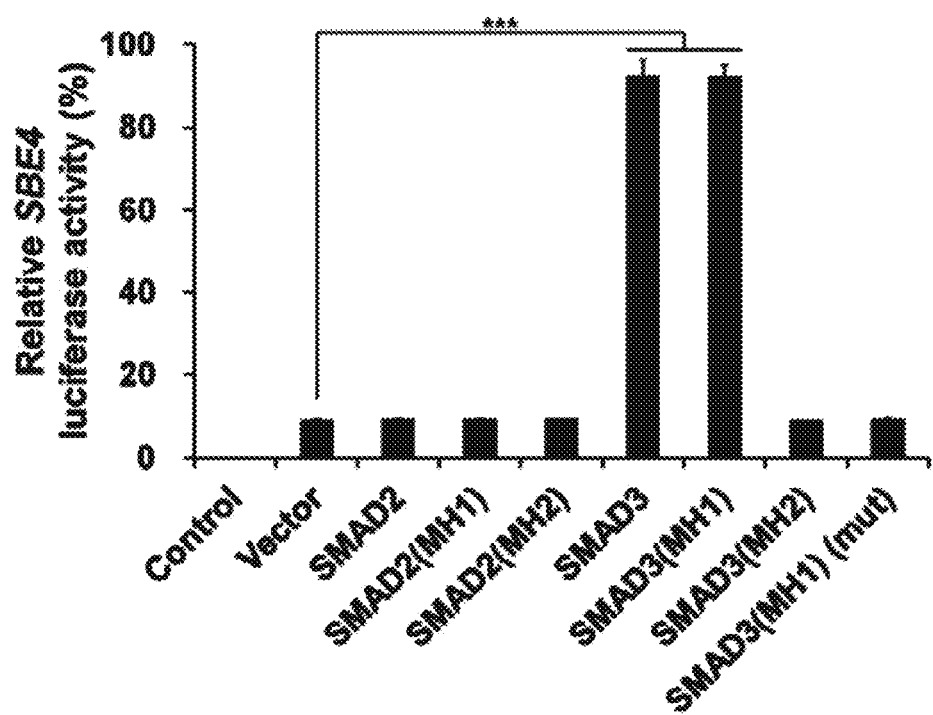
FIG. 1 shows the results of analyzing the role of a Smad3(MH1) domain in the transcriptional activation of Smad3. Smad3 knocked-down SNU-484 cells were transfected with a SBE4 (Smad binding element4) luciferase reporter plasmid and each of Smad2, Smad2(MH1), Smad2(MH2), Smad3, Smad3(MH1), Smad3(MH2), and a mutant gene of Smad3(MH1), and luciferase activity in the cells was measured.

Hereinafter, the present invention will be described with reference to the accompanying drawings. However, the present invention may be embodied in various different forms, and thus is not limited to the embodiments described herein. In the drawings, parts regardless of description are omitted to clearly describe the present invention, and like reference numerals are used to refer to like elements throughout the specification.

When a certain element "comprises" a certain component, this indicates the existence of another component without excluding in advance the possibility of existence or addition of one or more other components unless the context clearly dictates otherwise.

Unless otherwise indicated, the practice of the present invention involves conventional techniques commonly used in molecular biology, microbiology, protein purification, protein engineering, DNA sequencing, and recombinant DNA fields, all of which are within the skill of the art. Such techniques are known to those of skill in the art and are described in numerous standard texts and reference works.

Unless defined otherwise herein, all technical and scientific terms used herein have the same meaning as commonly understood by one of ordinary skill in the art to which this invention pertains.

Various scientific dictionaries that include the terms included herein are well known and available in the art. Although any methods and materials similar or equivalent to those described herein find use in the practice of the present invention, preferred methods and materials are described herein. It is to be understood that the present invention is not limited to the particular methodology, protocols, and reagents described, as these may vary, depending upon the context they are used by those of skill in the art.

As used herein, the singular terms "a," "an," and "the" include the plural reference unless the context clearly indicates otherwise. In addition, unless otherwise indicated, nucleic acids are written left to right in 5' to 3' orientation, and amino acid sequences are written left to right in amino to carboxy orientation.

Hereinafter, the present invention will be described in further detail.

In one aspect, the present invention provides a composition for prevention or treatment of an autoimmune disease, the composition containing a Smad protein or a Smad transcription modulation domain protein as an active ingredient.

In one embodiment, the Smad protein may be one or more selected from the group consisting of Smad1, Smad2, Smad3, Smad4, Smad5, Smad6, Smad7 and Smad8.

The autoimmune disease is a non-malignant disease or disorder arising from and directed against an individual's own tissues.

One of the most important characteristics in all normal individuals is that the immune system has the ability to recognize, respond to, and eliminate non-self antigens while not reacting harmfully to that of self antigenic substances. Such unresponsiveness to self-antigens is called immunologic unresponsiveness or tolerance. However, abnormalities in the induction or maintenance of self-tolerance lead to immune responses against self-antigens, resulting in the phenomenon that the immune system attacks self-tissue. Diseases caused by this process are called autoimmune diseases.

The autoimmune disease is an inflammatory disease in which antibodies against self-tissue or its components are produced. The term "autoimmune disease" refers to a group of diseases that cause chronic systemic inflammation in a number of tissues and organs.

In one embodiment, the autoimmune disease may be one or more selected from the group consisting of systemic lupus erythematosus, rheumatoid arthritis, septic shock, allergic asthma, allergic nasitis, atopic dermatitis, ulcerative colitis, dacryoadenitis, Alzheimer's disease, stroke, arteriosclerosis, vascular restenosis, type I diabetes, type II diabetes, urticaria, conjunctivitis, psoriasis, systemic inflammatory response syndrome, polymyositis, dermatomyositis, polyarthritis nodosa, mixed connective tissue disease, Sjogren's syndrome, gout, Parkinson's disease, amyotrophic lateral sclerosis, diabetic retinopathy, multiple sclerosis, Crohn's disease, chronic thyroiditis, Celiac disease, myasthenia gravis, pemphigus vulgaris, viral diseases, bacterial diseases, radiation-induced disorders, arteriosclerosis, hemangioma, angiofibroma, reperfusion injury, and cardiac hypertrophy. In addition, the autoimmune diseases may also include any diseases having the disease characteristics or developmental mechanisms of the autoimmune diseases.

As used herein, the term "prevention" refers to reducing the development of animal pathological cells, or causing damage to pathological cells, or reducing the amount of pathological cells. The prevention can be complete or partial. In this case, the term may mean that the development of pathological cells in an individual or an abnormal immune action decreases compared to the case in which the inventive composition for prevention or treatment of autoimmune diseases is not used.

As used herein, the term "treatment" refers to any clinical intervention to alter a natural process in a cell or subject to be treated. This clinical intervention may be performed during the progress of clinical pathology or to prevent the pathology. The desired treatment effects include preventing the outbreak or recurrence of a disease, or alleviating the symptoms, or reducing the direct or indirect pathological consequences induced by the disease, or preventing metastasis, or delaying the progress of the disease, or relieving or transiently alleviating the disease condition, and improving the prognosis of the disease. Namely, the term "treatment" is intended to include all the actions of ameliorate or perfectly cure symptoms of autoimmune diseases by the composition of the present invention.

The Sma and Mad related protein (Smad) is a family of evolutionarily conserved intracellular mediators that regulate the activity of particular genes as well as cell growth and proliferation. SMADs carry out their functions as part of the Transforming Growth Factor beta (TGF-β) signaling pathway, which can transmit signals from the outside of the cell to the nucleus.

TGF-β (transforming growth factor-β) superfamily includes cytokines that regulate various physiological processes such as cellular proliferation, differentiation, apoptosis, migration and development. The TGF-β superfamily includes cytokines with various functional cytokines, including TGF-βs, actins, nodals, and BMPs (bone morphometric proteins). The TGF-β family has three isoforms, TGF-β1, TGF-β2, and TGF-β3. TGF-β1 may be expressed mainly in the immune system, unlike TGF-β2 and TGF-β3.

Signaling by TGF-β1 can be initiated by type I and II receptor-mediated phosphorylation. Activated TGF-β1 receptor I can phosphorylate Smad2 and Smad3 (R-Smads) at their C terminus, which can be antagonized by inhibitory Smad6 and Smad7 (I-Smads).

Following phosphorylation, R-Smads can form complexes with Smad4 (Co-Smad), translocate to the nucleus, and activate extracellular gene transcription. R-Smads can also be phosphorylated on the linker region that bridges the N-terminal MH1 and C-terminal MH2 domains. BMPs utilize a specific intracellular signaling cascade to target genes via R-SmadS (Smad1, 5, 8), Co-Smad (Smad4) and I-SmadS (Smad6, 7).

Smad7 is a known intracellular antagonist of TGF-β signaling, which inhibits TGF-β-induced transcriptional responses, whereas SMAD6 is a known inhibitor of TGF-β and BMP (bone morphogenetic protein, a member of the TGF-β super family).

Namely, the Smad protein is part of the Transforming Growth Factor beta (TGF-β) signaling pathway, and inflammatory responses by the imbalance of Th cells can be inhibited by controlling the signaling pathway.

Particularly, the present inventors have found that a novel fusion protein comprising Smad3 or a Smad3 transcription modulation domain protein and a protein transduction domain can inhibit the function of the inflammatory cells Th1, Th2 and Th17 cells to inhibit differentiation thereof, and can induce the function of regulatory T (Treg) cells (which regulate the inflammatory cells) to promote differentiation thereof, thereby exhibiting preventive and therapeutic effects against autoimmune diseases including lupus nephritis and rheumatoid arthritis.

Figure 2A:
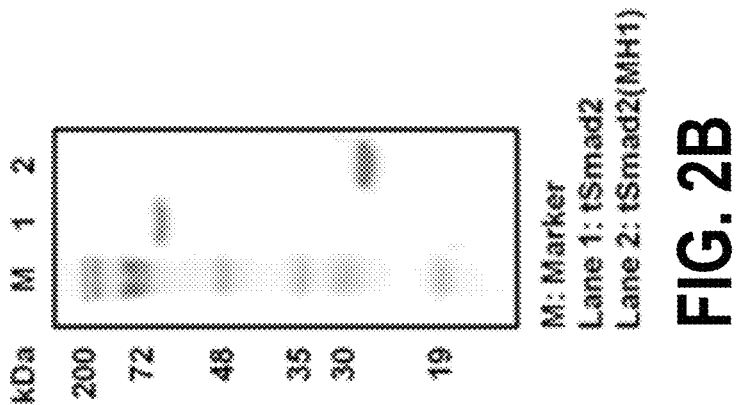
FIGS. 2A-2C show the results of analyzing the functional difference between the fusion proteins tSmad2 and tSmad3 according to one embodiment of the present invention. Specifically.
Figure 2B:
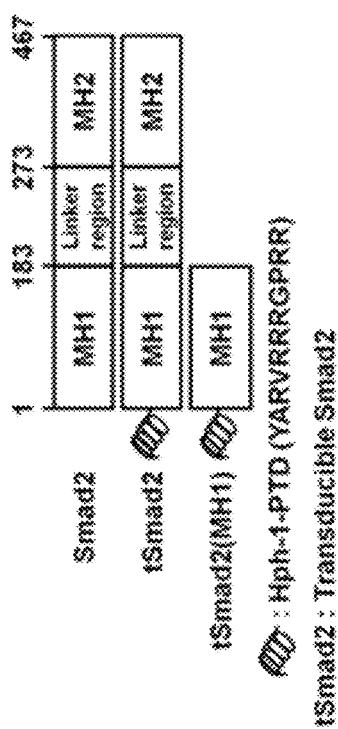
Figure 2C:
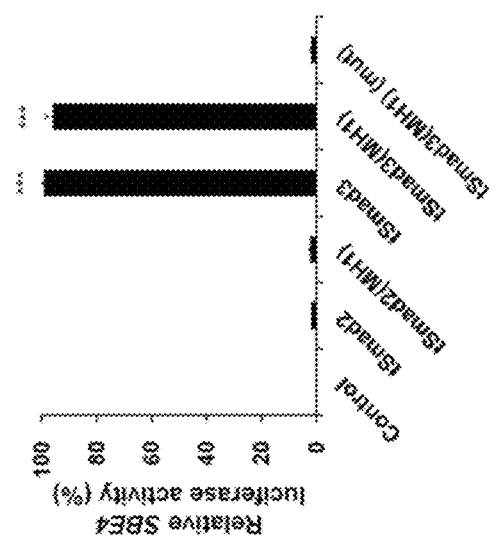

In addition, the composition of the present invention may contain a Smad3 protein or a Smad3 transcription modulation domain protein as an active ingredient. The transcription modulation domain is a Smad transcription modulation domain (MH1) that is important in the transcriptional activation of Smad3, and it may comprise a DNA binding domain. Namely, the Smad protein can bind to the promoter of a target gene via the transcription modulation domain rather than the full-length protein, and can perform the same transcription modulation function (FIGS. 1 and 2).

In one embodiment, the Smad3 protein may comprise an amino acid sequence of SEQ ID NO: 1, and the Smad3 transcription modulation domain protein may comprise an amino acid sequence of SEQ ID NO: 3. Furthermore, the Smad3 protein may be encoded by a nucleic acid sequence of SEQ ID NO: 2, and the Smad3 transcription modulation domain protein may be encoded by a nucleic acid sequence of SEQ ID NO: 4.

In accordance with another aspect of the present invention, there is provided a fusion protein for prevention or treatment of an autoimmune disease, the fusion protein comprising: a Smad protein or a Smad transcription modulation domain protein; and a protein transduction domain.

Because the fusion protein comprises the protein transduction domain, it can easily transport the Smad protein or the Smad transcription modulation domain protein into the nucleus, and the transcription modulation effect thereof can be significantly improved.

The protein transduction domain (PTD) is a short peptide having strong hydrophobicity, and which can effectively transport physiologically active molecules such as proteins, DNA and RNA, fused therewith, into cells, and a variety of protein transduction domains are known in the art. Because the protein transduction domain can transport a physiologically active domain not only into the cytoplasm but also into the nucleus, it can effectively deliver the Smad protein into the nuclei.

Namely, the cellular membrane can prevent macromolecules from entering cells. For nearly all therapeutics according to the prior art, at least one cellular membrane must be traversed. Traditional small molecule pharmaceutical development relies on the chance discovery of membrane permeable molecules having the ability to modulate protein function. Namely, although small molecules remain the dominant therapeutic paradigm, many of these molecules suffer from lack of target specificity, or can cause side effects and toxicity.

However, macromolecules such as proteins, which have functions far superior to those of small molecules, can be created using rational drug design based on molecular, cellular, and structural data. However, the cellular membrane is impermeable to most molecules.

Thus, the protein drug may be linked to the protein transduction domain so that it can cross the cell membrane. The use of the protein transduction domain capable of transporting effector molecules into cells has become increasingly attractive in the design of drugs as they promote the cellular uptake of cargo molecules.

The protein transduction domain, generally categorized as amphipathic (meaning having both a polar and a nonpolar end) or cationic (meaning of or relating to containing net positively charged atoms) depending on its sequence, provides a non-invasive delivery technology for macromolecules, and this domain is often referred to as "Trojan peptide", "membrane translocating sequence", or "cell permeable protein" (CPP). The protein transduction domain enables the Smad protein or the Smad transcription modulation domain protein to penetrate cell membranes, and thus can exhibit sufficient effects on the inhibition of transcription of NFAT, NF-κB, IFN-γ, IL-4 and IL-17A, the inhibition of secretion of inflammatory cytokines, and the inhibition of differentiation of inflammatory cells.

The protein transduction domain was first reported based on the finding that when HIV TAT protein is added to a cell culture medium, the protein is introduced into cells (Green et al., 1988, Frankel et al., 1988). Since then, *Drosophila* Antennapedia(Antp) homeotic transcription factor, Joliot et al., 1991) and herpessimplex-virus-1 DNA binding protein VP22 (Elliot et al., 1997), which have the ability to enter cells via the cell membrane, were also identified. It is known that a number of protein transduction domains known to date are cationic in nature, and interact with anionic DNAs to promote endocytosis and transport DNAs into cells to thereby increase the gene transduction efficiency (Grafton J. P., Nature Medicine. 9(3), 357-362, 2003). In addition, a variety of improved protein transduction domains have been developed.

In one embodiment, the protein transduction domain may be one or more selected from the group consisting of Hph-1, Sim-2, Tat, VP22, Antp (antennapedia), Pep-1 (peptide-1), PTD-5 (protein transduction domain-5), 7R, 9R, 11R and CTP (cytoplasmic transduction peptide). In addition, the protein transduction domain may also be any protein transduction domain that is widely known in the art or can promote the penetration of a certain molecule into the cell membrane.

In one embodiment, the protein transduction domain may comprise an amino acid sequence of SEQ ID NO: 5, and may be encoded by a nucleic acid sequence of SEQ ID NO: 6.

In addition, the fusion protein may comprise an amino acid sequence of SEQ ID NO: 7 or 9, and may be encoded by a nucleic acid sequence of SEQ ID NO: 8 or 10.

In accordance with still another aspect of the present invention, there is provided a composition for prevention or treatment of an autoimmune disease, the composition containing the fusion protein as an active ingredient.

Namely, because the fusion protein has the protein transduction domain bound thereto, it has an excellent ability to penetrate the cell membrane, and can be easily introduced into the nuclei. Accordingly, the fusion protein can effectively regulate the expression of various genes by its interaction with other transcription factors.

Particularly, because the fusion protein comprises the Smad protein or its transcription modulation domain, it can inhibit the transcription or activity of NFAT, NF-κB, IFN-γ, IL-4 and IL-17A, can control the function of inflammatory Th1, Th2 and Th17 cells to inhibit differentiation thereof, and can induce the function of Treg cells (which regulate inflammatory cells) to promote differentiation thereof, thereby exhibiting preventive and therapeutic effects against autoimmune diseases, including lupus nephritis and rheumatoid arthritis.

In accordance with still another aspect of the present invention, there is provided a pharmaceutical composition for prevention or treatment of an autoimmune disease, the pharmaceutical composition containing, as an active ingredient, a pharmaceutically effective amount of a Smad3-PTD conjugate, a Smad3(MH1)-PTD conjugate, or a pharmaceutically acceptable salt thereof.

The pharmaceutical composition for prevention or treatment of the autoimmune disease may be administered orally or parenterally. For example, the pharmaceutical composition for prevention or treatment of the autoimmune disease may be administered systemically or topically. Examples of such route of administration include oral administration and parenteral administration.

The pharmaceutical composition for prevention or treatment of the autoimmune disease may be formulated with a suitable amount of a pharmaceutically acceptable vehicle or carrier so as to provide a suitable dosage form. Thus, the pharmaceutical composition for prevention or treatment of the autoimmune disease may further contain carriers, excipients and diluents that are used in the preparation of pharmaceutical compositions.

Examples of the carriers, excipients and diluents that may be used in the present invention include, but are not limited to, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil.

For use, the composition may be formulated as oral preparations such as powders, granules, tablets, capsules, suspensions, emulsions, syrups or aerosols, preparations for external use, suppositories or sterile injectable solutions.

Solid formulations for oral administration include tablets, pills, powders, granules, capsules and the like. Such solid formulations can be prepared by mixing at least one the Smad3-PTD conjugate and the Smad3 (MH1)-PTD conjugate with at least one excipient, for example, starch, calcium carbonate, sucrose, lactose or gelatin. In addition to the excipient, a lubricant such as magnesium stearate or talc may also be used.

Liquid formulations for oral administration include suspensions, solutions, emulsions, and syrup, and may contain various excipients, for example, wetting agents, flavoring agents, aromatics and preservatives, in addition to water and liquid paraffin, which are simple diluents.

Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, etc., can be used. As the base of the suppositories, witepsol, Macrogol, Tween 61, cacao butter, laurin fat, glycerogelatin, etc., can be used.

In accordance with still another aspect of the present invention, there is provided an expression vector comprising a nucleic acid sequence that encodes the fusion protein.

As used herein, the term "vector" refers to a nucleic acid molecule capable of transporting another nucleic acid to which it has been linked. Examples of the vector include, but are not limited to, bacteria, plasmids, phages, cosmids, episomes, viruses, and insertable DNA fragments (fragments able to be inserted into a host cell genome by homologous recombination). One type of vector is a "plasmid", which refers to a circular double stranded DNA loop into which additional DNA segments may be ligated. Another type of vector is a viral vector, wherein additional DNA segments may be ligated into the viral genome.

The term "expression vector" refers to a vector that can direct the expression of a gene encoding a target protein operably linked thereto. Usually, expression vectors suitable for DNA recombination techniques are of the plasmid type. Thus, "plasmid" and "vector" can be used interchangeably. However, the present invention is also intended to comprise other types of expression vectors, such as viral vectors which fulfill similar functions.

Examples of expression vectors that may be used in the present invention include, but are not limited to, pET-3a-d, pET-9a-d, pET-11a-d, pET-12a-c, pET-14b, pET-15b, pET-16b, pET-17b, pET-17xb, pET-19b, pET-20b(+), pET-21a-d (+), pET-22b(+), pET-23a-d(+), pET-24a-d(+), pET-25b(+), pET-26b(+), pET-27b(+), pET-28a-c(+), pET-29a-c(+), pET-30a-c(+), pET-30 Ek/LIC, pET-30 Xa/LIC, pET-31b(+), pET-32a-c(+), pET-32 Ek/LIC, pET-32 Xa/LIC, pET-33b (+), pET-34b(+), pET-35b(+), pET-36b(+), pET-37b(+), pET-38b(+), pET-39b(+), pET-40b(+), pET-41a-c(+), pET-41 Ek/LIC, pET-42a-c(+), pET-43.1a-c(+), pET-43.1 Ek/LIC, pET-44a-c(+), pRSETA, pRSETB, pRSETC, pESC-HIS, pESC-LEU, pESC-TRP, pESC-URA, Gateway pYES-DEST52, pAO815, pGAPZ A, pGAPZ B, pGAPZ C, pGAPα A, pGAPα B, pGAPα C, pPIC3.5K, pPIC6 A, pPIC6 B, pPIC6 C, pPIC6α A, pPIC6α B, pPIC6α C, pPIC9K, pYC2/CT, pYD1 Yeast Display Vector, pYES2, pYES2/CT, pYES2/NT A, pYES2/NT B, pYES2/NT C, pYES2/CT, pYES2.1, pYES-DEST52, pTEF1/Zeo, pFLD1, PichiaPink™, p427-TEF, p417-CYC, pGAL-MF, p427-TEF, p417-CYC, PTEF-MF, pBY011, pSGP47, pSGP46, pSGP36, pSGP40, ZM552, pAG303GAL-ccdB, pAG414GALccdB, pAS404, pBridge, pGAD-GH, pGAD T7, pGBK T7, pHIS-2, pOBD2, pRS408, pRS410, pRS418, pRS420, pRS428, yeast micron A form, pRS403, pRS404, pRS405, pRS406, pYJ403, pYJ404, pYJ405 and pYJ406.

Meanwhile, the expression vector may be introduced into a host cell, and the host cells transformed with the introduced vector can produce the fusion protein. Herein, the vector may contain a promoter that is recognized by the host organism.

The promoter may be selected from the group consisting of SBE4, 3TP, PAI-1, p15, p21, CAGA12, hINS, A3, NFAT, NFKB, AP1, IFNG, IL4, IL17A, IL10, GPD, TEF, ADH, CYC, INU1, PGK1, PHO5, TRP1, GAL1, GAL10, GUT2, tac, T7, T5, nmt, fbpl, AOX1, AOX2, MOX1 and FMD1 promoters, but may vary depending on various factors, including host cells or expression conditions.

The nucleic acid that encodes the fusion protein may be operably linked to the promoter sequence. As used herein, the term "operably linked" means that one nucleic acid fragment is linked to other nucleic acid fragment so that the function or expression thereof is affected by the other nucleic acid fragment. Namely, the gene that encodes the fusion protein can be linked such that the expression thereof can be regulated by the promoter present in the vector.

Meanwhile, the expression vector may further comprise additional control sequences. The control sequences may be the Shine-Dalgano sequence of replicase gene of phage MS-2 and the Shine-Dalgano sequence of c II of bacteriophage lambda, but are not limited thereto.

In addition, the expression vector may comprise an appropriate marker to select transformed host cells. The marker gene may be an antibiotic resistance gene or a fluorescent protein gene. The antibiotic resistance gene may be selected from the group consisting of hygromycin resistance genes, kanamycin resistance genes, chloramphenicol resistance genes and tetracycline resistance genes, but is not limited thereto. The fluorescent protein gene may be selected from the group consisting of yeast-enhanced green fluorescent protein (yEGFP) gene, green fluorescent protein (GFP) gene, blue fluorescent protein (BFP) gene, and red fluorescent protein (RFP) gene, but is not limited thereto.

In accordance with still another aspect of the present invention, there is provided a recombinant host cell overexpressing an exogenous nucleic acid sequence that encodes the fusion protein, and there is provided a recombinant host cell transformed with the expression vector.

The host cell can be metabolically engineered by transformation. The host cell refers to a cell which is easily transformed with an expression vector, and may be any cell that may be transformed by a genetic engineering method so as to efficiently express a specific gene.

In one embodiment, the host cell may be a microbial cell, an animal cell, a plant cell, a cultured cell of animal origin, or a cultured cell of plant origin, but is not limited thereto. Preferably, the host cell may be a naturally occurring or wild-type host cell or an altered host cell. The wild-type host cell may be a host cell that has not been genetically altered using a recombinant method.

As used herein, the term "metabolically engineered" or "metabolic engineering" involves rational pathway design and assembly of biosynthetic genes, genes associated with operons, and control elements for such nucleic acid sequences, for the production of a desired metabolite, such as alcohol or protein, in a microorganism.

"Metabolically engineered" can further include optimization of metabolic flux by regulation and optimization of transcription, translation, protein stability and protein functionality using genetic engineering and appropriate culture conditions. The biosynthetic genes can be heterologous to the host (e.g., microorganism), either by virtue of being foreign to the host, or being modified by mutagenesis, recombination, or association with a heterologous expression control sequence in an endogenous host cell. Appropriate culture conditions include conditions such as culture medium pH, ionic strength, nutritive content, etc., temperature, oxygen, carbon dioxide, nitrogen content, humidity, and other culture conditions that permit production of a compound by the host microorganism, i.e., by the metabolic action of the microorganism. Appropriate culture conditions are well known for microorganisms that can serve as host cells.

Accordingly, the metabolically "engineered" or "modified" microorganism can be produced by introducing genetic material into a host or parental microorganism of choice to thereby modify or alter the cellular physiology and biochemistry of the microorganism. Through the introduction of genetic material, the parental microorganism can acquire new properties, e.g. the ability to produce a new, or greater quantities of, an intracellular metabolite.

For example, the introduction of genetic material into a parental microorganism can result in a new or modified ability to produce a chemical substance. The genetic material introduced into the parental microorganism contains gene, or parts of genes, coding for one or more of the enzymes involved in a biosynthetic pathway for the production of a chemical, and may also include additional elements for the expression or regulation of expression of these genes, for example, promoter sequences.

As used herein, the term "altered host cell" refers to a genetically engineered host cell wherein a gene is expressed at an altered level of expression compared to the level of expression of the same gene in an unaltered or wild-type host cell grown under essentially the same growth conditions. In an embodiment, an altered host cell is one in which the gene is expressed or produced at a level of expression or production that is higher than the level of expression or production of gene in the unaltered or wild-type host cell grown under essentially the same growth conditions. A "modified host cell" herein refers to a wild-type or altered host cell that has been genetically engineered to overexpress a gene encoding a target protein. The modified host cell is capable of expressing the target protein at a greater level than its wild-type or altered parent host cell.

As used herein, the term "transformation" refers to a method of delivering the vector into a microorganism. If a cell to be transformed is a prokaryotic cell, the transformation may be performed by a $CaCl_2$ method (Cohen, S. N. et al., Proc. Natl. Acac. Sci. USA, 9:2110-2114(1973)), a Hanahan method (Cohen, S. N. et al., Proc. Natl. Acad. Sci. USA, 9:2110-2114(1973); and Hanahan, D., J. Mol. Biol., 166:557-580(1983)) or an electroporation method (Dower, W. J. et al., Nucleic. Acids Res., 16:6127-6145(1988)).

If a cell to be transformed is an eukaryotic cell, the transformation may be performed by microinjection (Capecchi, M. R., Cell, 22:479(1980)), calcium phosphate precipitation (Graham, F. L. et al., Virology, 52:456(1973)), electroporation (Neumann, E. et al., EMBO J., 1:841(1982)), liposome-mediated transfection (Wong, T. K. et al., Gene, 10:87(1980)), DEAE-dextran treatment (Gopal, Mol. Cell. Biol., 5:1188-1190(1985)), or gene bombardment (Yang et al., Proc. Natl. Acad. Sci., 87:9568-9572(1990)), but is not limited thereto.

For fungi such as yeast, the transformation may generally be performed using a lithium acetate method (R. D. Gietz, Yeast 11, 355360 (1995)), a heat-shock method (Keisuke Matsuura, Journal of Bioscience and Bioengineering, Vol.

100, 5; 538-66-29 544 (2005)), or an electroporation method (Nina Skolucka Asian, Pacific Journal of Tropical Biomedicine, 94-98 (2011)), but is not limited thereto.

In accordance with still another aspect of the present invention, there is provided a method for producing a fusion protein, comprising the steps of: transforming a host cell with the expression vector; and culturing the host cell to express the fusion protein.

The transformed host cell may be cultured under batch, fed-batch or continuous culture conditions. Because the host cell can express the fusion protein as a result of the transformation, the fusion protein can be recovered from the cultured host cell.

Classical batch fermentation methods may use a closed system. In this case, the culture medium is made prior to the beginning of the fermentation run, the medium is inoculated with a desired organism, and fermentation occurs without addition of any components to the medium. In certain cases, the pH and oxygen content of the growth medium, rather than the carbon source content, may be altered during a batch process. The metabolites and cell biomass of the batch system may change constantly up to the time when the fermentation is stopped. In the batch system, cells can usually progress through a static lag phase to a high growth log phase and finally to a stationary phase where growth rate is diminished or halted. Generally, the cells can produce the most protein in the log phase.

A variation on the standard batch fermentation is a "fed-batch fermentation" system. In the system, nutrients (e.g., carbon source, nitrogen source, $O_2$, and typically, other nutrients) may be added when their concentration in culture falls below a threshold. Fed-batch systems are useful when catabolite inhibition is apt to inhibit the metabolism of the cells and when it is desirable to have limited amounts of nutrients in the medium. Actual nutrient concentration in fed-batch systems can be estimated on the basis of the changes of measurable factors such as pH, dissolved oxygen and the partial pressure of waste gases such as $CO_2$. Batch and fed-batch fermentations are general systems well known in the art.

Continuous fermentation employs an open system in which a defined culture medium is added continuously to a bioreactor and an equal amount of conditioned medium is removed simultaneously for processing. Continuous fermentation generally maintains the cultures at a constant high density where cells are primarily in log-phase growth. Continuous fermentation allows for the modulation of one factor or any number of factors that affect cell growth and/or end product concentration.

For example, a limiting nutrient such as a carbon source or a nitrogen source may be maintained at a fixed rate and all other parameters may be suitably maintained. In other systems, a number of factors affecting growth are altered continuously while the cell concentration, measured by medium turbidity, is kept constant. Continuous systems strive to maintain steady state growth conditions. Thus, cell loss due to medium being drawn off may be balanced against the cell growth rate in the fermentation. Methods of maintaining nutrients and growth factors for continuous fermentation processes as well as techniques for maximizing the rate of product formation are known to those of skill in the art.

Any person skilled in the art to which the present invention pertains can modify the kind of each component, the amount of component added, etc., based on the disclosure of the present invention. If these modifications show the same technical effects as those before modification, these modifications will fall within the technical scope of the present invention.

Hereinafter, the present invention will be described in detail with reference to examples, but the scope of the present invention is not limited to these examples.

Experimental Example 1: Examination of the Role of Smad3 (MH1) Domain in Transcriptional Activation In order to examine whether or not the Smad3 (MH1) domain plays an important role in the transcriptional activation of Smad3, Smad3 knocked-down SNU-484 cells were transfected with a SBE4 (Smad binding element 4) luciferase reporter plasmid and each of Smad2, Smad2 (MH1), Smad2(MH2), Smad3, Smad3(MH1), Smad3 (MH2) and a mutant gene of Smad3(MH1), and luciferase activity in the cells was analyzed.

In addition, SNU-484 cells were treated with a SBE4 luciferase reporter plasmid and each of the recombinant fusion proteins tSmad2, tSmad2(MH1), tSmad3, tSmad3 (MH1) and mutant tSmad3(MH1), and luciferase activity in the cells was analyzed.

As a result, it could be seen that Smad2 did not influence the activity of SBE4 luciferase, because 30 amino acid residues in the Smad2(MH1) domain were located immediately before the DNA-binding β-hairpin so that Smad2 cannot bind to a target gene. However, the Smad3(MH1) domain sufficiently activated the transcription of Smad3 (FIGS. 1 and 2).

Experimental Example 2: Construction of Fusion Protein Comprising Smad Transcription Modulation Domain and Protein Transduction Domain The protein transduction domain (PTD) Hph-1 (SEQ ID NO: 6) and the transcription modulation domain Smad3 (MH1) (SEQ ID NO: 4) of Smad3 (SEQ ID NO: 2) were cloned into a pET-28a(+) vector (Novagen) to thereby construct the recombinant fusion DNAs tSmad3 (SEQ ID NO: 8) and tSmad3(MH1) (SEQ ID NO: 10). Each of the recombinant fusion DNAs was transformed into a BL21 CodonPlus(DE3)-RIPL *E. coli.* strain (Invitrogen). The transformed strain was cultured, and 1 mM IPTG (isopropyl-β-D-thiogalactopyranoside; Duchefa) was added thereto, followed by inducing the expression of the protein in the cells at 37° C. for 5 hours. Then, the cells were isolated, lysed with lysis buffer (10 mM imidazole, 50 mM $NaH_2PO_4$, 300 mM NaCl, pH 8.0), and then disrupted by a homogenizer. The fusion protein was bound to Ni-NTA beads (Qiagen) via six histidine residues artificially linked to the terminal end of the protein.

The protein was loaded onto HisTrap chromatography columns (Bio-Rad) and sufficiently washed with washing buffer (30 mM imidazole, 50 mM $NaH_2PO_4$, 300 mM NaCl, pH 8.0). Then, the protein was eluted with elution buffer (250 mM imidazole, 50 mM $NaH_2PO_4$, 300 mM NaCl, pH 8.0).

Using PD-10 Sephadex G-25 (GE Healthcare), buffer was replaced with 10% glycerol-containing PBS to remove imidazole and NaCl. Using SP beads (SP Sepharose™ Fast Flow, GE Healthcare), endotoxins such as LPS were removed from the obtained protein.

Figure 3A:
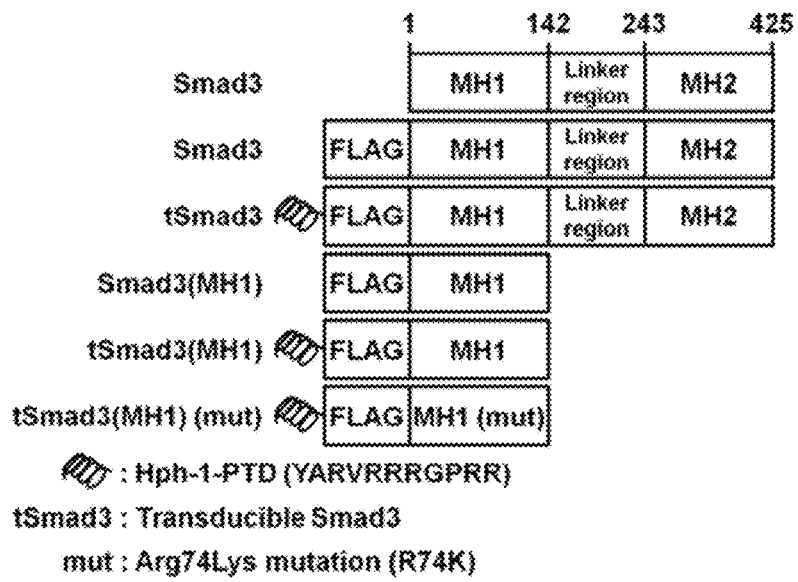
FIGS. 3A-3J show the results of analyzing the inhibitory effect of the fusion protein tSmad3(MH1) according to one embodiment of the present invention against the expression of IL-2 which is expressed by T-cell activation stimulated with anti-CD3/CD28. Specifically.
Figure 3B:
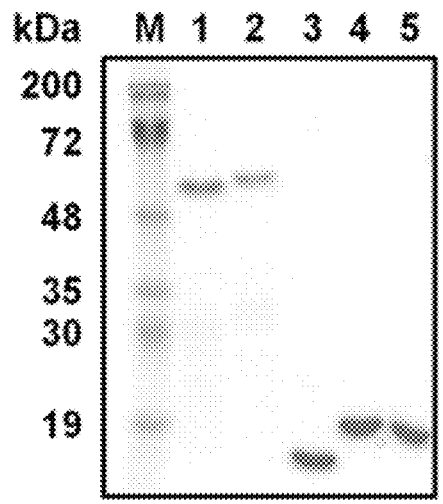

The resulting protein was bound using binding buffer (50 mM $NaH_2PO_4$, 300 mM NaCl, pH 6.0), and then loaded onto a column and eluted with elution buffer (50 mM NaH$_2$PO$_4$, 2 M NaCl, pH 6.0). Finally, NaCl was removed using PD-10 Sephadex G-25, and the buffer was replaced with 10% glycerol-containing PBS, after which the resulting protein (SEQ ID NO: 5, recombinant fusion protein) was stored at −80° C. until use in experiments (FIGS. 2, 3a and 3b).

Experimental Example 3: Analysis of Intracellular Transduction of tSmad3 and tSmad3(MH1) Recombinant Fusion Proteins 3-1: Analysis of Intracellular Transduction by Western Blotting Jurkat T cells were incubated with varying concentrations (0, 0.1, 0.5, 1, 2 and 5 μM) of each of tSmad3 and tSmad3(MH1) recombinant fusion proteins of Example 2 for varying times (0, 1, 2, 4, 6, 12, 24 and 48 h), and whether or not the protein was delivered into the cells was analyzed by Western blotting.

Figure 3C:
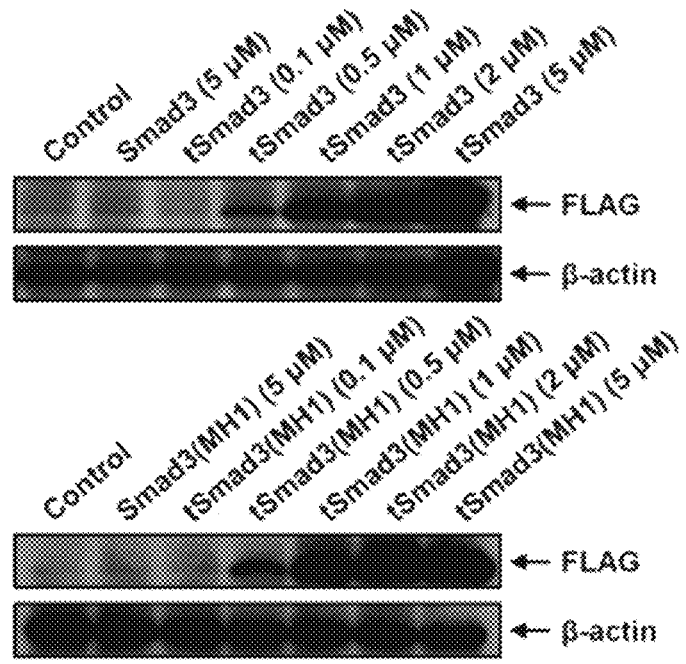
Figure 3D:
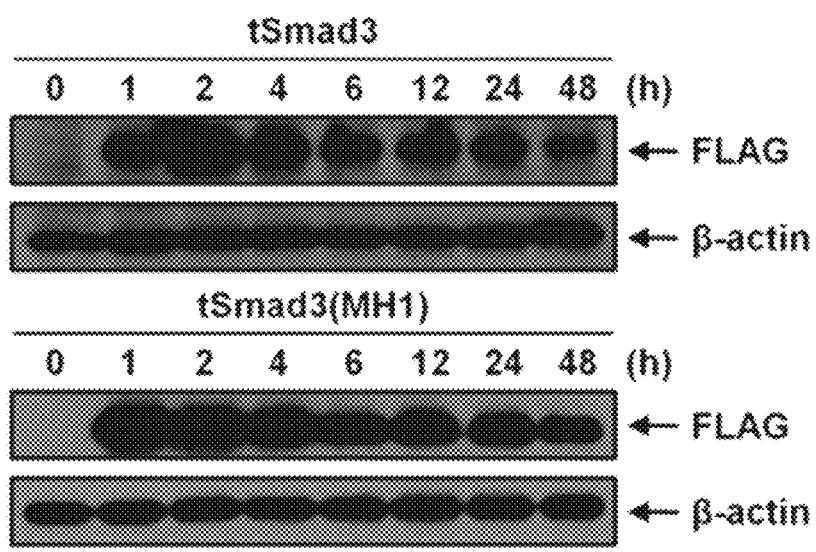

As a result, it was shown that each of the tSmad3 and tSmad3(MH1) fusion proteins was delivered in proportion to the concentration thereof and was continuously delivered even after 48 hours while the protein in the cell culture maintained its structure (see FIGS. 3c and 3d).

3-2: Analysis of Whether or not Fusion Protein is Delivered to Nucleus of Cells, by Use of Antibody 5 μM of each of the tSmad3 and tSmad3(MH1) recombinant proteins was incubated with HeLa cells for 1 hour and washed with PBS, after which the cells were treated with 0.2% Triton X-100 (Sigma-Aldrich) to form an opening in the cells. A fluorescence-labeled antibody was bound to the recombinant fusion protein through the opening. Next, the nucleus of the cells was stained with DAPI dye (Invitrogen), and then the location of fluorescence was determined by a fluorescence microscope to thereby determine the location to which the recombinant fusion protein was delivered.

Figure 3E:
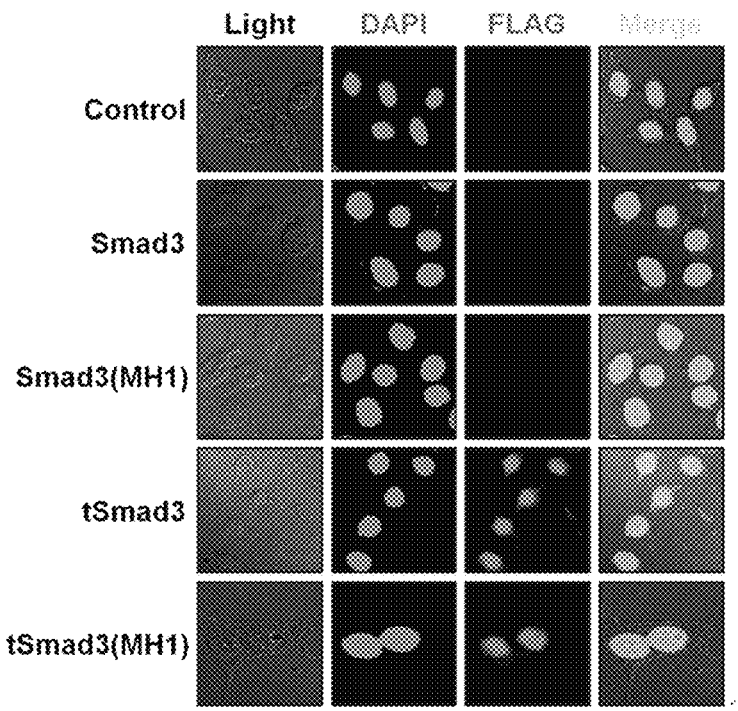

As a result, it was shown that the tSmad3 and tSmad3(MH1) fusion proteins were effectively delivered to the nucleus of the cells (FIG. 3e).

Experimental Example 4: Analysis of Cytotoxicity of tSmad3 and tSmad3(MH1) Recombinant Fusion Proteins In order to confirm that the protein obtained from the *E. coli* strain by expression is completely free of LPS so that it is not cytotoxic, a cytotoxicity test was performed. Varying concentrations of the protein were transfected into mouse splenocytes, and then the cells were incubated with WST-8, a substrate that develops color by dehydrogenase present in living cells.

Figure 4A:
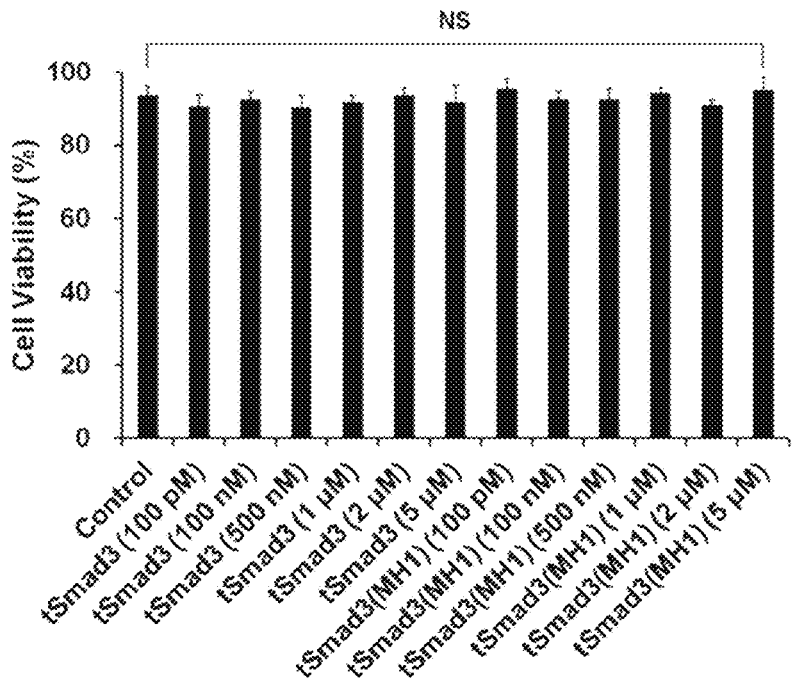
FIGS. 4A and 4B show the results of measuring the cytotoxicity of the fusion protein tSmad3(MH1) according to one embodiment of the present invention in mouse splenocytes. Specifically.
Figure 4B:
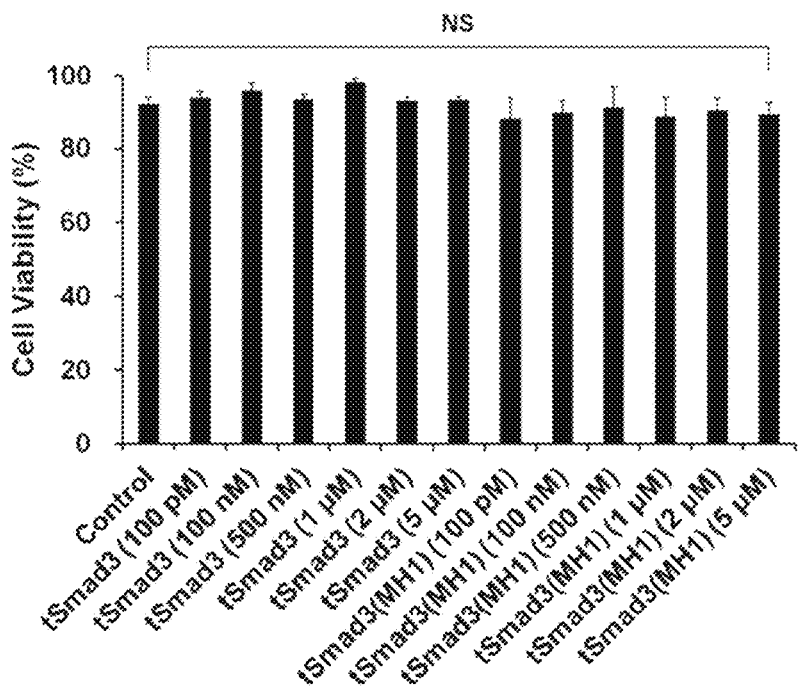
Figure 5A:
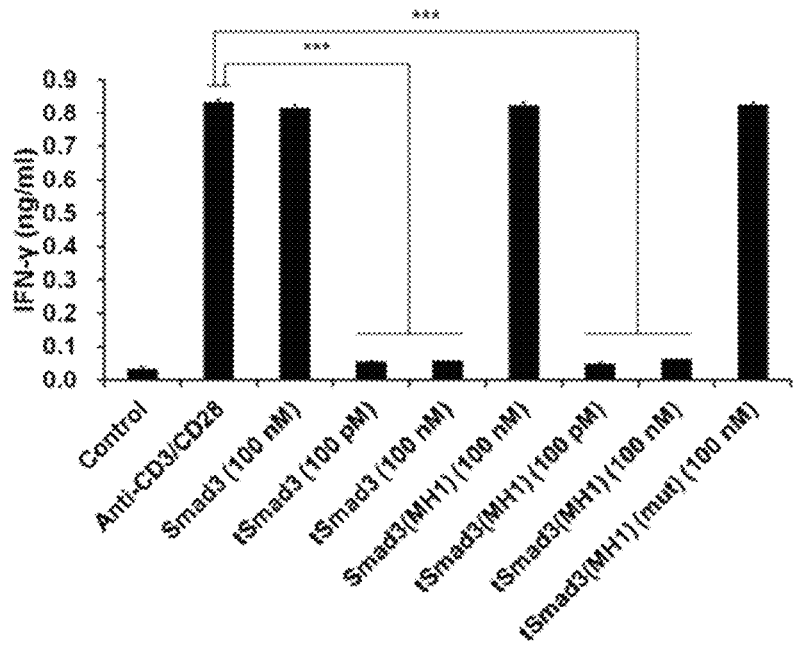
FIGS. 5A-5D show the modulation effects of the fusion protein tSmad3(MH1) according to one embodiment of the present invention against the expression of IFN-y, IL-4, IL-17A and IL-10, which are expressed by T-cell activation stimulated with anti-CD3/CD28.
Figure 5B:
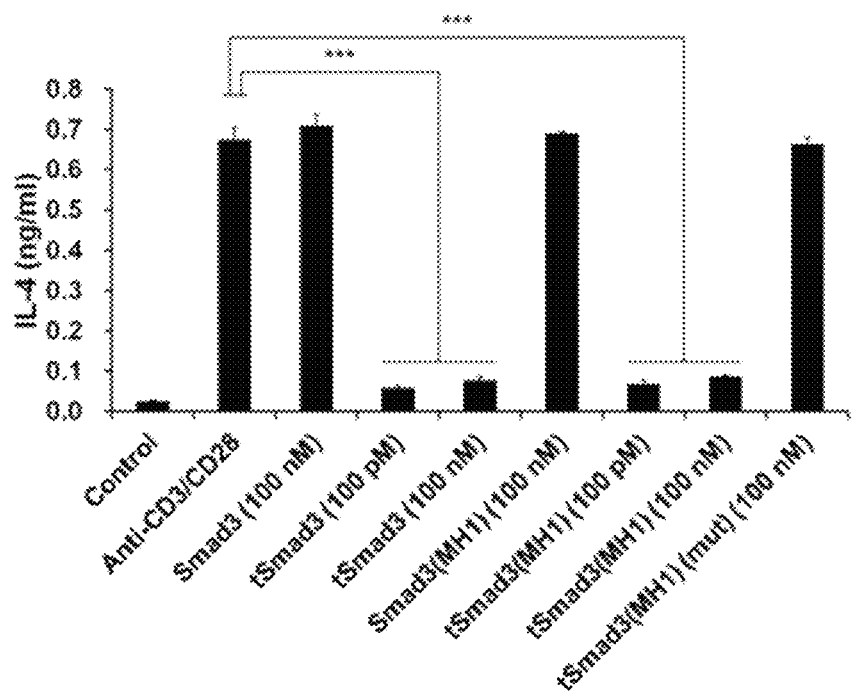
Figure 5C:
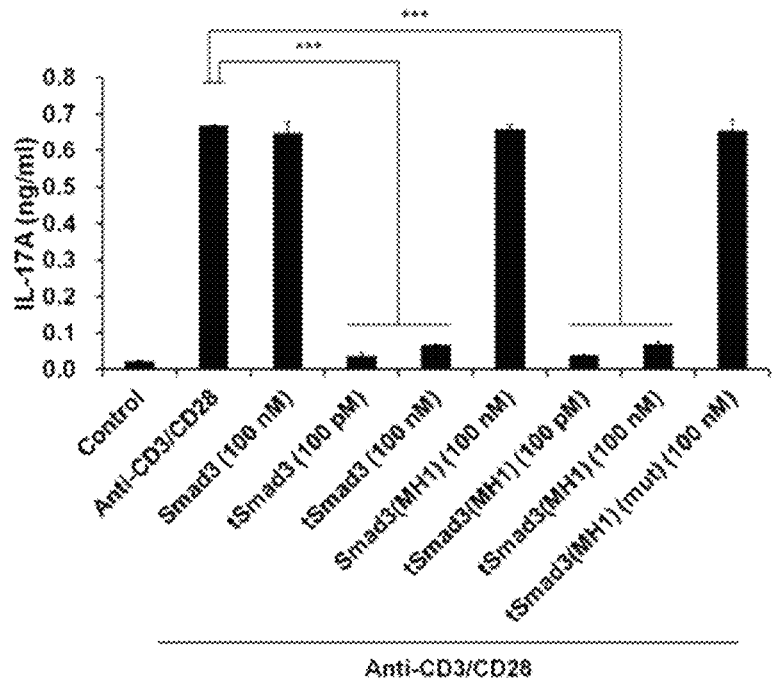
Figure 5D:
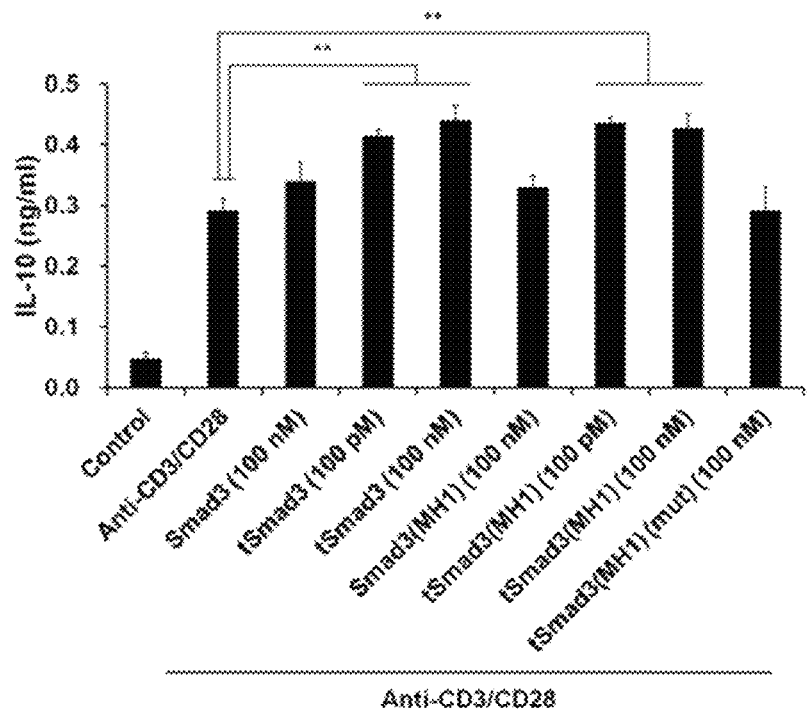
Figure 6A:
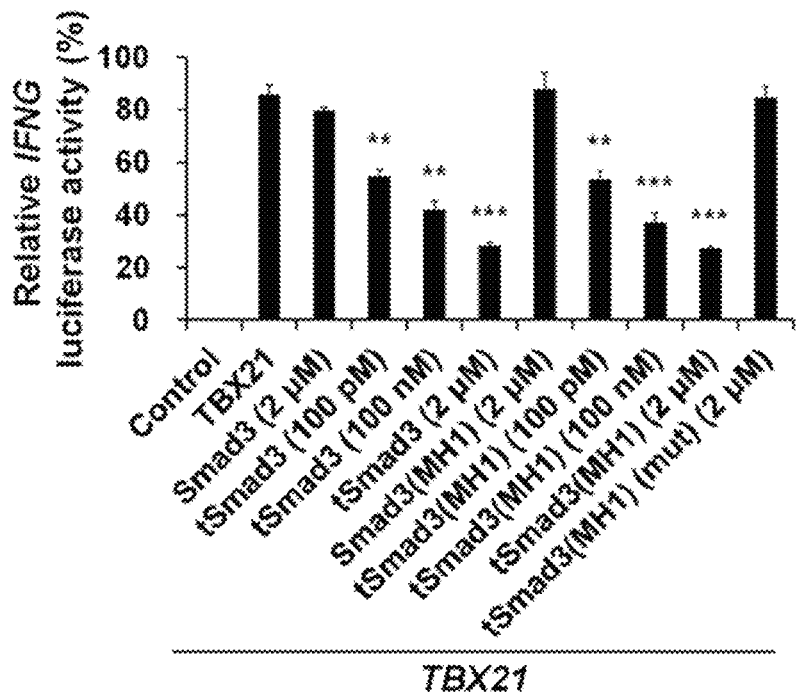
FIGS. 6A-6H show the transcription modulation effect of the fusion protein tSmad3(MH1) according to one embodiment of the present invention and the effect of the fusion protein on the regulation of differentiation of immature T cells into each type of Th cells. Specifically.
Figure 6B:
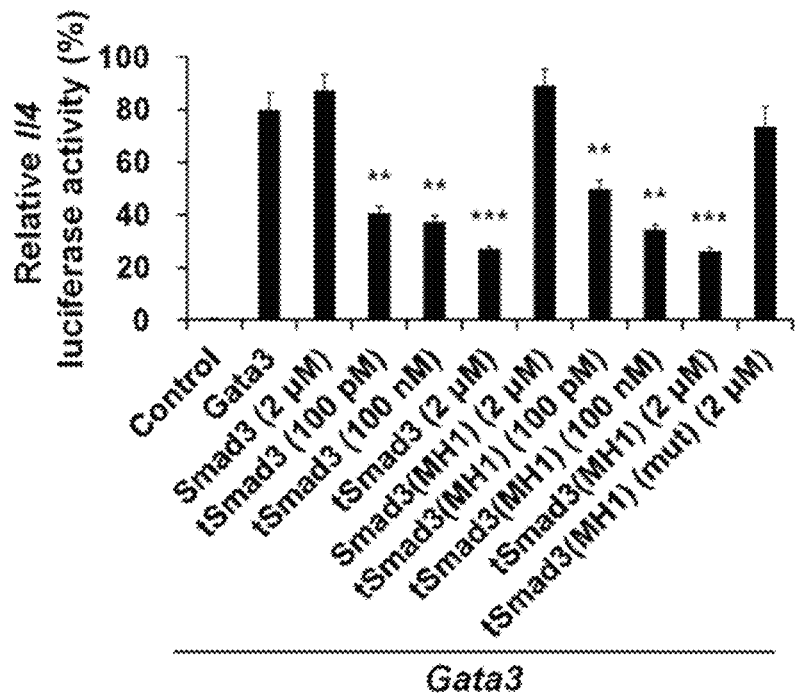
Figure 6C:
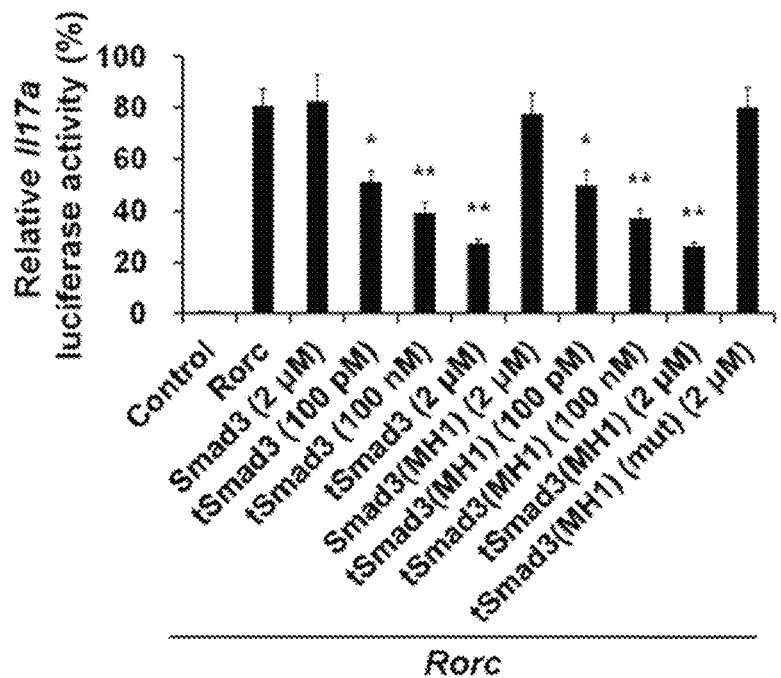
Figure 6D:
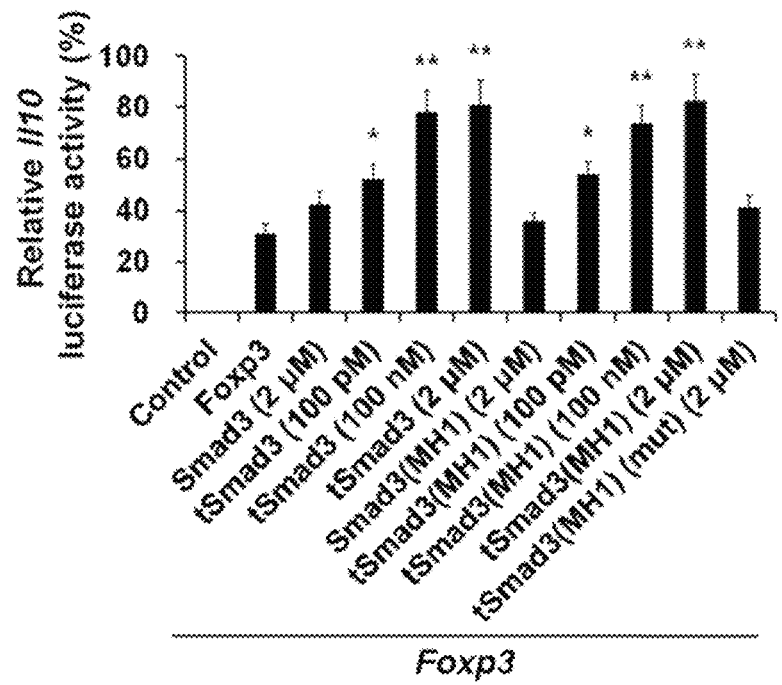
Figure 6E:
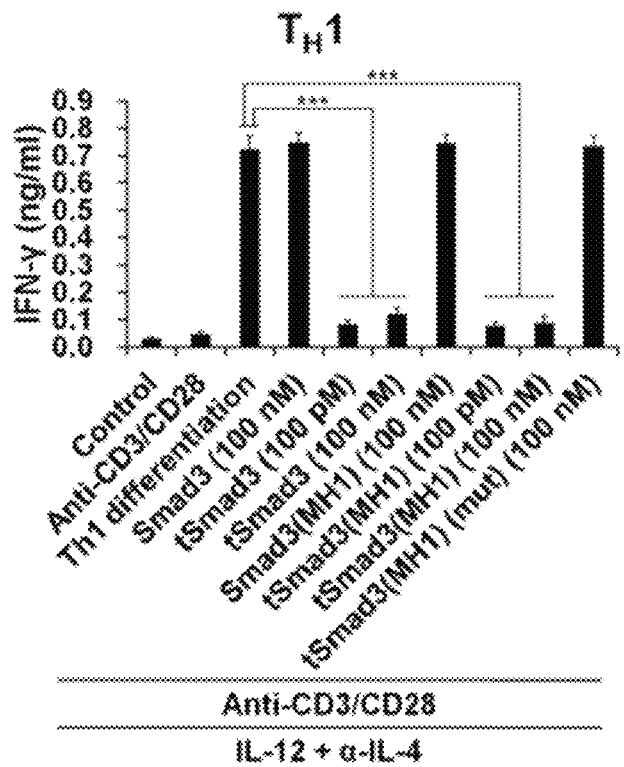
Figure 6F:
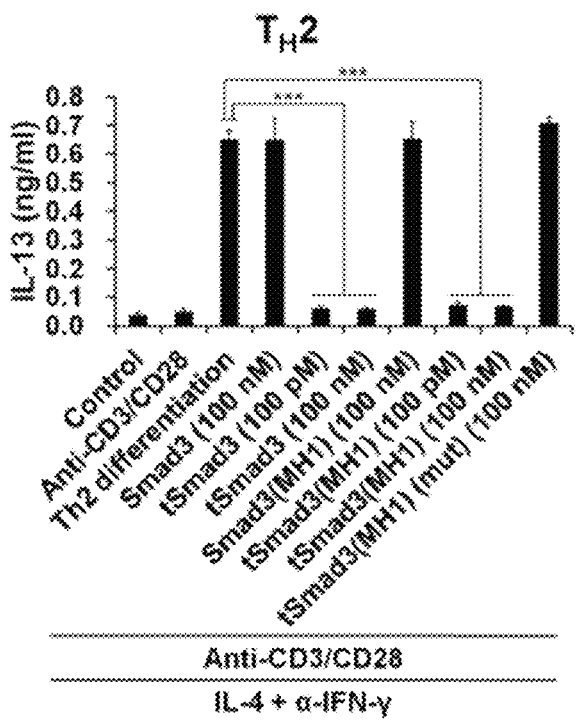
Figure 6G:
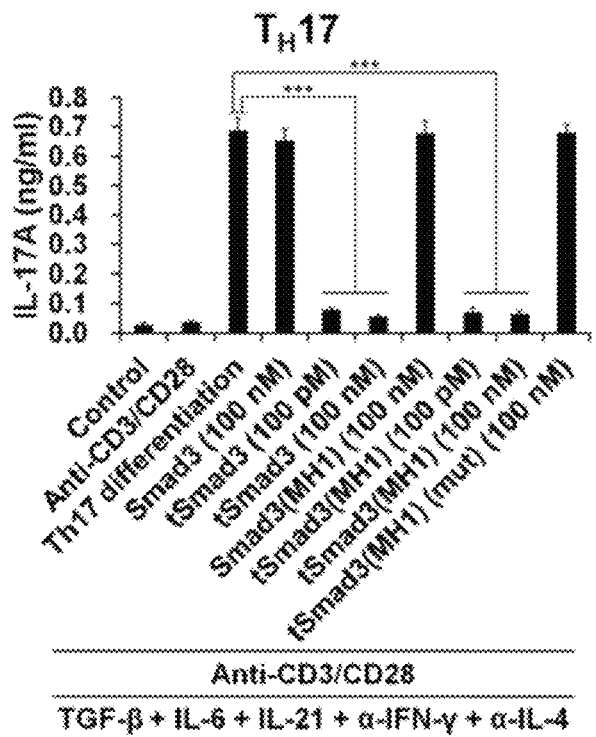
Figure 6H:
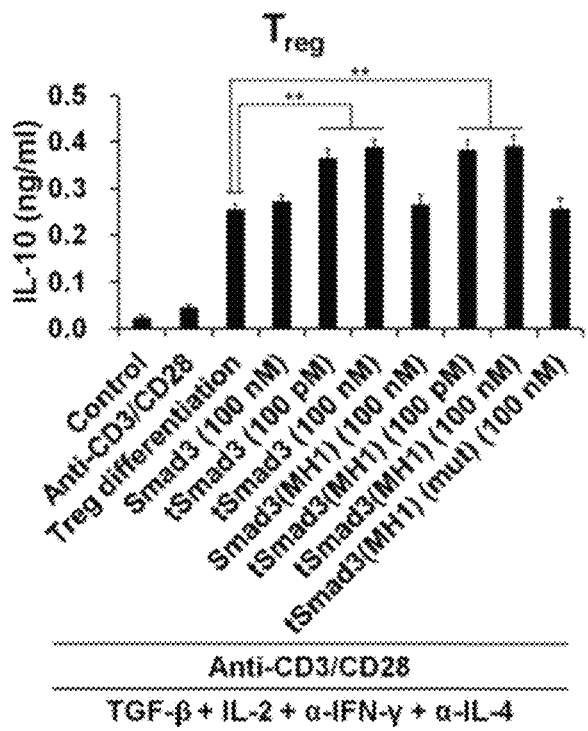

As a result, it could be seen that the cells treated with each of the tSmad3 and tSmad3(MH1) recombinant fusion proteins showed no cytotoxicity regardless of the concentration of the fusion protein, unlike cells not treated with the fusion protein (FIG. 4).

Experimental Example 5: Analysis of the Effects of tSmad3 and tSmad3(MH1) Recombinant Fusion Proteins on Transcriptional Modulation and on Regulation of Differentiation of Immature T Cells into TH Cells 5-1: Regulation of Production of IL-2, IFN-γ, IL-4, IL-17A and IL-10 in Splenocytes Splenocytes isolated from the spleens of 6-8-week-old female C57BL/6 mice were treated with the tSmad3 or tSmad3(MH1) recombinant fusion protein for 1 hour to transport the recombinant fusion protein into the cells. The cells were stimulated with anti-CD3 (1 μg/ml, BD Pharmingen) and anti-CD28 (1 μg/ml, BD Pharmingen), and then incubated for 72 hours. Next, the amounts of cytokines present in the culture medium were measured by ELISA.

Figure 3F:
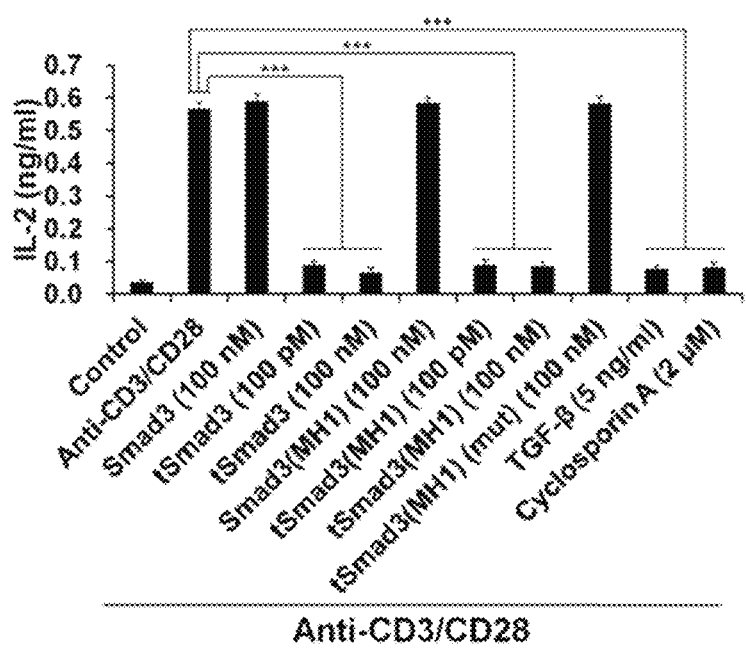
Figure 3G:
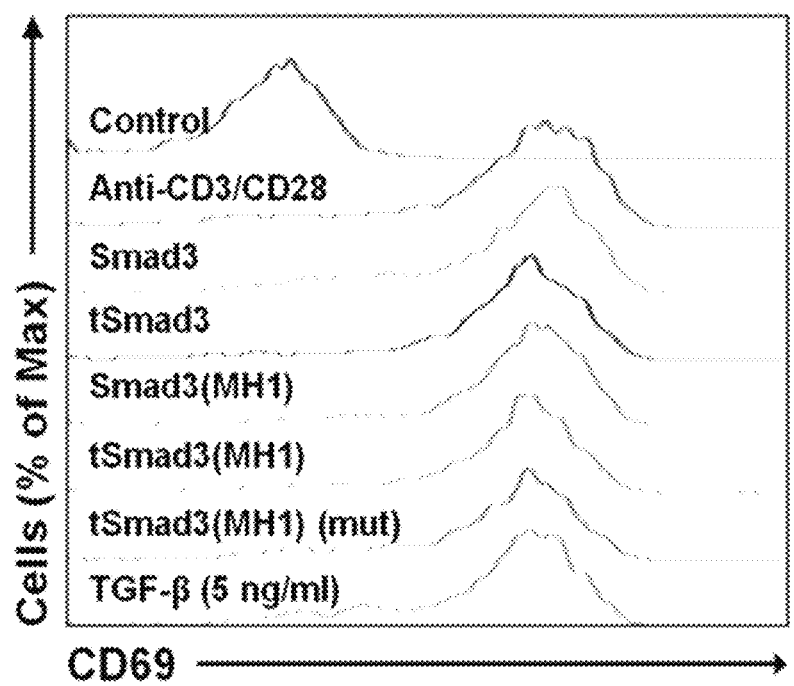

As a result, it could be seen that, when the cells were treated with tSmad3 or tSmad3(MH1), the expression levels of IL-2, IFN-γ, IL-4, IL-17A and IL-10 in the cells were regulated (FIGS. 3f and 5). In addition, the expression level of CD69, which is indicative of T cell activation, was measured by FACS Calibur (BD Biosciences), and as a result, it could be seen that tSmad3 or tSmad3(MH1) did not influence the expression of CD69 in T cells (FIG. 3g).

5-2: Phosphorylation of Intracellular Signal Transduction Protein

In order to examine whether or not the tSmad3 and tSmad3(MH1) fusion proteins are involved in tyrosine phosphorylation of proteins related to various intracellular signal transduction systems, Western blot analysis was performed. Jurkat T cells were treated with 2 μM of tSmad3 and tSmad3(MH1) for 1 hour, and then stimulated with anti-CD3 (2.5 μg/ml) and anti-CD28 (2.5 μg/ml), and whether or not tyrosine phosphorylation of ZAP-70, p38, JNK or ERK occurred was observed.

Figure 3H:
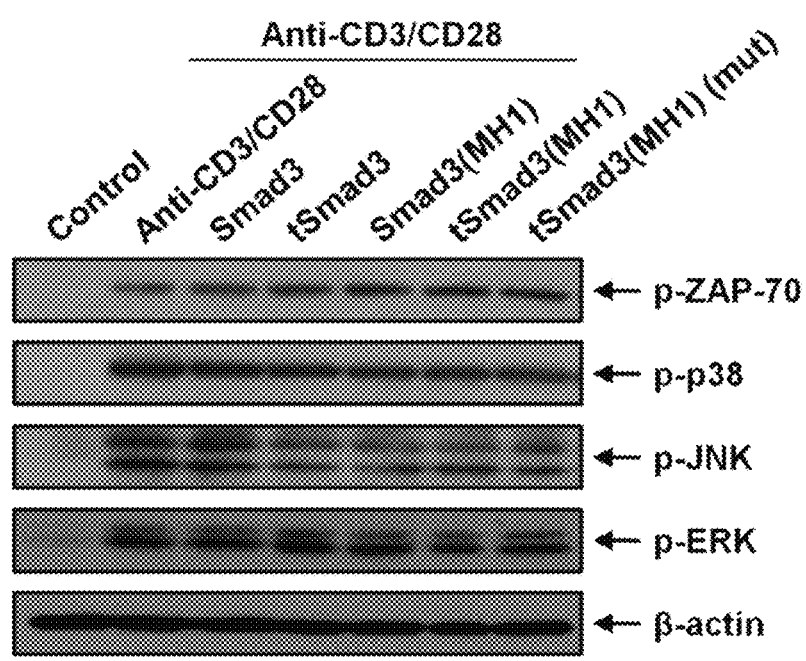

As a result, it could be seen that tSmad3 and tSmad3 (MH1) did not influence phosphorylation of these proteins (see FIG. 3h).

5-3: Analysis of Inhibitory Effects Against NFAT and NF-κB Transcription Factors in Jurkat T Cells Analysis was performed to determine whether or not the tSmad3 and tSmad3(MH1) fusion proteins inhibit the transcription of NFAT and NF-κB activated by Jurkat T-cell activation stimulated by anti-CD3 (1 μg/ml) and anti-CD28 (1 μg/ml). When T cells are activated, transcription of NF-κB and NFAT is activated to activate the downstream gene IL-2. For this reason, luciferase reporter gene was used. First, NF-κB and NFAT reporter plasmids having luciferase in the downstream region were transfected into the nucleus of Jurkat T cells by electroporation, and then the Jurkat T cells were stimulated with anti-CD3 and anti-CD28 and treated with each of the tSmad3 and tSmad3(MH1) recombinant fusion proteins.

Figure 3I:
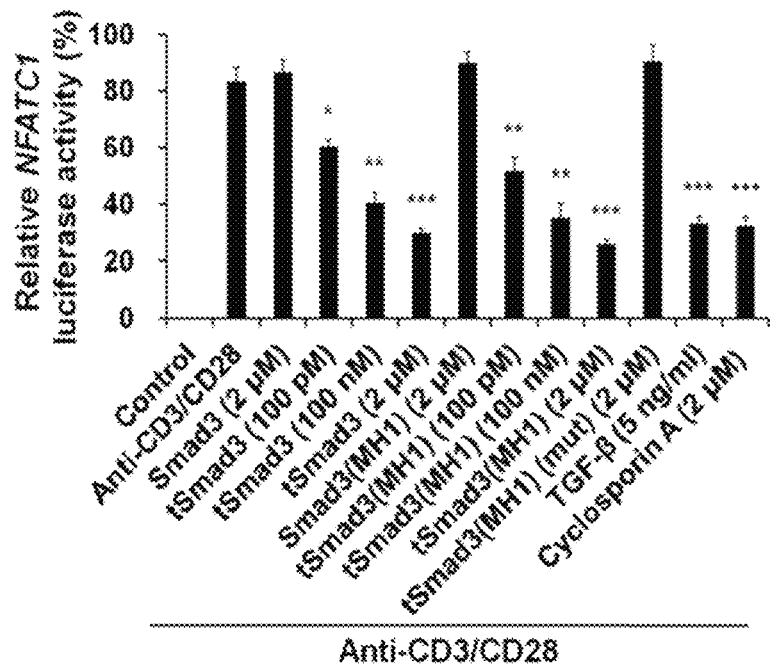
Figure 3J:
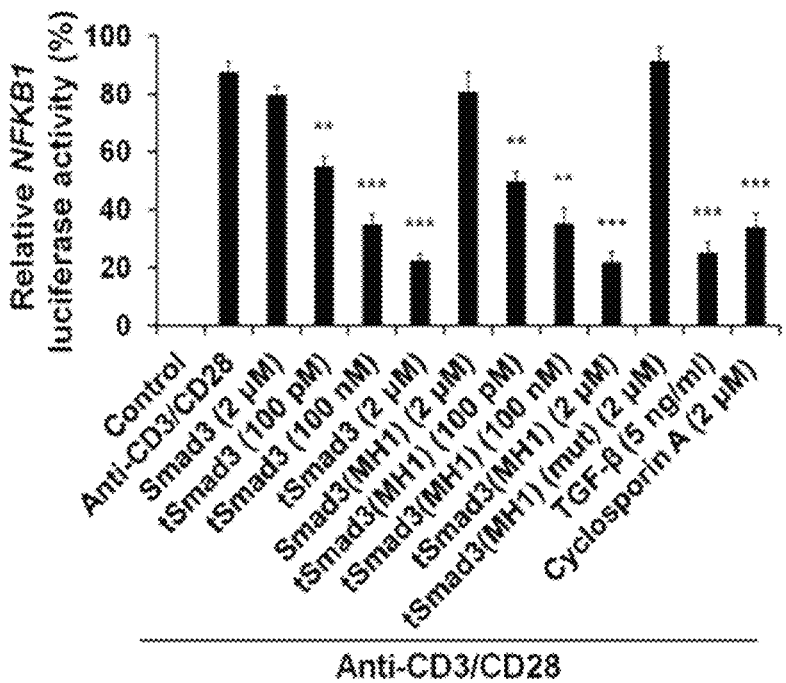

As a result, it could be seen that, when the cells were treated with each of the tSmad3 and tSmad3(MH1) recombinant fusion proteins, the transcriptional activities of NFAT and NF-κB were effectively inhibited (FIGS. 3i and 3j).

5-4: Analysis of the Effects of tSmad3 and tSmad3(MH1) Recombinant Fusion Proteins on Transcriptional Modulation IFN-γ, IL-4, IL-17A and IL-10 reporter plasmids, each having luciferase in the downstream region, and wild-type T-bet, GATA3, RORγt and Foxp3 genes, were transfected into the nucleus of HEK293T cells, and then the cells were treated with the tSmad3 or tSmad3(MH1) fusion protein.

As a result, it could be seen that the tSmad3 and tSmad3 (MH1) recombinant proteins effectively modulated the transcriptional activity of each of the genes (FIGS. 6a to 6d).

5-5: Analysis of Effects on Regulation of Differentiation of Immature T Cells into TH Cells Splenocytes were isolated from the spleens of 6-8-week-old female C57BL/6 mice, and then CD4+CD25-CD62L+ immature CD4 T cells which had not been exposed to any antigen were isolated from the splenocytes by MACS (magnetic cell sorting). The immature CD4 T cells were treated with varying concentrations of the tSmad3 or tSmad3(MH1) fusion protein, and then stimulated with anti-CD3 (1 μg/ml)

and anti-CD28 (1 μg/ml). Next, the cells were incubated for 72 hours with cytokines enabling differentiation into each type of TH cells.

For differentiation into Th1 cells, IL-12 (10 ng/ml) and anti-IL-4 (5 μg/ml) were added, and for differentiation into Th2 cells, IL-4 (40 ng/ml) and anti-IFN-γ (5 μg/ml) were added. For differentiation into Th17 cells, TGF-β1 (5 ng/ml), IL-6 (30 ng/ml), IL-21 (100 ng/ml), anti-IL-4 (5 μg/ml) and anti-IFN-γ (5 μg/ml) were added, and for differentiation into Treg cells, TGF-β1 (5 ng/ml), IL-2 (50 U/ml), anti-IL-4 (5 μg/ml) and anti-IFN-γ (5 μg/ml) were added. After 72 hours, the amounts of cytokines present in each culture medium were measured by ELISA.

As a result, it could be seen that the expressions of IFN-γ, IL-13 and IL-17A, which are cytokines specific for Th1, Th2 and Th17 cells, were significantly inhibited, whereas the expression of the cytokine IL-10 specific for Treg cells significantly increased. Such results suggest that tSmad3 or tSmad3(MH1) fusion protein can control the function of inflammatory Th1, Th2 and Th17 cells, and can induce the function of Treg cells that control such inflammatory cells (FIGS. 6e to 6h).

Experimental Example 6: Analysis of In Vivo Delivery of tSmad3(MH1) Recombinant Fusion Protein In order to examine whether or not the tSmad3(MH1) fusion protein is effectively delivered to CD4+ T cells in spleen, lymph node, thymus and kidney tissues, tSmad3(MH1) was injected intraperitoneally into C57BL/6 mice at a concentration of 200 μg/mouse. After 48 hours, CD4+ T cells were isolated from each of the cells, and the tSmad3(MH1) fusion protein delivered to the CD4+ T cells was analyzed by flow cytometry, a fluorescence microscope and a histological assay.

Figure 7A:
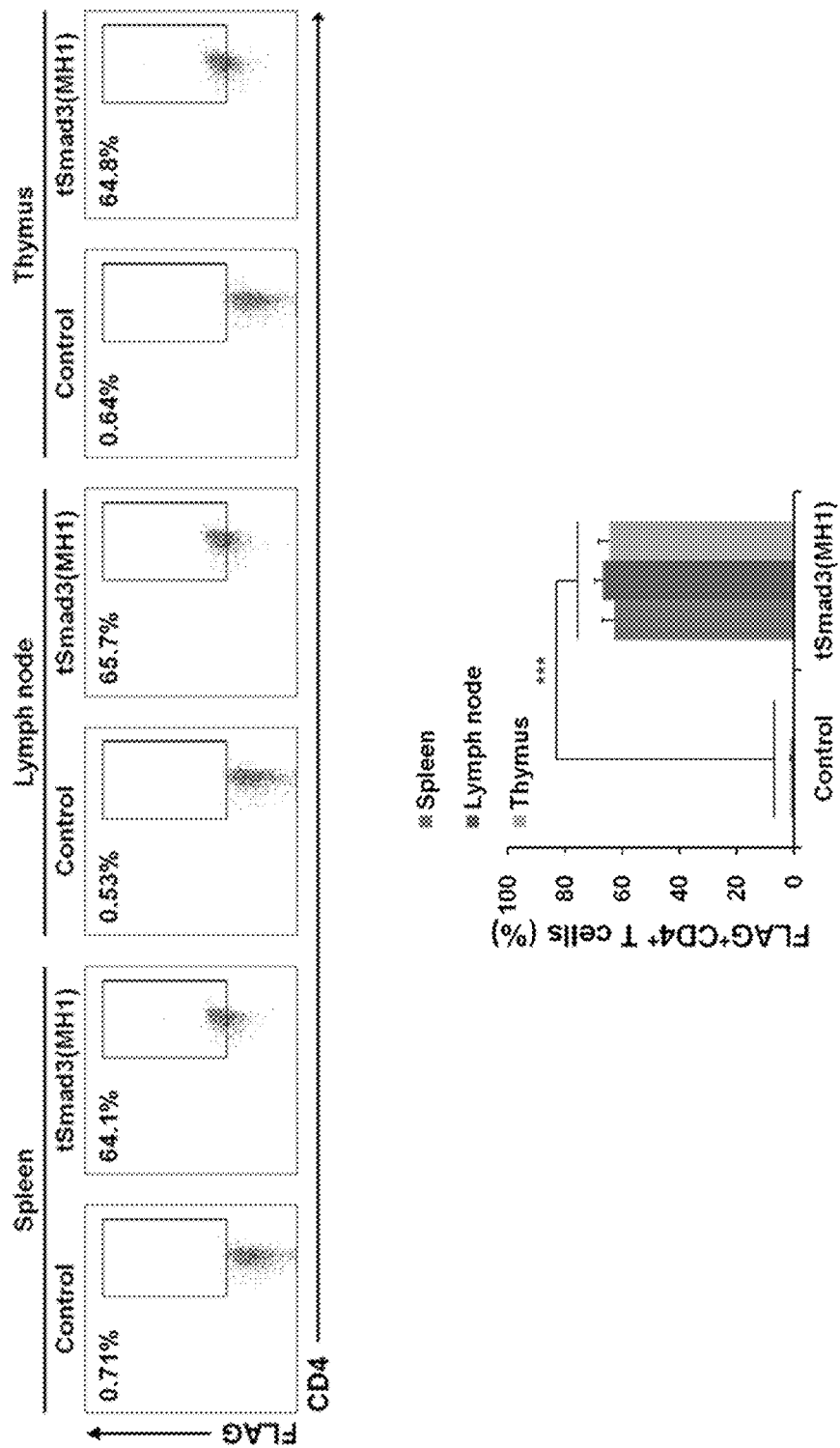
Figure 7B:
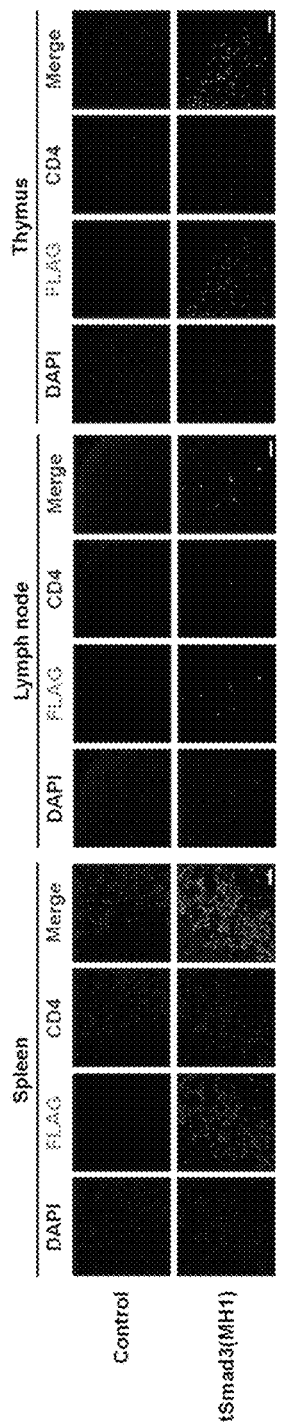
Figure 7C:
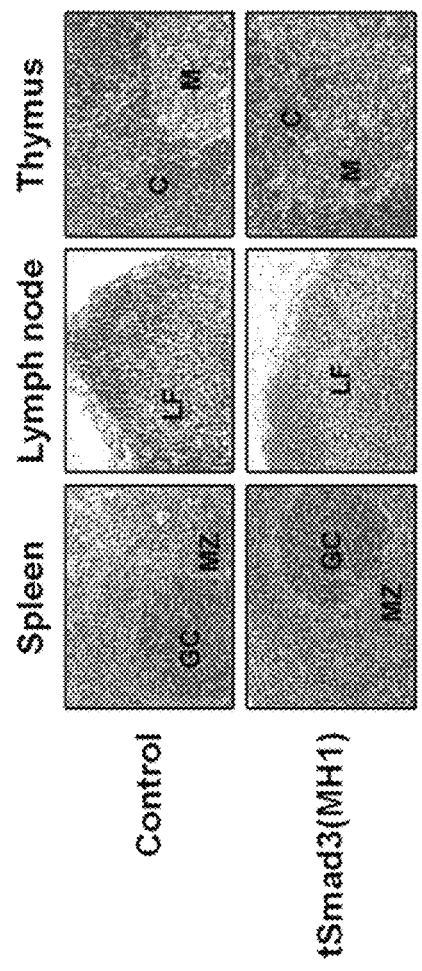

As a result, it could be seen that tSmad3(MH1) was effectively delivered to the CD4+ T cells in the spleen, lymph node, thymus and kidney tissues (FIGS. 7 and 8).

Experimental Example 7: Analysis of Preventive and Therapeutic Effects of tSmad3(MH1) Recombinant Fusion Protein in Lupus Nephritis Animal Models 7-1: Measurement of Proteinuria Level and Survival Rate in Lupus Nephritis Animal Models In order to analyze the preventive and therapeutic effects of the tSmad3(MH1) fusion protein in lupus nephritis animal models, an experiment was performed using generally engineered (NZB/NZW)F1 female mice.

In the case of lupus nephritis animal models used to examine the autoimmune disease preventive effect of tSmad3(MH1), Solu-Medrol (7 mg/kg), tSmad3(MH1)-High (200 μg/mouse) or tSmad3(MH1)-Low (50 μg/mouse) was injected intraperitoneally into lupus nephritis mice three times a week over a period from 13 weeks to 30 weeks after birth. In the case of lupus nephritis animal models used to examine the autoimmune disease therapeutic effect of tSmad3(MH1), Solu-Medrol (7 mg/kg), tSmad3(MH1)-High (200 μg/mouse) or tSmad3(MH1)-Low (50 μg/mouse) was injected intraperitoneally into lupus nephritis mice three times a week over a period ranging from 23 weeks to 30 weeks after birth. After injection, the proteinuria level and survival rate in the mice were measured.

The proteinuria level was measured twice a week during the experimental period, and quantified according to the following scoring system:

0=null; 1+=≤100 mg/dL; 2+=≤300 mg/dL; 3+=≤1,000 mg/dL; 4+=1,000 mg/dL.

As a result, it could be seen that the tSmad3(MH1) recombinant protein showed a significantly positive effect on the reduction of proteinuria compared to the control, and that the mice administered with tSmad3(MH1) did not die during the experimental period (FIGS. 9a, 9b, 10a and 10b).

7-2: Histopathological Analysis on Lupus Nephritis Animal Models

For histological evaluation of the tSmad3(MH1) fusion protein in the kidneys of mice with lupus nephritis, the mice at 30 weeks were sacrificed, and then each of the kidneys was fixed with 4% para-formaldehyde solution and embedded in paraffin, and then subjected to PAS (periodic acid-Schiff) staining to observe glomerulonephritis. Histopathological measurement was performed by two pathologists, and quantified according to the following scoring system:

0=not stained; 1=weakly stained; 2=moderately stained; 3=strongly stained.

Figure 9A:
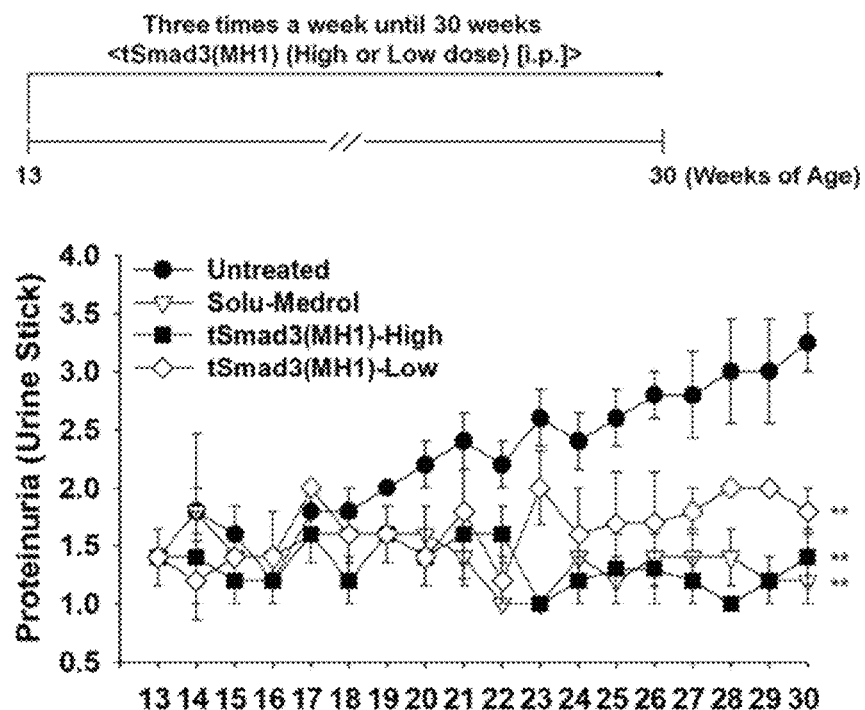
FIGS. 9A-9H show the results of analyzing the disease preventive effects of the fusion protein tSmad3(MH1) according to one embodiment of the present invention in lupus nephritis animal models. Specifically.
Figure 9B:
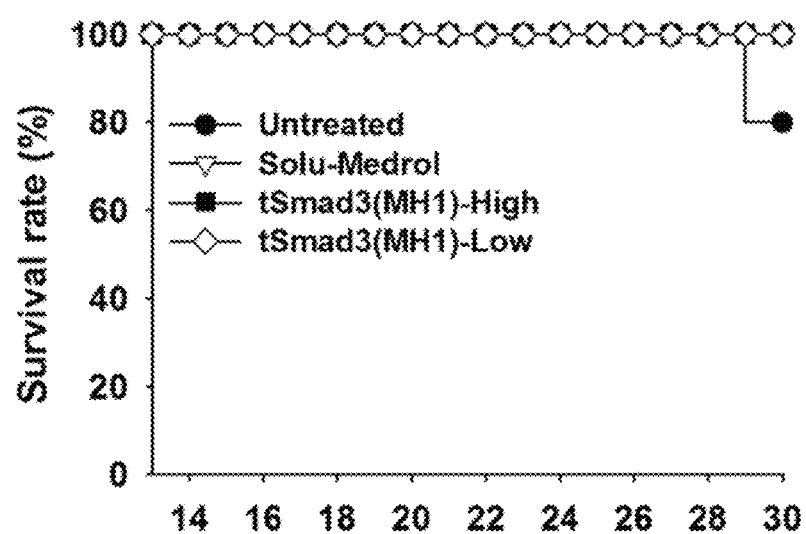
Figure 9C:
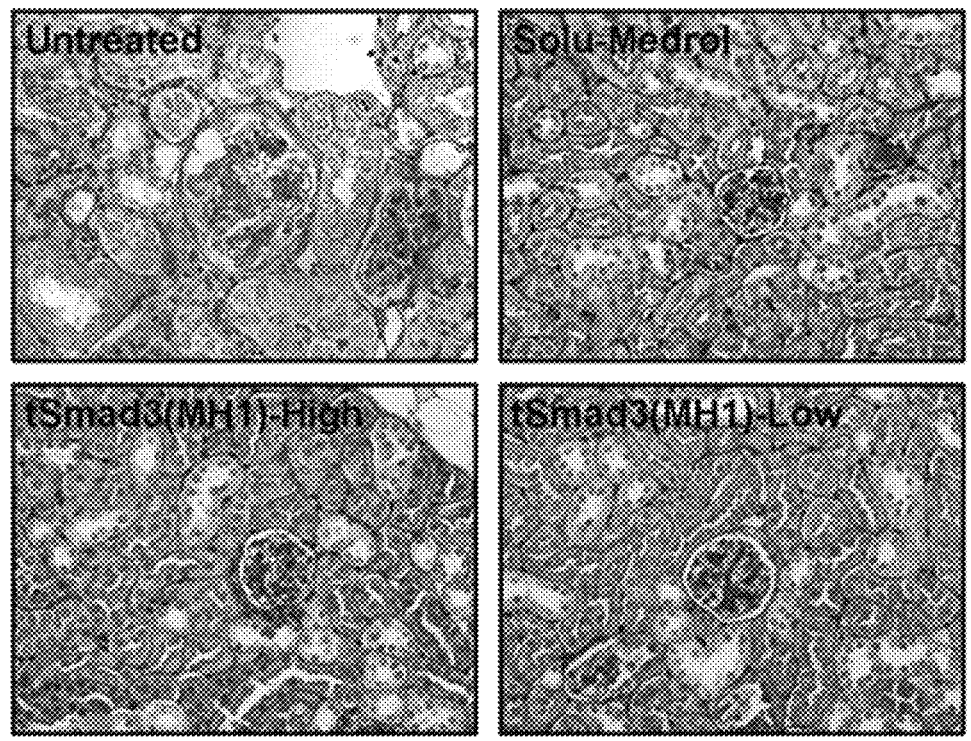
Figure 9C:
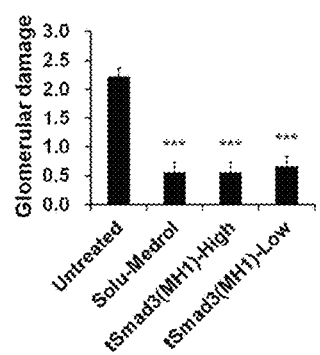
Figure 9C:
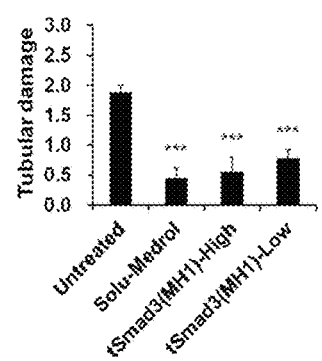
Figure 9C:
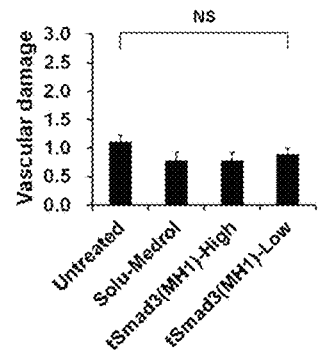
Figure 10A:
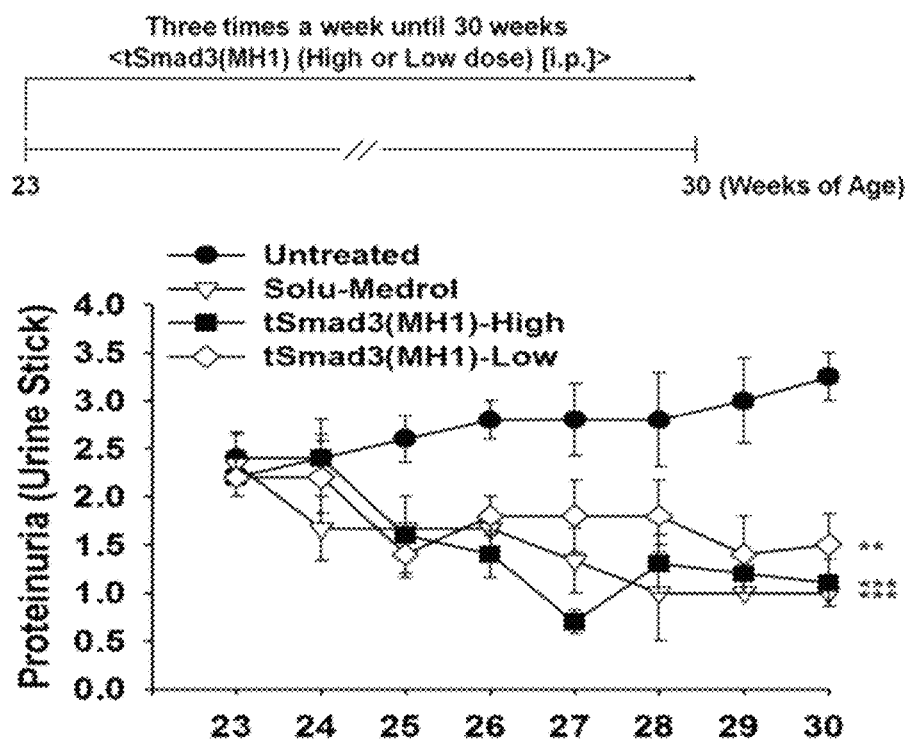
FIGS. 10A-10H show the therapeutic effects of the fusion protein tSmad3(MH1) according to one embodiment of the present invention in lupus nephritis animal models. Specifically.
Figure 10B:
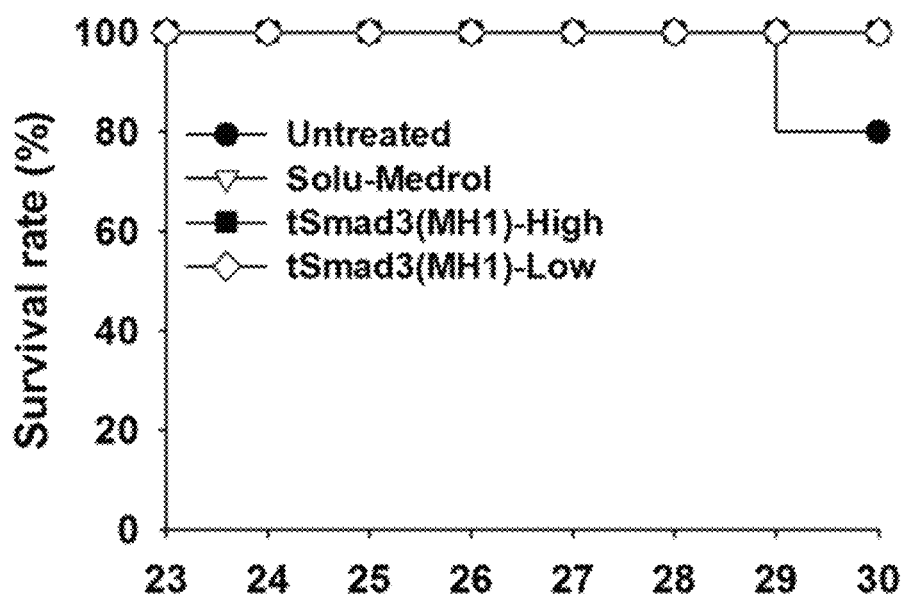
Figure 10C:
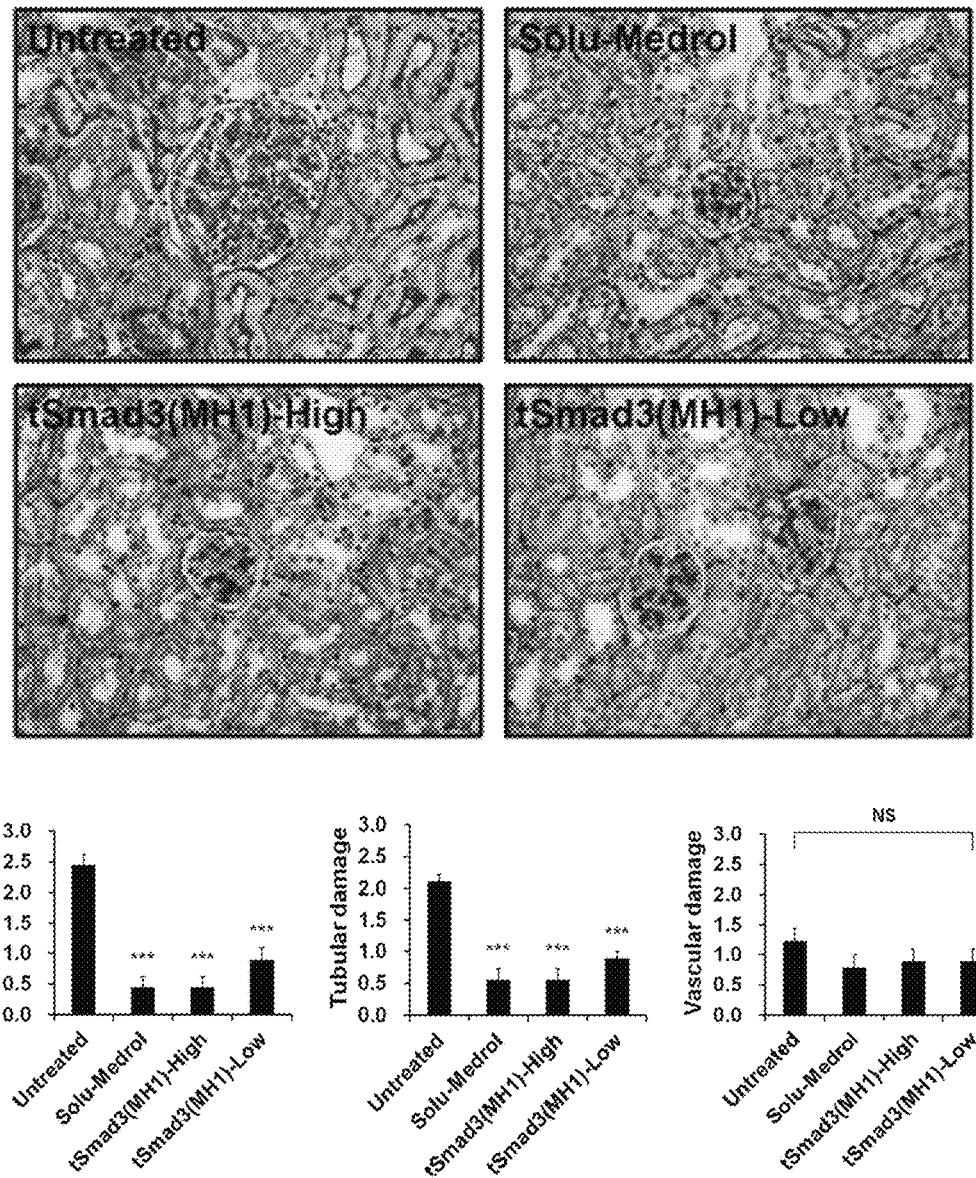

As a result, it could be seen that the group treated with tSmad3(MH1) showed a decrease in glomerular damage and tubular damage compared to the control group, and also showed no vascular damage (FIGS. 9c and 10c).

7-3: Immunofluorescent Staining on Lupus Nephritis Animal Models

In lupus nephritis, the formation of glomerular immune deposits plays an important role in renal pathology. For this reason, whether or not the formation of glomerular immune deposits is inhibited by the tSmad3(MH1) fusion protein was examined using a confocal microscope. Immunofluorescent staining measurement was performed by two pathologists and quantified according to the following scoring system:

0=not stained; 1=weakly stained; 2=moderately stained; 3=strongly stained.

Figure 9D:
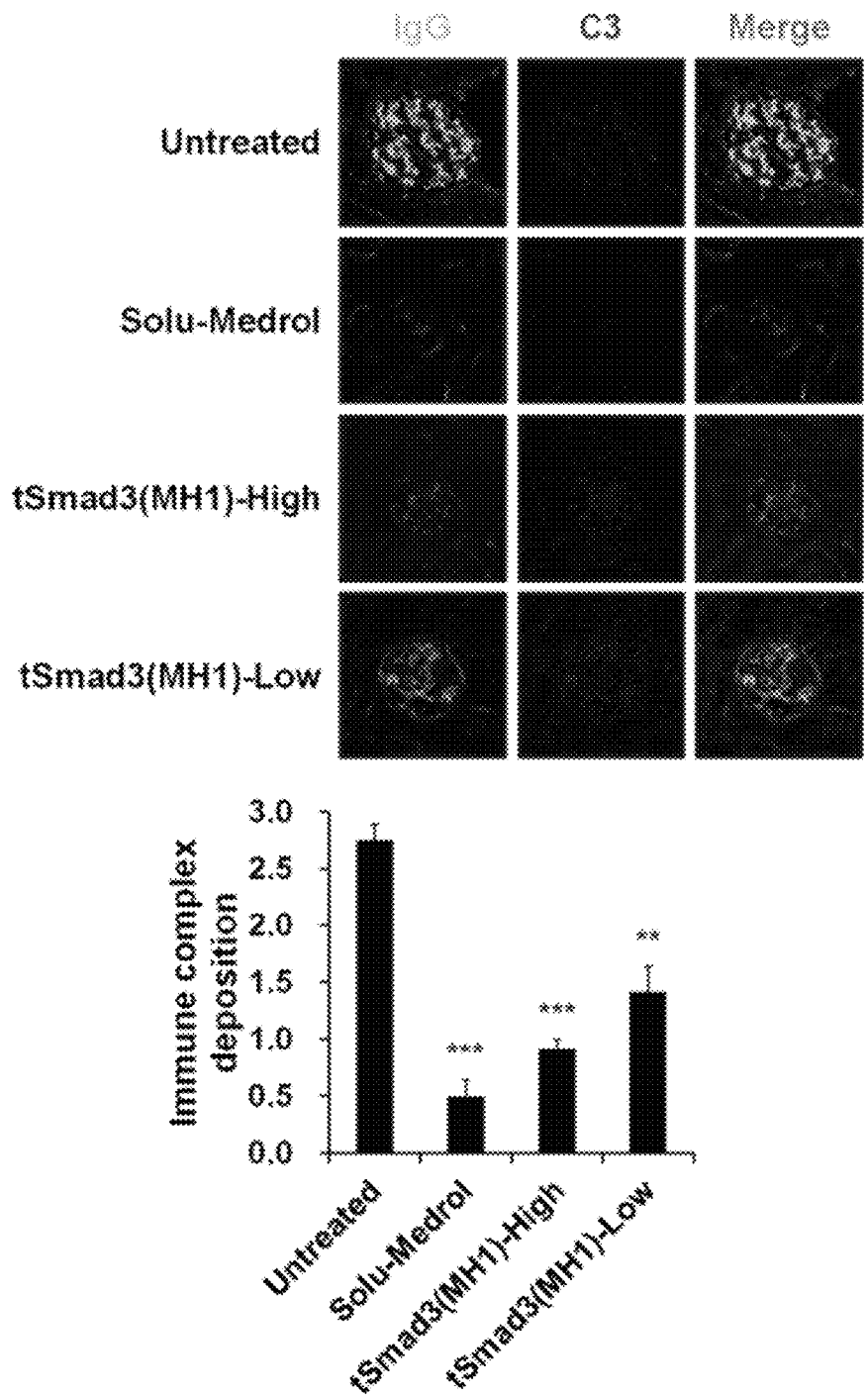
Figure 10D:
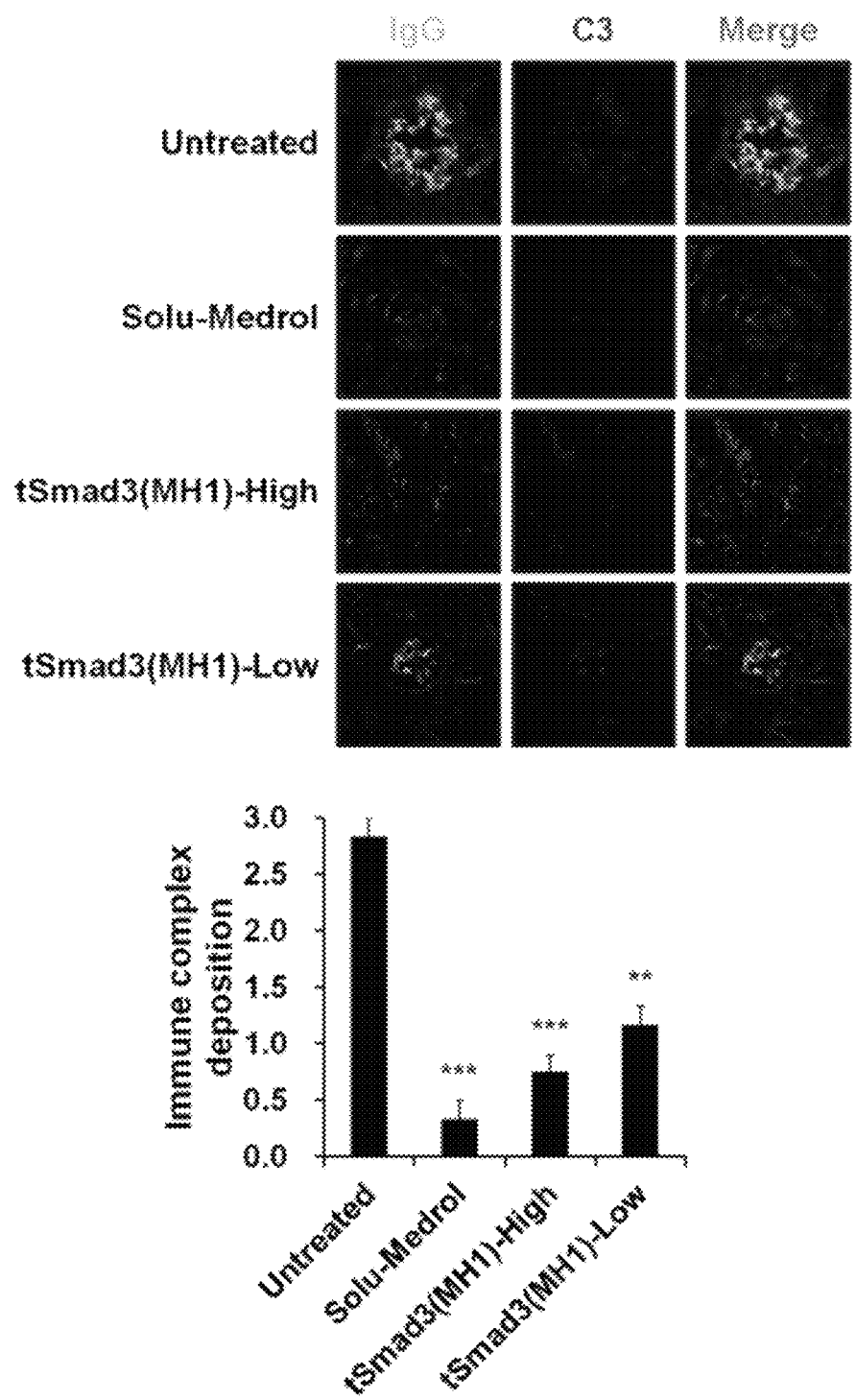
Figure 10F:
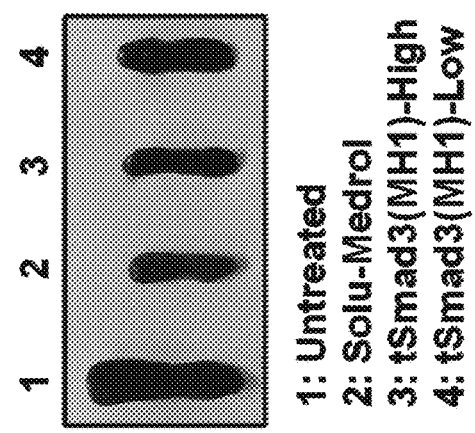

As a result, it could be seen that, in the control group, the deposition of IgG was detected by immunofluorescence, indicating that the control group had glomerulonephritis, whereas in the group treated with tSmad3(MH1), IgG was less detected. Such results suggest that tSmad3(MH1) inhibits the deposition of IgG to prevent the immune complex-mediated deterioration in renal function (FIGS. 9d and 10d).

7-4: Analysis of Serum Inflammatory Cytokines in Lupus Nephritis Animal Models

In order to examine whether or not the expression of serum inflammatory cytokines was inhibited by the tSmad3(MH1) fusion protein, an ELISA assay was performed.

Figures 9E, 9F:
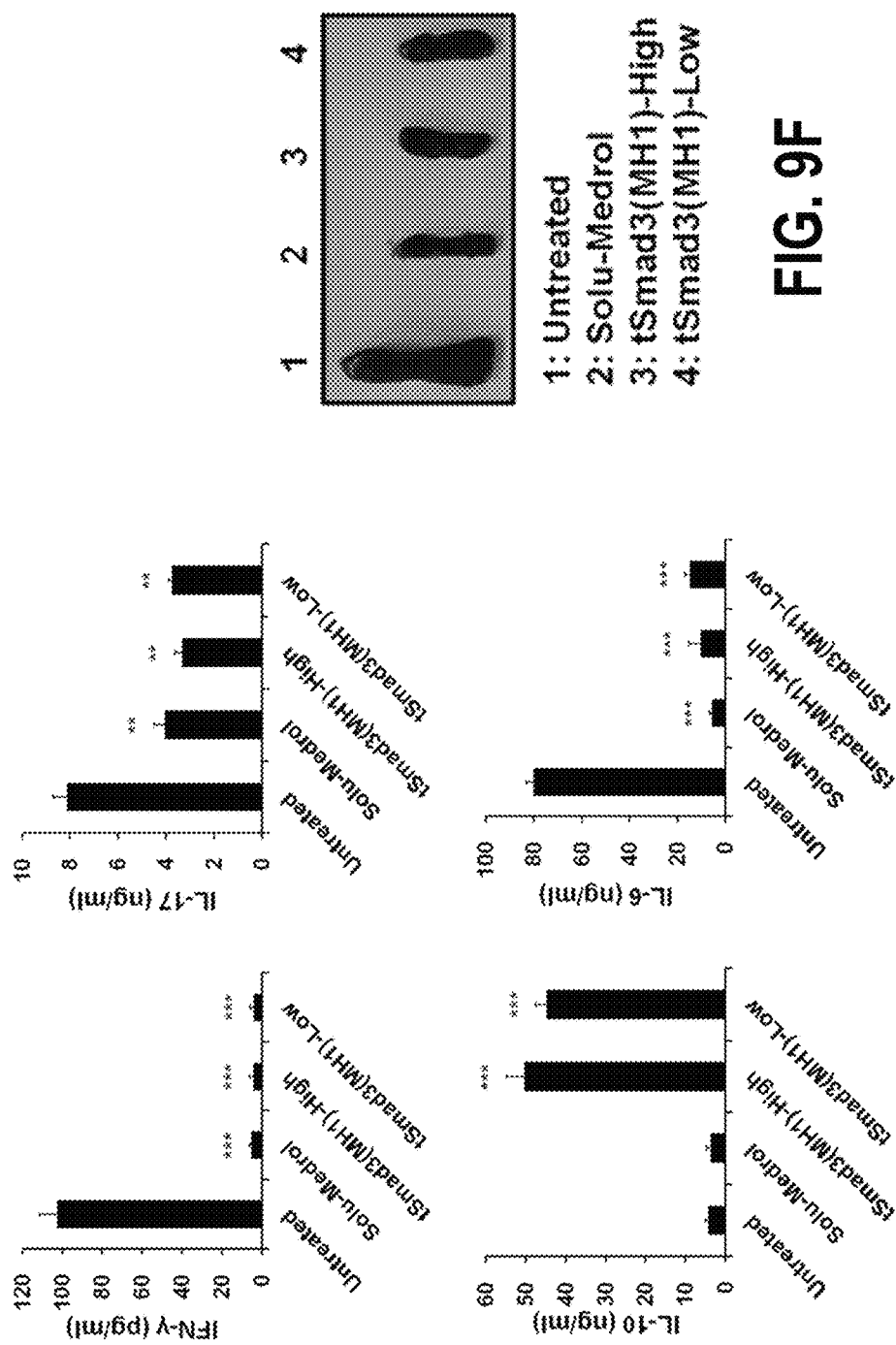
Figure 9G:
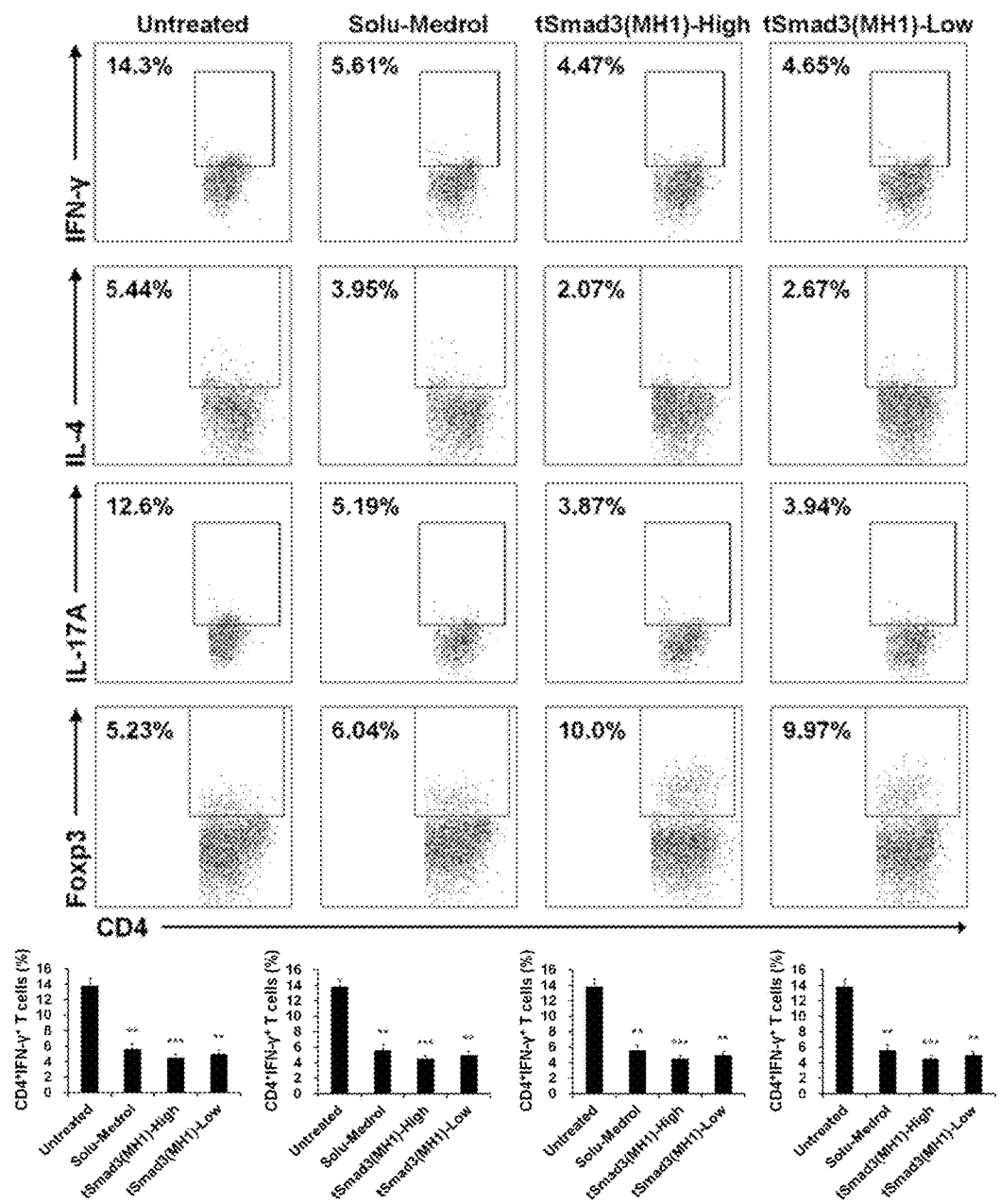
Figure 10E:
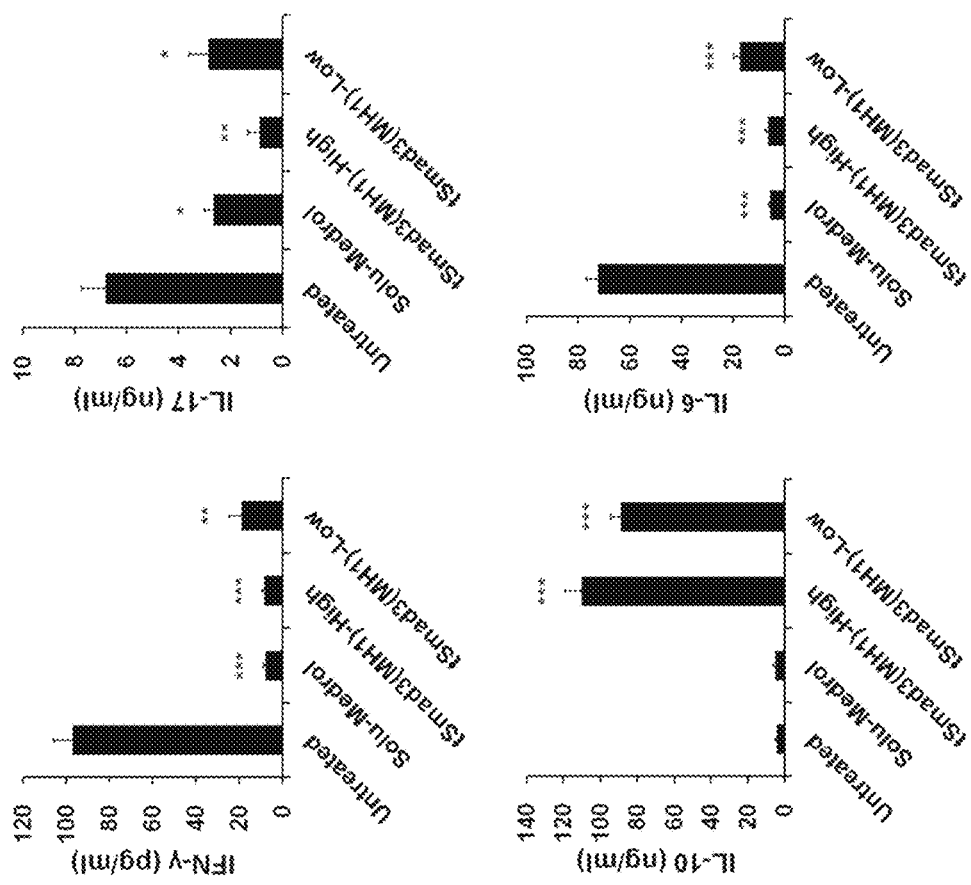
Figure 10G:
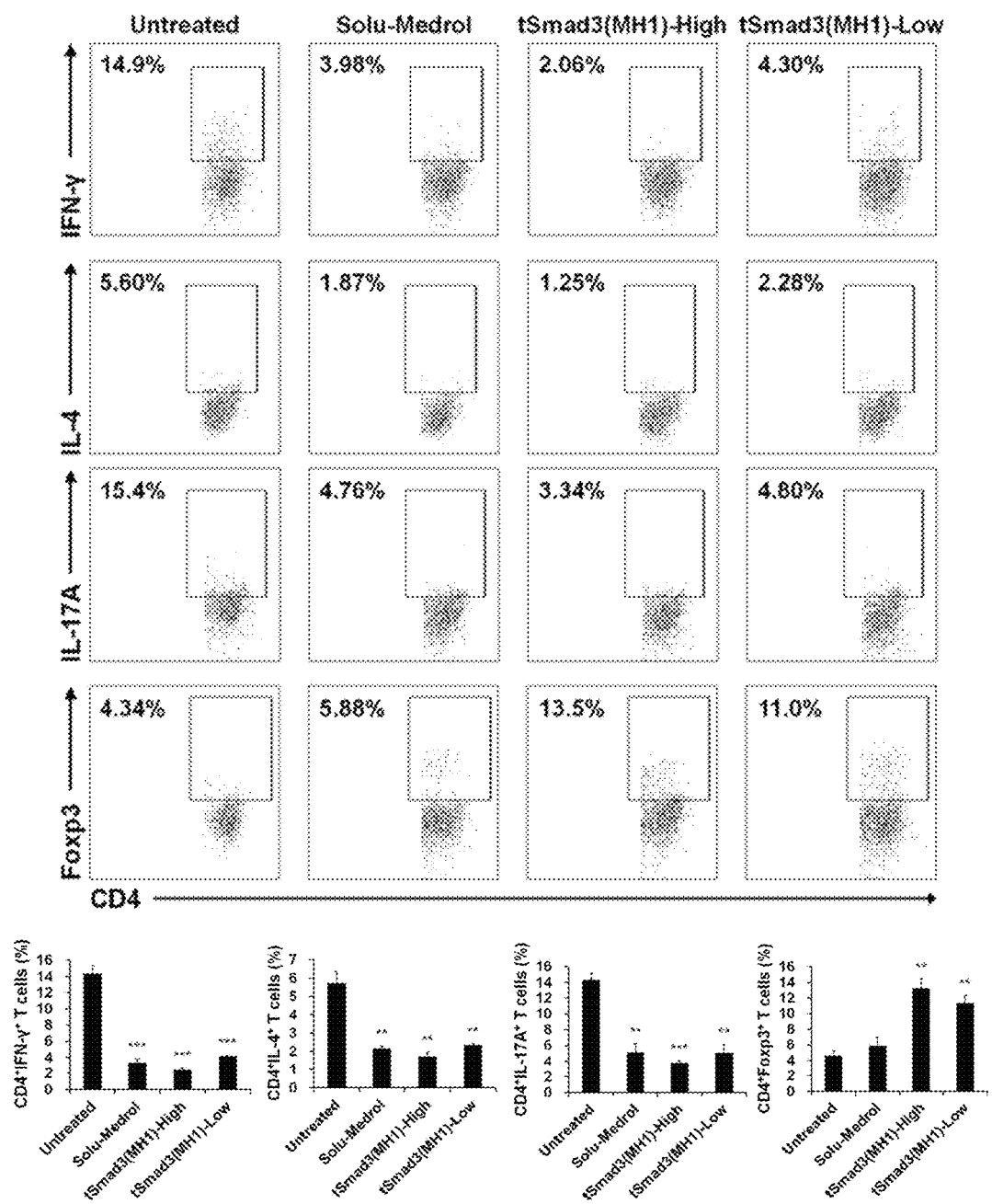

As a result, it could be seen that the expressions of the inflammatory cytokines IFN-γ, IL-6 and IL-17 in the group treated with tSmad3(MH1) were significantly inhibited compared to that in the control group, whereas the expression of IL-10 in the treated group significantly increased (FIGS. 9e and 10e).

7-5: Analysis of T Cells in Lupus Nephritis Animal Models

In order to analyze the change in T cells in lupus nephritis animal models by the tSmad3(MH1) fusion protein, the expressions of CD4+IFN-γ+, CD4+IL-4+, CD4+IL-17A+ and CD4+Foxp3+ cells in the splenocytes isolated in the mice of each group were analyzed by flow cytometry.

As a result, it could be seen that the expressions of Th1, Th2 and Th17 cells were significantly inhibited, but the expression of Treg cells significantly increased. This suggests that the tSmad3(MH1) fusion protein can inhibit the function of the inflammatory Th1, Th2 and Th17 cells, but induce the function of Treg cells that inhibit the inhibitory cells (FIGS. 9f, 9g, 10f and 10g).

7-6: Measurement of Anti-DNA and Autoantibody in Lupus Nephritis Animal Models

In order to examine the effects of the tSmad3(MH1) fusion protein on the production of anti-DNA, IgG1, IgG2a, IgG2b and IgG3 autoantibodies in serum, an experiment was performed using a Milliplex MAP Mouse Immunoglobulin Isotyping kit.

Figure 9H:
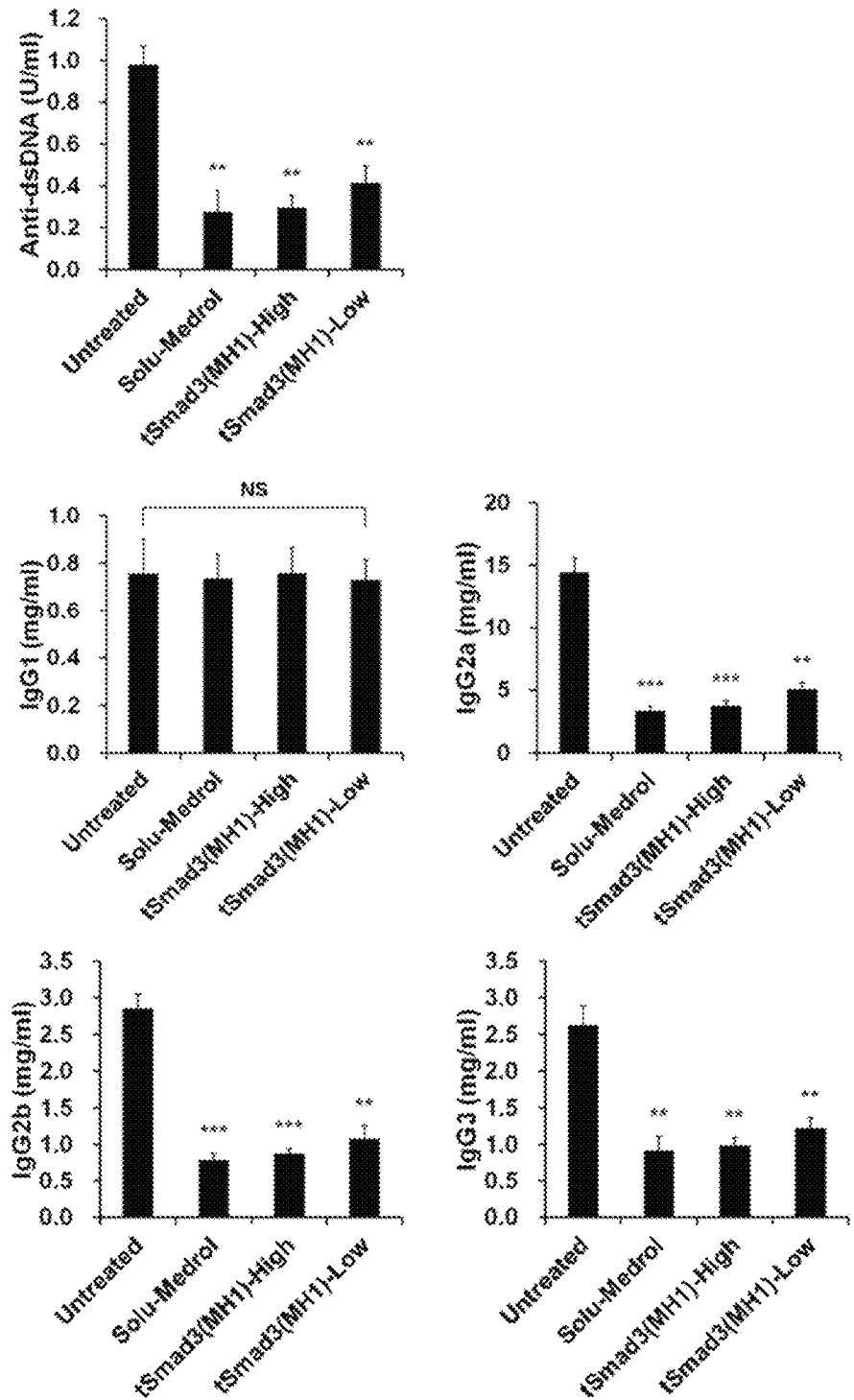
Figure 10H:
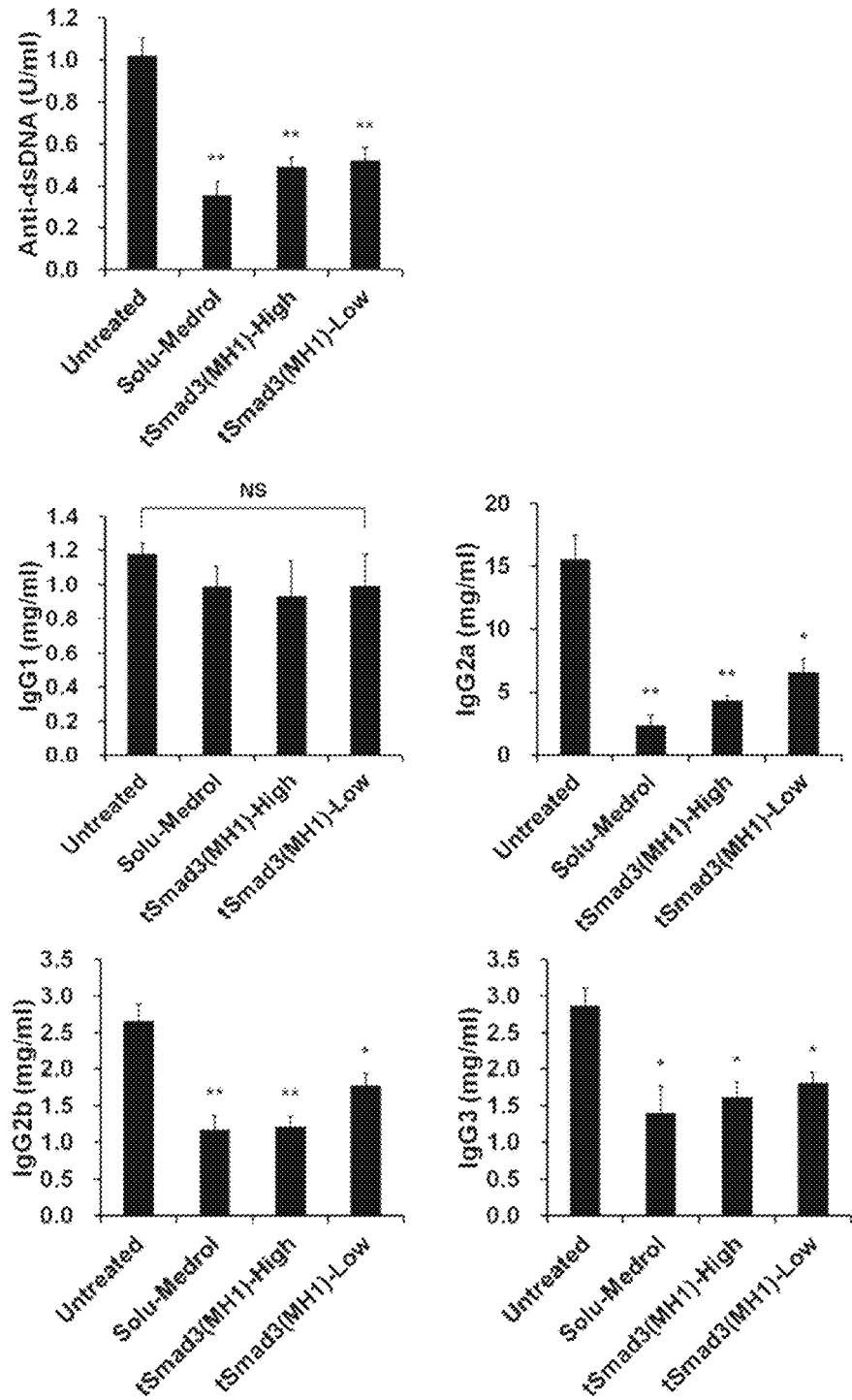

As a result, it could be seen that the production of anti-DNA in the group treated with tSmad3(MH1) was inhibited compared to that in the control group, and the expression of IgG2a, IgG2b and IgG3 in the treated group was significantly inhibited, whereas the production of IgG1 did not greatly differ between the treated group and the control group (FIGS. 9h and 10h).

Experimental Example 8: Analysis of Preventive and Therapeutic Effects of tSmad3(MH1) Recombinant Fusion Protein in Rheumatoid Arthritis Animal Models 8-1: Measurement of Arthritis Severity in Rheumatoid Arthritis Animal Models In order to analyze the preventive and therapeutic effects of the tSmad3(MH1) recombinant fusion protein in rheumatoid arthritis animal models, 7-8-week-old male DBA/1 mice (SLC, Shizoka, Japan) were used. 200 μg of an antigen solution prepared by mixing CFA (complete Freud's adjuvant) and bovine type II collagen at a mass ratio of 1:1 was injected intradermally into the mice. After 2 weeks, the antigen solution was injected again into the mice by the same method at the same dose.

In the case of rheumatoid arthritis animal models used to analyze the preventive effects of tSmad3(MH1), a first type-2 collagen antigen was injected into mice at 8 weeks (week 0 of treatment) after birth, and a second collagen antigen was injected into the mice at 10 weeks (week 2 of treatment) after birth. Treatment of the mice with tSmad3 (MH1) was performed for 7 weeks (from 8 weeks (week 0 of treatment) to 15 weeks (7 weeks of treatment) after birth).

In the case of rheumatoid arthritis animal models used to analyze the therapeutic effects of tSmad3(MH1), a first type-2 collagen antigen was injected into mice at 8 weeks (week 0 of treatment) after birth, and a second collagen antigen was injected into the mice at 10 weeks (week 2 of treatment) after birth. At 12 weeks (week 4 of treatment) after birth, induction of arthritis was observed. Treatment of the mice with tSmad3(MH1) was performed for 4 weeks (from 12 weeks (week 4 of treatment) to 16 weeks (week 8 of treatment) after birth). A negative control group and a positive control group were injected intraperitoneally with physiological saline three times a week, and the treated groups were injected intraperitoneally with Methotrexate (MTX, 35 mg/kg), tSmad3(MH1)-High (200 μg/mouse), tSmad3(MH1)-Low (50 μg/mouse) or mutant tSmad3(MH1) (200 μg/mouse). After injection, the severity of arthritis in the mice was measured.

For measurement of the severity of arthritis, whether or not foot redness, edema and deformity occurred was visually observed twice a week during the experimental period. Based on the results of the observation, the severity of arthritis at each time point was measured, and quantified according to the following scoring system:

0=normal relative to the negative control group; 1=presence of light inflammation (redness or edema) in the center of the foot or one of toe, ankle and knee joint; 2=occurrence of severe arthritis in several regions; 3=observation of severe inflammation attacking the whole of the foot; 4=either ankylosis resulting from the inflammation of score 3, or loss of joint movement.

Figure 11A:
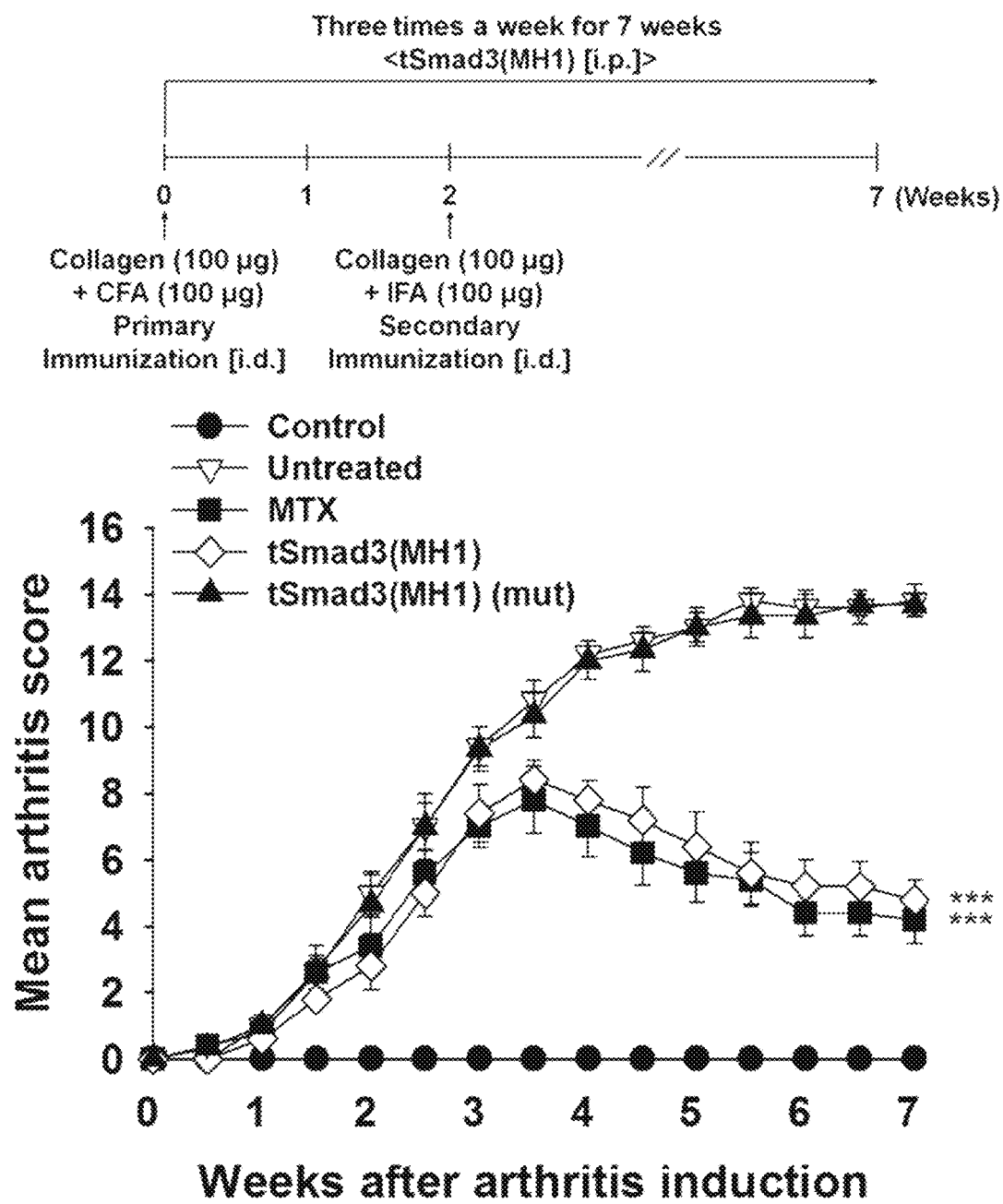
Figure 12A:
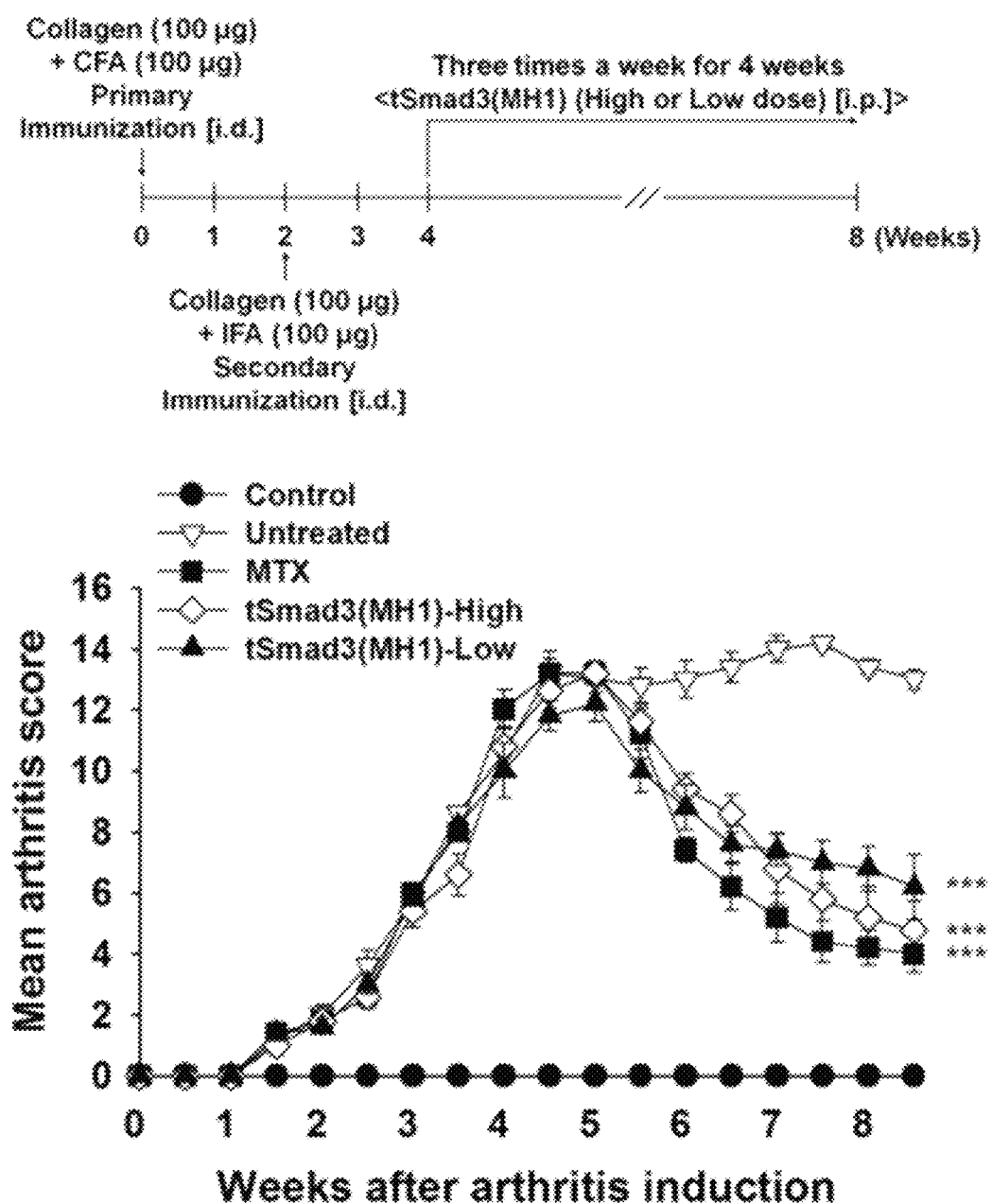
FIGS. 12A-12F show the results of analyzing the therapeutic effects of the fusion protein tSmad3(MH1) according to one embodiment of the present invention in rheumatoid arthritis animal models. Specifically.

As a result, it could be seen that the untreated control group showed clear arthritis symptoms such as edema and redness, whereas, in the group treated with tSmad3(MH1) by intraperitoneal injection, the arthritis severity and the feet thickness decreased in proportion to the concentration of tSmad3(MH1) administered (FIGS. 11a, 11b and 12a).

8-2: Histopathological Analysis on Rheumatoid Arthritis Animal Models

In order to verify the therapeutic effects of the tSmad3 (MH1) fusion protein, analysis was performed to measure the infiltration of inflammatory cells in tissues around the synovium and joint of mice with rheumatoid arthritis, the excessive proliferation of synovial cells, and the extent of partial bone defects.

For this, the mice were sacrificed, and then the joint tissue was fixed in neutral formalin buffer. The fixed tissue was decalcified with formic acid, and then embedded in paraffin, followed by H&E staining. In addition, immunochemical staining was performed in order to examine the inflammatory cytokines TNF-α, IL-1β and IL-6, which are involved in the pathology of rheumatoid arthritis, and the extent of joint damage and deformity. Histopathological measurement was performed by two pathologists and quantified according to the following scoring system:

0=not stained; 1=weakly stained; 2=moderately stained; 3=strongly stained.

Figure 12B:
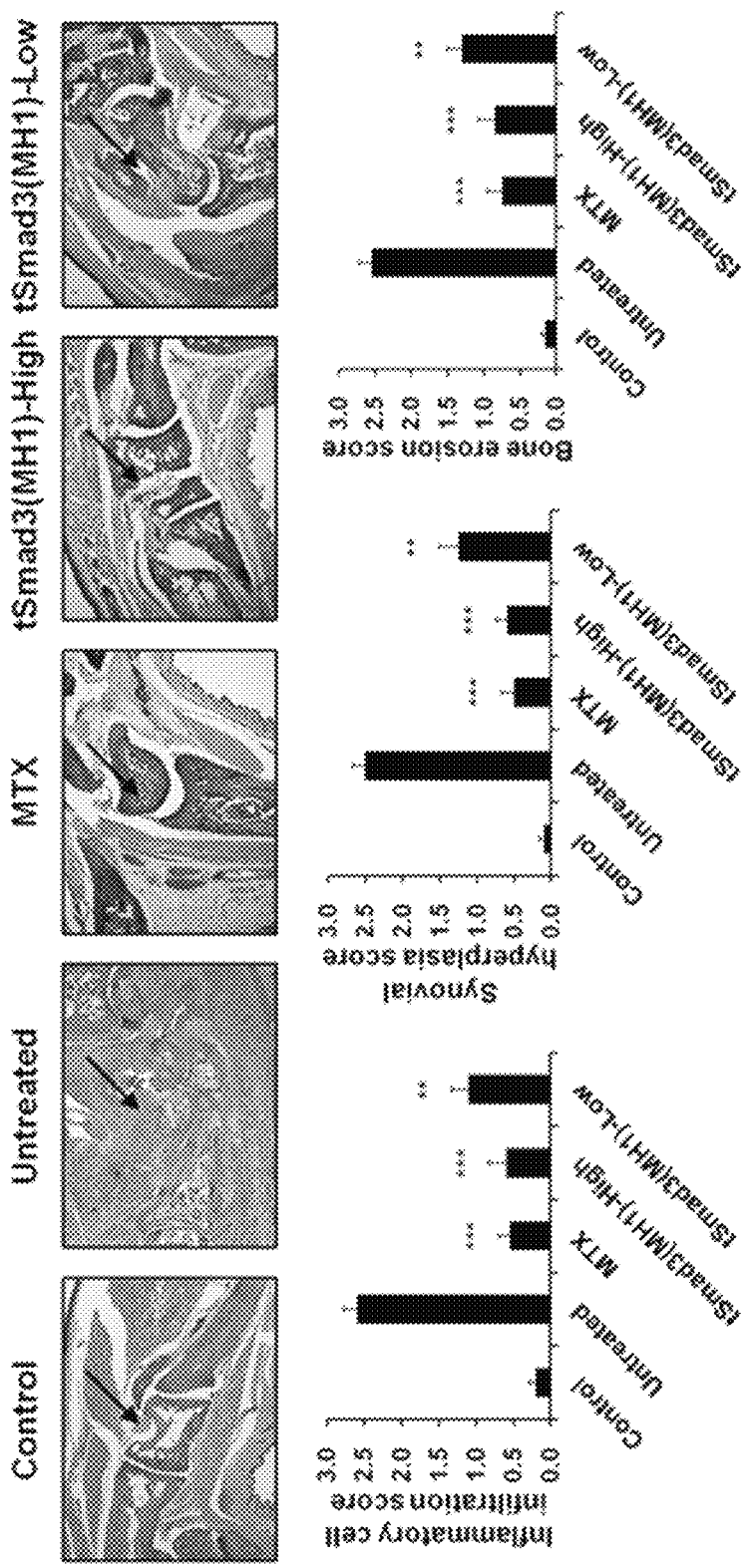
Figure 12C:
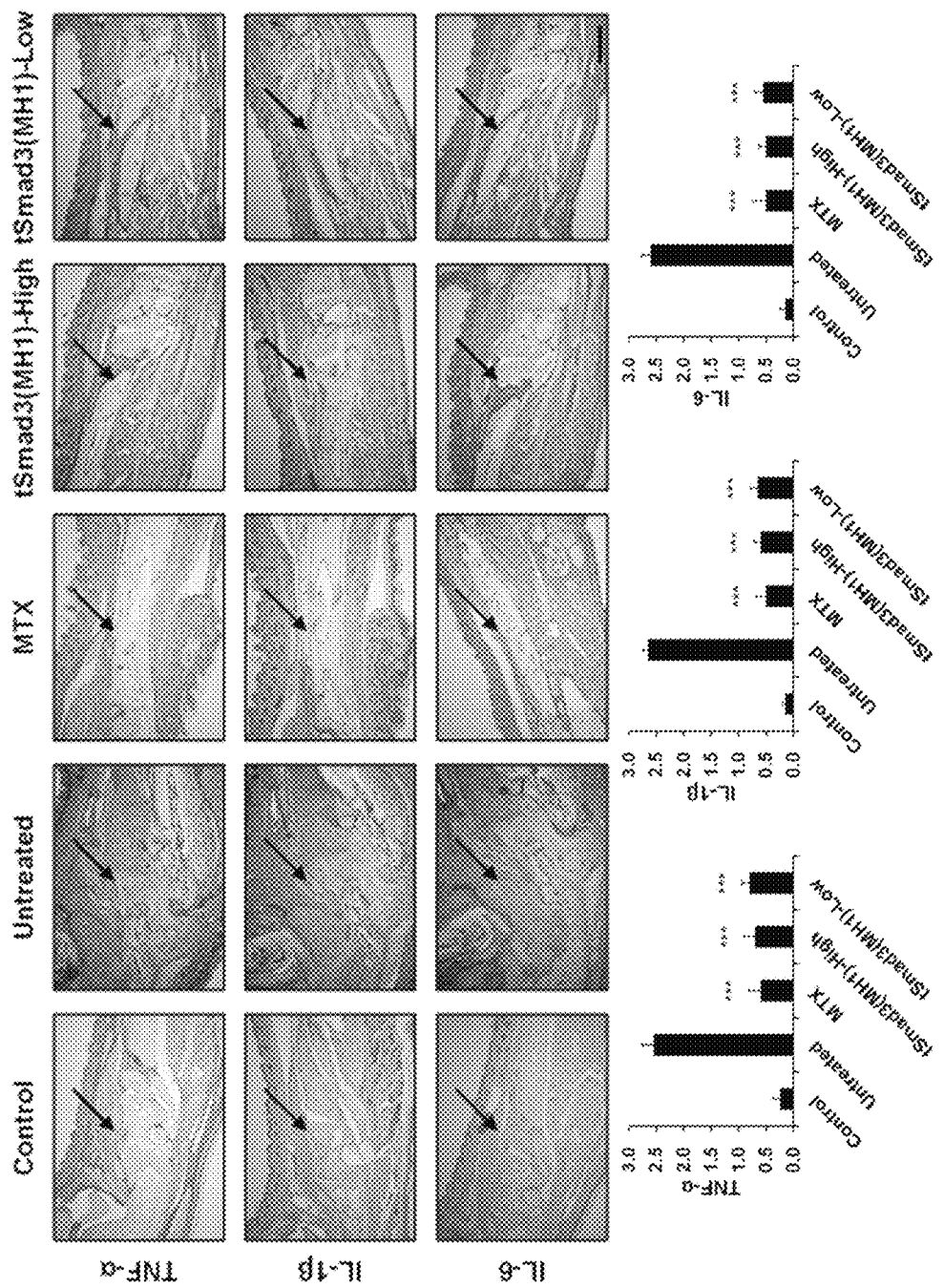
Figure 12D:
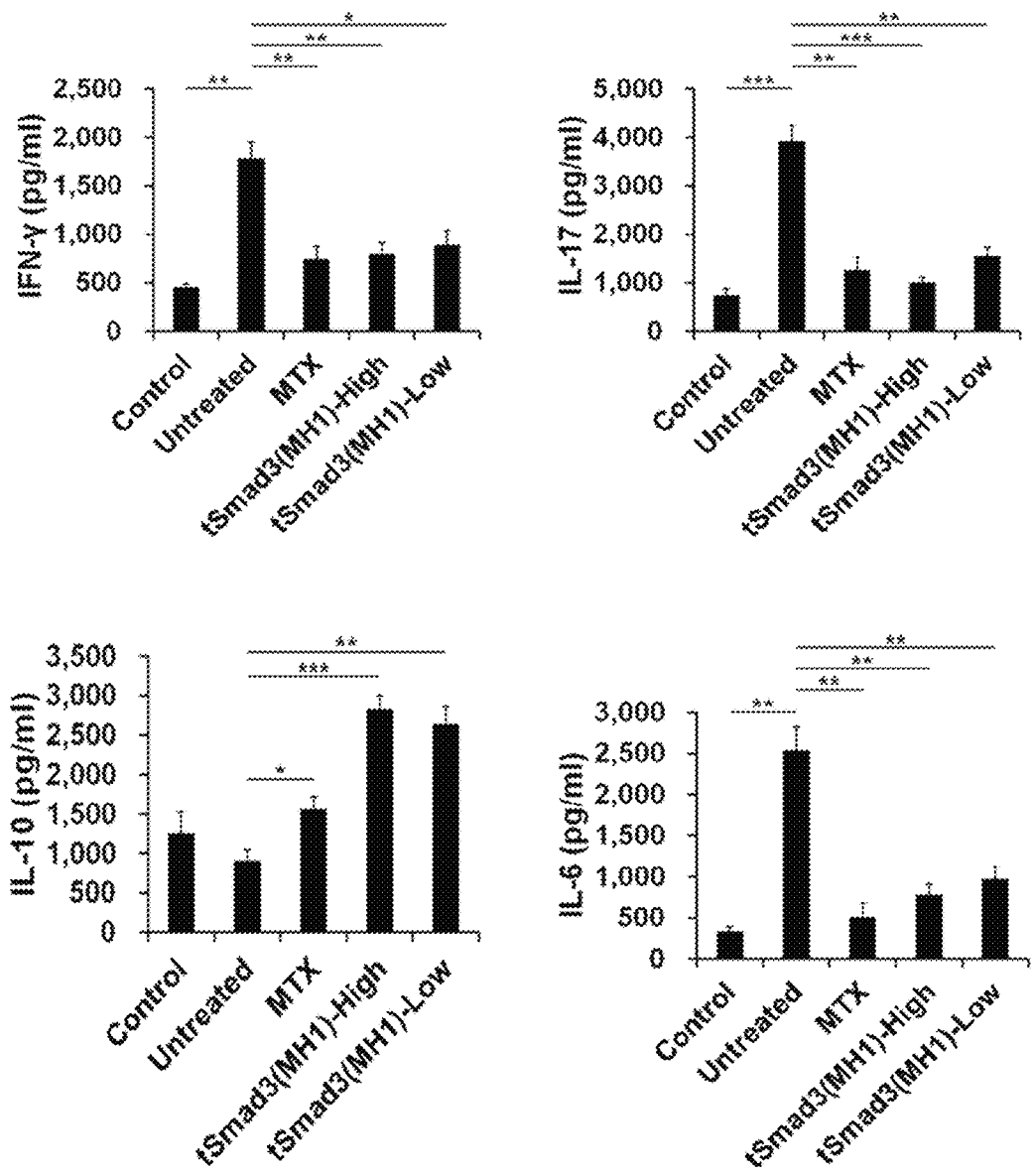

Histological staining of arthritis areas was performed, and as a result, it could be seen that, in the control group, infiltration of inflammatory cells, excessive proliferation of synovial cells, and partial bone defects were observed, but in the group treated with tSmad3(MH1), pathological changes were significantly reduced (FIGS. 12b and 12c).

8-3: Analysis of Inflammatory Cytokines in Splenocytes and Sera of Rheumatoid Arthritis In order to examine whether or not the expression of inflammatory cells in the splenocytes and sera isolated from mouse spleens is inhibited by the tSmad3(MH1) fusion protein, an ELISA assay was performed.

As a result, it could be seen that the expressions of the inflammatory cytokines IFN-γ, IL-6 and IL-17 in the group treated with tSmad3(MH1) were significantly inhibited compared to those in the control group, whereas the expression of IL-10 significantly increased (FIGS. 11c, 11d, 11 e and 12d).

8-4: Analysis of T Cells in Rheumatoid Arthritis Animal Models

In order to examine the change in T cells of rheumatoid arthritis animal models by the tSmad3(MH1) fusion protein, the expressions of CD4+IFN-γ+, CD4+IL-4+, CD4+IL-17A+ and CD4+Foxp3+ in splenocytes isolated from the mice of each group were analyzed by flow cytometry.

Figure 12E:
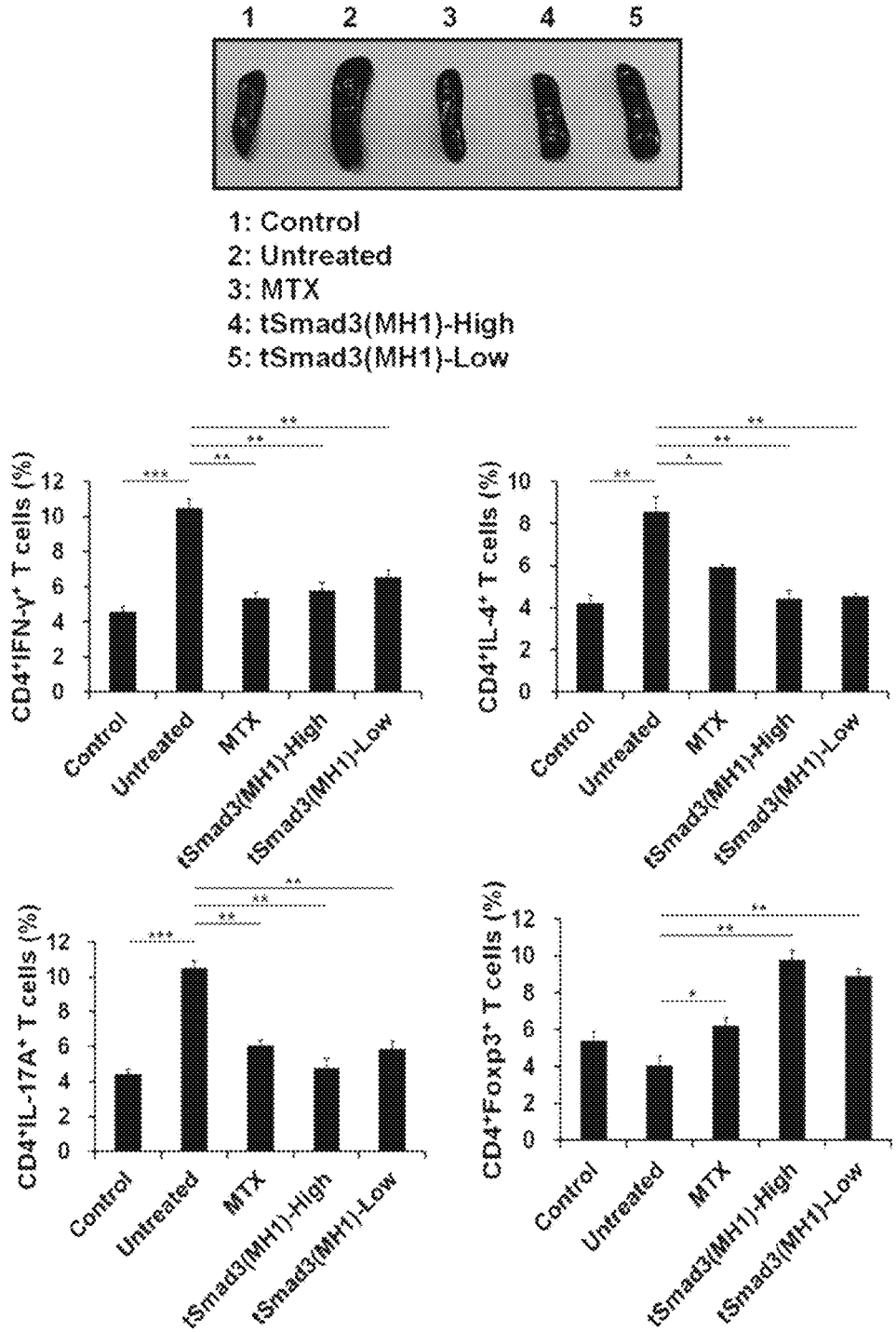
Figure 12F:
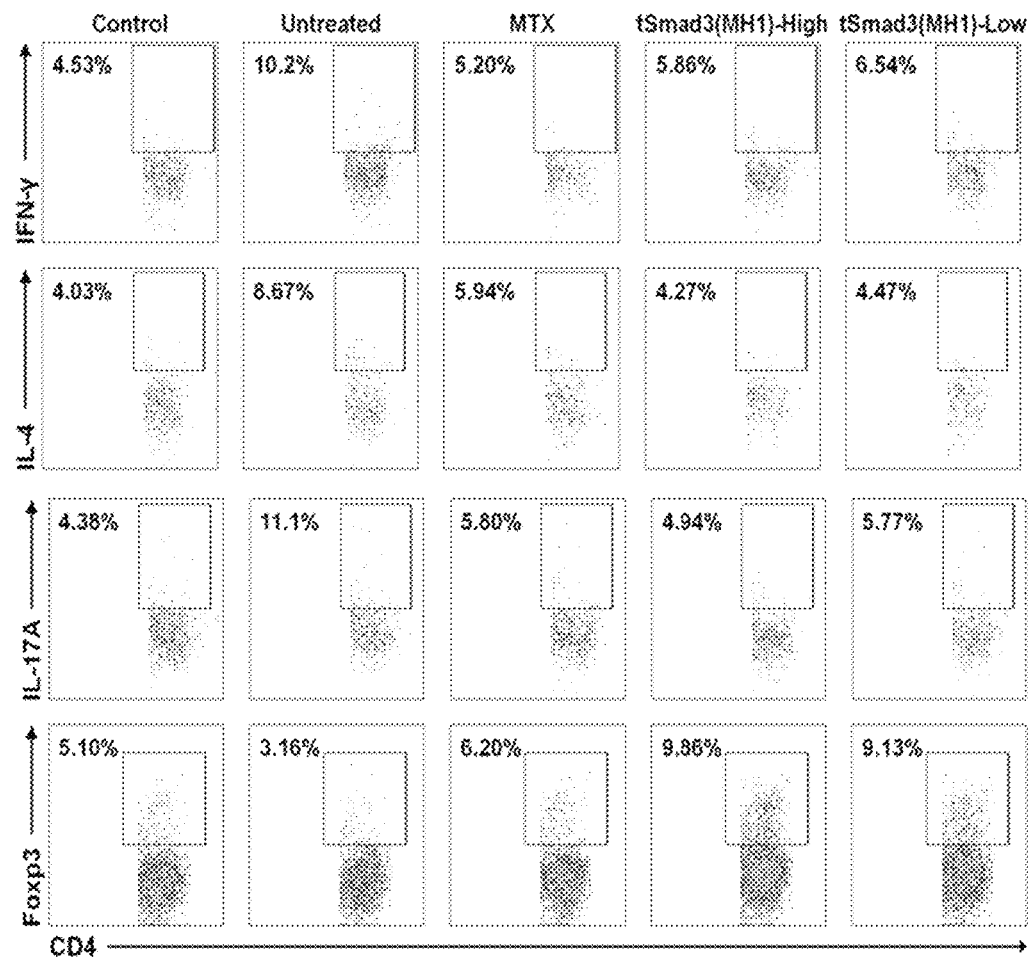

As a result, it could be seen that the expressions of Th1, Th2 and Th17 cells were significantly inhibited, whereas the expression of Treg cells significantly increased. This suggests that the tSmad3(MH1) fusion protein inhibits the function of the inflammatory Th1, Th2 and Th17 cells, but induces the function of Treg cells that inhibit the inhibitory cells (FIGS. 12e and 12f).

Experimental Example 9: Analysis of Delivery of tSmad3(MH1) Recombinant Fusion Protein into Skin Tissue by Topical Administration In order to examine whether or not the tSmad3(MH1) recombinant fusion protein penetrates the mouse skin tissue by topical administration, the skin of the back of mice was topically treated with tSmad3(MH1) for 30 minutes. At 6 hrs, 12 hrs, 24 hrs and 48 hrs after the treatment, the skin was observed using a confocal microscope.

Figure 13:
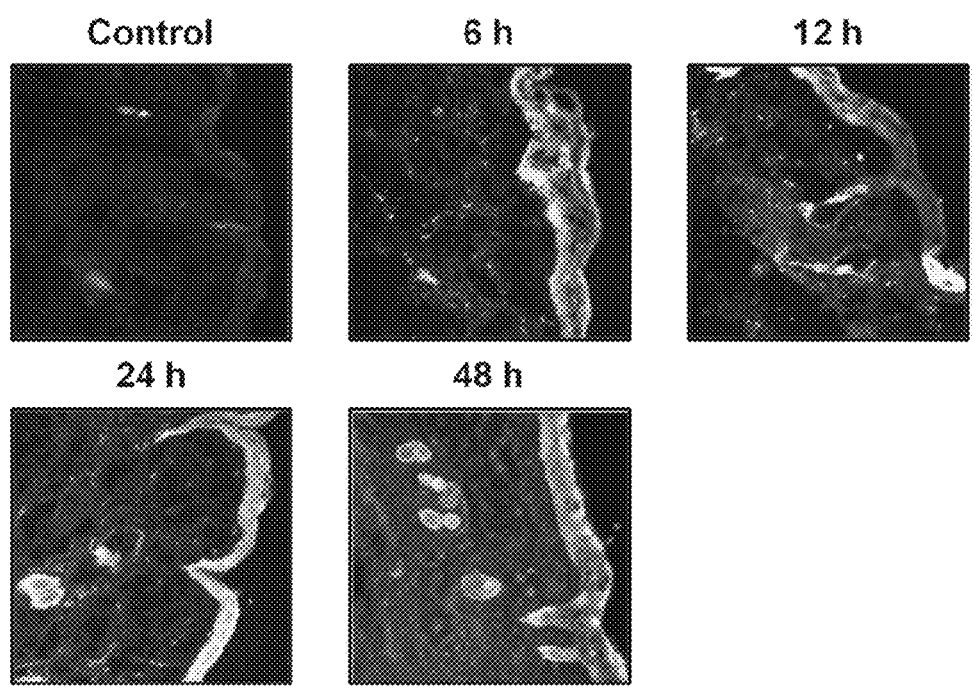
FIG. 13 shows the results of analyzing whether or not tSmad3(MH1) penetrates the skin tissue of mice by topical administration. The skin of mice was treated topically with tSmad3(MH1) for 30 minutes, and then observed using a confocal microscope at 6, 12, 24 and 48 hours after the treatment.

As a result, it could be seen that the tSmad3(MH1) fusion protein was effectively delivered to the dermal layer through the epidermal layer of the skin with the passage of time (FIG. 13).

Experimental Example 10: Acute Toxicity Test for Recombinant Fusion Protein

Using 6-week-old specific pathogen-free (SPF) SD rats obtained from the Daehan Experiment Supply Center, an acute toxicity test was performed in the following manner. The fusion protein of Experimental Example 2 was administered orally once to each animal group (consisting of two animals) at a dose of 1 g/kg, and then the death, clinical symptoms and weight changes of the animals were observed, and hematological tests and blood biochemical tests were performed. In addition, the animals were autopsied, and whether or not the abdominal organs and the thoracic organs were abdominal was visually observed.

As a result, in all the animals administered with the test substance, specific clinical symptoms or dead animals were not found, and in the weight change measurement, hematological tests, blood biochemical tests and autopsy findings, no change in toxicity was observed. Thus, it could be seen that the recombinant fusion protein of Experimental Example 2 of the present invention showed no toxicity in the rats even at a dose of 1 g/kg and that the minimum lethal dose ($LD_{50}$) upon oral administration thereof was 1 g/kg or more, suggesting that it is a safe substance.

Experimental Example 11: Analysis of Autoimmune Disease Therapeutic Effects of Fusion Proteins Having Other Different Protein Transduction Domains The protein transduction domain Hph-1 (SEQ ID NO: 6) used in Experimental Example 2 was replaced with each of Sim-2 (AKAARQAAR), Tat (YGRKKRRQRRR), VP22 (DAATATRGRSAASRPTERPRAPARSASRPRRPVD), Antp (RQIKIWFQNRRMKWKK), Pep-1 (KETWWETWWTEWSQPKKKRKV), PTD-5 (RRQRRTSKLMKR), 7R (RRRRRRR), 9R (RRRRRRRRR), 11R (RRRRRRRRRRR) and CTP (YGRRARRRRRR). Using the fusion proteins having the replaced protein transduction domains, the experiments of Experimental Examples 3, 5, 6, 7 and 8 were repeated.

As a result, it could be seen that the Smad3 protein or the Smad transcription modulation domain protein was effectively delivered into cells in the same manner as when it was fused with Hph-1. Furthermore, these fusion proteins showed the same effects on transcriptional modulation and the regulation of differentiation of immature T cells.

In addition, the fusion proteins showed the same effects on the alleviation of diseases in animal models, suggesting that the Smad3 protein or the Smad3 transcription modulation domain protein can exhibit therapeutic effects against autoimmune diseases regardless of the kind of protein transduction domain.

The above-described embodiments of the present invention are for illustrative purposes only, and it will be understood by those of ordinary skill in the art that various changes in form and details may be made therein without changing the technical spirit and essential features of the present invention. Therefore, the embodiments should be understood in the illustrative sense only and not for the purpose of limitation in all aspects. For example, each component described in a single form may be carried out in a distributed fashion, and likewise, components described in a distributed form may be carried out in a combined fashion.

The scope of the present invention should be defined by the appended claims, and all the changes and modifications derived from the spirit and scope of the claims and equivalents thereof are to be construed to fall within the scope of the present invention.

As described above, the present invention provides a method of effectively inhibiting or treating autoimmune diseases, including lupus nephritis or rheumatoid arthritis, based on clear understanding of signaling pathways that are involved in the development of the autoimmune diseases, and can be effectively used for the treatment, prevention, diagnosis or research of various diseases associated with the signaling pathways.

It is to be understood that the effects of the present invention are not limited to the above-described effects and include all effects which can be deduced from the configuration of the invention described in the detailed description or claims of the present invention.

What is claimed is:

1. A fusion protein for treatment of an autoimmune disease, comprising: a Smad3 protein or a Smad3 transcription modulation domain protein; and a protein transduction domain, wherein the Smad3 protein comprises an amino acid sequence of SEQ ID NO:1 and the Smad3 transcription modulation domain protein comprises an amino acid sequence of SEQ ID NO:3.

2. The fusion protein of claim 1, wherein the Smad3 protein is encoded by a nucleic acid sequence of SEQ ID NO: 2, and the Smad3 transcription modulation domain protein is encoded by a nucleic acid sequence of SEQ ID NO: 4.

3. The fusion protein of claim 1, wherein the protein transduction domain is one or more selected from the group consisting of Hph-1, Sim-2, Tat, VP22, Antp (antennapedia), Pep-1 (peptide-1), PTD-5 (protein transduction domain-5), 7R, 9R, 11R, and CTP (cytoplasmic transduction peptide).

4. The fusion protein of claim 1, wherein the protein transduction domain comprises an amino acid sequence of SEQ ID NO: 5.

5. The fusion protein of claim 1, wherein the protein transduction domain is encoded by a nucleic acid sequence of SEQ ID NO: 6.

6. The fusion protein of claim 1, comprising an amino acid sequence of SEQ ID NO: 7 or 9.

7. The fusion protein of claim 1, which is encoded by a nucleic acid sequence of SEQ ID NO: 8 or 10.

8. The fusion protein of claim 1, wherein the autoimmune disease is one or more selected from the group consisting of systemic lupus erythematosus, rheumatoid arthritis, septic shock, allergic asthma, allergic nasitis, atopic dermatitis, ulcerative colitis, dacryoadenitis, Alzheimer's disease, stroke, arteriosclerosis, vascular restenosis, type I diabetes, type II diabetes, urticaria, conjunctivitis, psoriasis, systemic inflammatory response syndrome, polymyositis, dermatomyositis, polyarthritis nodosa, mixed connective tissue disease, Sjogren's syndrome, gout, Parkinson's disease, amyotrophic lateral sclerosis, diabetic retinopathy, multiple sclerosis, Crohn's disease, chronic thyroiditis, Celiac disease, myasthenia gravis, pemphigus vulgaris, viral diseases, bacterial diseases, radiation-induced disorders, arteriosclerosis, hemangioma, angiofibroma, reperfusion injury, and cardiac hypertrophy.

9. A composition for treatment of an autoimmune disease, containing the fusion protein of claim 1 as an active ingredient.

\* \* \* \* \*